(12) United States Patent
Sadelain et al.

(10) Patent No.: US 10,730,941 B2
(45) Date of Patent: Aug. 4, 2020

(54) ANTIGEN-BINDING PROTEINS TARGETING CD56 AND USES THEREOF

(71) Applicants: MEMORIAL SLOAN-KETTERING CANCER CENTER, New York, NY (US); THE UNITED STATES OF AMERICA AS REPRESENTED BY THE SECRETARY DEPARTMENT OF HEALTH AND HUMAN SERVICES, Bethesda, MD (US)

(72) Inventors: Michel Sadelain, New York, NY (US); Reuben Benjamin, London (GB); Dimiter S. Dimitrov, Frederick, MD (US); Yang Feng, Frederick, MD (US)

(73) Assignees: MEMORIAL SLOAN-KETTERING CANCER CENTER, New York, NY (US); THE UNITED STATES OF AMERICA AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 15/884,608

(22) Filed: Jan. 31, 2018

(65) Prior Publication Data
US 2018/0230214 A1   Aug. 16, 2018

Related U.S. Application Data

(63) Continuation of application No. PCT/US2016/045027, filed on Aug. 1, 2016.

(60) Provisional application No. 62/199,775, filed on Jul. 31, 2015.

(51) Int. Cl.
| | |
|---|---|
| C07K 16/28 | (2006.01) |
| C07K 14/705 | (2006.01) |
| C07K 14/725 | (2006.01) |
| A61K 35/17 | (2015.01) |
| A61P 35/00 | (2006.01) |
| C07K 16/30 | (2006.01) |
| A61K 39/00 | (2006.01) |

(52) U.S. Cl.
CPC .......... *C07K 16/2803* (2013.01); *A61K 35/17* (2013.01); *A61P 35/00* (2018.01); *C07K 14/7051* (2013.01); *C07K 14/70521* (2013.01); *C07K 16/3061* (2013.01); *A61K 2039/505* (2013.01); *C07K 2317/21* (2013.01); *C07K 2317/24* (2013.01); *C07K 2317/30* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/92* (2013.01); *C07K 2319/00* (2013.01); *C07K 2319/02* (2013.01); *C07K 2319/03* (2013.01); *C07K 2319/70* (2013.01)

(58) Field of Classification Search
None
See application file for complete search history.

(56) References Cited

U.S. PATENT DOCUMENTS

| | | |
|---|---|---|
| 4,956,778 A | 9/1990 | Naito |
| 5,091,513 A | 2/1992 | Huston et al. |
| 5,132,405 A | 7/1992 | Huston et al. |
| 5,225,539 A | 7/1993 | Winter |
| 5,399,346 A | 3/1995 | Anderson et al. |
| 5,530,101 A | 6/1996 | Queen et al. |
| 5,585,089 A | 12/1996 | Queen et al. |
| 5,677,425 A | 10/1997 | Bodmer et al. |
| 5,693,762 A | 12/1997 | Queen et al. |
| 5,714,350 A | 2/1998 | Co et al. |
| 5,869,046 A | 2/1999 | Presta et al. |
| 6,121,022 A | 9/2000 | Presta et al. |
| 6,165,745 A | 12/2000 | Ward et al. |
| 6,180,370 B1 | 1/2001 | Queen et al. |
| 6,350,861 B1 | 2/2002 | Co et al. |
| 7,446,190 B2 | 11/2008 | Sadelain et al. |
| 8,389,282 B2 | 3/2013 | Sadelain et al. |
| 2002/0018783 A1 | 2/2002 | Sadelain et al. |
| 2003/0153043 A1 | 8/2003 | Carr et al. |
| 2005/0196754 A1 | 9/2005 | Drmanac et al. |
| 2006/0160178 A1 | 7/2006 | Rothberg et al. |
| 2009/0117095 A1 | 5/2009 | Messmer et al. |

(Continued)

FOREIGN PATENT DOCUMENTS

| | | |
|---|---|---|
| EP | 0 154 316 A2 | 9/1985 |
| EP | 0 401 384 A1 | 12/1990 |

(Continued)

OTHER PUBLICATIONS

Roguska et al., A comparison of two murine monoclonal antibodies humanized by CDR-grafting and variable domain resurfacing. Protein Engineering vol. 9 No. 10 pp. 895-904, 1996 (Year: 1996).*

(Continued)

*Primary Examiner* — Christopher M Babic
*Assistant Examiner* — Arthur S Leonard
(74) *Attorney, Agent, or Firm* — Baker Botts L.L.P.

(57) ABSTRACT

The presently disclosed subject matter provides for methods and compositions for treating cancer (e.g., multiple myeloma). It relates to anti-CD56 antibodies, chimeric antigen receptors (CARs) that specifically target human CD56, and immunoresponsive cells comprising such CARs. The presently disclosed CD56-specific CARs have enhanced immune-activating properties, including anti-tumor activity.

36 Claims, 14 Drawing Sheets
Specification includes a Sequence Listing.

(56) References Cited

U.S. PATENT DOCUMENTS

| | | |
|---|---|---|
| 2010/0254975 A1 | 10/2010 | Hsu et al. |
| 2011/0150905 A1 | 6/2011 | Papadopoulos et al. |
| 2013/0156781 A1 | 6/2013 | Dimitrov et al. |
| 2014/0322218 A1 | 10/2014 | Xiao et al. |
| 2017/0158749 A1* | 6/2017 | Cooper .............. C07K 14/7051 |

FOREIGN PATENT DOCUMENTS

| | | |
|---|---|---|
| EP | 0 592 106 A1 | 4/1994 |
| WO | WO 00/42072 A2 | 7/2000 |
| WO | WO 2013/123061 A1 | 8/2013 |
| WO | WO 2014/052876 A1 | 4/2014 |
| WO | WO 2014/055668 A1 | 4/2014 |
| WO | WO 2014/186469 A2 | 11/2014 |

OTHER PUBLICATIONS

Crossland et al., Capitalizing on Epitope Escape to Avoid T Cell Fratricide without Compromising Targeting of CD56+ Tumors. Mol Therapy, Abstract #198, Jun. 2013: 21, supplemental 1s (Year: 2013).*

Benjamin et al., CD56 targeted chimeric antigen receptors for immunotherapy of multiple myeloma. Astract 3499. AACR 103rd Annual Meeting 2012—Mar. 31-Apr. 4, 2012; Chicago, IL. (Year: 2012).*

Bae et al., Novel epitope evoking CD138 antigen-specific cytotoxic T lymphocytes targeting multiple myeloma and other plasma cell disorders.Br J Haennatol. Nov. 2011;155(3):349-61 (Year: 2011).*

Edwards et al.,The Remarkable Flexibility of the Human Antibody Repertoire; Isolation of Over One Thousand Different Antibodies to a Single Protein, BLyS. JMB, 2003, 334:103-118 (Year: 2003).*

Rudikoff et al. Single amino acid substitution altering antigen-binding specificity (Proceedings of the National Academy of Sciences USA, vol. 79, p. 1979, 1982). (Year: 1982).*

Panka et al. Variable region framework differences result in decreased or increased affinity of variant anti-digoxin antibodies (Proceedings of the National Academy of Sciences USA, vol. 85, 1988) (Year: 1988).*

Krug et al., Stability and activity of MCSP-specific chimeric antigen receptors (CARs) depend on the scFv antigen-binding domain and the protein backbone (Cancer Immuno Immunother, 2015, 64:1623-1635) (Year: 2015).*

Allen, "Ligand-Targeted Therapeutics in Anticancer Therapy," Nat. Rev. Cancer 2:750-763 (2002).

Altschul et al., "Basic Local Alignment Search Tool," J. Mol. Biol. 215:403-410 (1990).

Altschul et al., "Gapped BLAST and PSI-BLAST: a new generation of protein database search programs," Nucleic Acids Res. 25(17):3389-3402 (1997).

Anderson, "Prospects for Human Gene Therapy," Science 226(4673):401-409 (1984).

Arnon et at., "Monoclonal Antibodies for Immunotargeting of Drugs in Cancer Therapy," in Monoclonal Antibodies and Cancer Therapy, Reisfeld et at. (eds.), pp. 243-256 (Alan R. Liss, Inc 1985).

Asano et al., "Cytotoxic Enhancement of a Bispecific Diabody by Format Conversion to Tandem Single-chain Variable Fragment (taFv) the Case of the hEx3 Diabody," J Biol. Chem 286(3):1812-1818 (2011).

Azinovic et al., "Survival benefit associated with human anti-mouse antibody (HAMA) in patients with B-cell malignancies," Cancer Immunol. Immunother. 55:1451-1458 (2006).

Barbas et al., "Human autoantibody recognition of DNA," Proc. Natl. Acad Sci. USA 92:2529-2533 (1995).

Barbas et al., "Recognition of DNA by Synthetic Antibodies," J. Am. Chem. Soc. 116:2161-2162 (1994).

Barber et al., "Chimeric NKG2D receptor-expressing T cells as an immunotherapy for multiple myeloma," Exp. Hematol. 36:1318-1328 (2008).

Bataille et al., "The phenotype of normal, reactive and malignant plasma cells. Identification of 'many and multiple myelomas' and of new targets for myeloma therapy," Haematologica 91:1234-1240 (2006).

Beiboer et al., "Guided Selection of a Pan Carcinoma Specific Antibody Reveals Similar Binding Characteristics yet Structural Divergence Between the Original Murine Antibody and its Human Equivalent," J. Mol. Biol. 296:833-849 (2000).

Benjamin et al., "Abstract 3499: CD56 targeted chimeric antigen receptors for immunotherapy of multiple myeloma," Cancer Research 72:3499 (2012), 6 pages.

Benson et al., "CS1-Directed Monoclonal Antibody Therapy for Multiple Myeloma," J Clin Oncol. 30(16):2013-2015 (2012).

Benton et al., "Screening λgt Recombinant Clones by Hybridization to Single Plaques in situ," Science 196:180-182 (1977).

Berdeja et al., "Phase I Study of Lorvotuzumab Mertansine (LM, IMGN901) in Combination with Lenalidomide (Len) and Dexamethasone (Dex) in Patients with CD56-Positive Relapsed or Relapsed/Refractory Multiple Myeloma (MM)," Blood 120:728 (2012), 6 pages.

Berdeja, "Lorvotuzumab mertansine: antibody-drug-conjugate for CD56+ multiple myeloma," Front Biosci 19:163-170 (2014).

Bird et al., "Single-Chain Antigen-Binding Proteins," Science 242(4877):423-426 (1988).

Blomer et al., "Highly Efficient and Sustained Gene Transfer in Adult Neurons with a Lentivirus Vector," Journal of Virology 71(9):6641-6649 (1997).

Bouxsein et al., "Guidelines for Assessment of Bone Microstructure in Rodents Using Micro-Computed Tomography," J Bone Miner. Res. 25(7):1468-1486 (2010).

Bregni, et al., "Human Peripheral Blood Hematopoietic Progenitors Are Optimal Targets of Retroviral-Mediated Gene Transfer," Blood 80(6):1418-1422 (1992).

Brennan et al., "Preparation of Bispecific Antibodies by Chemical Recombination of Monoclonal Immunoglobulin G1 Fragments," Science 229(4708):81-83 (1985).

Brentjens et al., "CD19-Targeted T Cells Rapidly Induce Molecular Remissions in Adults with Chemotherapy-Refractory Acute Lymphoblastic Leukemia," Scj Transl Med. 5(177):177ra38 (2013).

Brentjens et al., "Eradication of systemic B-cell tumors by genetically targeted human T lymphocytes co-stimulated by CD80 and interleukin-15," Nature Medicine 9(3):279-286 (2003).

Brentjens et al., "Genetically Targeted T Cells Eradicate Systemic Acute Lymphoblastic Leukemia Xenografts," Clin Cancer Res 13(18):5426-5435 (2007).

Brentjens et al., "Safety and persistence of adoptively transferred autologous CD19-targeted T cells in patients with relapsed or chemotherapy refractory B-cell leukemias," Blood 118(18):4817-4828 (2011).

Brigham et al., "Rapid Communication: In vivo Transfection of Murine Lungs with a Functioning Prokaryotic Gene Using a Liposome Vehicle," Am. J. Med. Sci. 298(4):278-281 (1989).

Brocks et al., "A TNF receptor antagonistic scFv, which is not secreted in mammalian cells, is expressed as a soluble mono- and bivalent scFv derivative in insect cells," Immunotechnology 3:173-184 (1997).

Buckley, "Molecular Defects in Human Severe Combined Immunodeficiency and Approaches to Immune Reconstitution," Annu Rev Immunol. 22:625-655 (2004).

Cao et al., "The fucosylated histo-blood group antigens H type 2 (blood group O, CD173) and Lewis Y (CD174) are expressed on CD34+ hematopoietic progenitors but absent on mature lymphocytes," Glycobiology 11(8):677-683 (2001).

Carbone et al., "HLA class I, NKG2D, and natural cytotoxicity receptors regulate multiple myeloma cell recognition by natural killer cells," Blood 105:251-258 (2005).

Carpenter et al., "B-cell Maturation Antigen is a Promising Target for Adoptive T-cell Therapy of Multiple Myeloma," Clin Cancer Res. 19(8):2048-2060 (2013).

Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy 8:423-430 (1997).

(56) References Cited

OTHER PUBLICATIONS

Chen et al., "Selection and Analysis of an Optimized Anti -VEGF Antibody: Crystal Structure of an Affinity-matured Fab in Complex with Antigen," J. Mol. Biol. 293:865-881 (1999).
Chu et al., "Genetic Modification of T Cells Redirected toward CS1 Enhances Eradication of Myeloma Cells," Clin Cancer Res. 20(15):3989-4000 (2014).
Cornetta et al., "Gene Transfer into Primates and Prospects for Gene Therapy in Humans," Progress in Nucleic Acid Research and Molecular Biology 36:311-322 (1987).
Cox et al., "A Directory of Human Germ-line VH Segments Reveals a Strong Bias in their Usage," Eur. J. Immunol 24:827-836 (1994).
Crossland et al., "Capitalizing on Epitope Escape to Avoid T Cell Fratricide without Compromising Targeting of CD56+ Tumors," Molecular Therapy 21(Suppl. 1):Abstract #198 (2013).
Crossland et al., "CD56-Specific T Cells: Using Genetically Engineered T Cells to Redirect Specificity to a T Cell Expressed Antigen," (2014) UT GSBS Dissertations and Theses (Open Access). 493, p. 1-232 http://digitalcommons.library.tmc.edu/utgsbs_dissertations/493.
Cunningham et al., "Isolation and Characterisation of a Recombinant Antibody Fragment That Binds NCAM1-Expressing Intervertebral Disc Cells," Plos One 8(12):e83678 (2013), 11 pages.
Danos et al., "Safe and efficient generation of recombinant retroviruses with amphotropic and ecotropic host ranges," Proc. Nat. Acad. Sci. USA 85:6460-6464 (1988).
Dhodapkar et al., "A Reversible Defect in Natural Killer T Cell Function Characterizes the Progression of Premalignant to Malignant Multiple Myeloma," J. Exp. Med. 197(12):1667-1676 (2003)cytot.
Ditzel et al., "Determinants of polyreactivity in a large panel of recombinant human antibodies from HIV-1 infection," J Immunol 157:739-749 (1996).
Dudley et al., "Adoptive Cell Therapy for Patients with Metastatic Melanoma: Evaluation of Intensive Myeloablative Chemoradiation Preparative Regimens," J Clin Oncol 26:5233-5239 (2008).
Dupont et al., "Artificial Antigen-Presenting Cells Transduced with Telomerase Efficiently Expand Epitope-Specific, Human Leukocyte Antigen-Restricted Cytotoxic T Cells," Cancer Res 65:5417-5427 (2005).
Eglitis et al., "Retroviral Vectors for Introduction of Genes into Mammalian Cells," BioTechniques 6(7):608-614 (1988).
Felgner et al., "Lipofection: A highly efficient, lipid-mediated DNA-transfection procedure," Proc. Natl. Acad. Sci. USA 84:7413-7417 (1987).
Feng et al., "A novel human monoclonal antibody that binds with high affinity to mesothelin-expressing cells and kills them by antibody-dependent cell-mediated cytotoxicity," Mol. Cancer Ther. 8(5):1113-1118 (2009).
Feng et al., "Differential killing of CD56-expressing cells by drug-conjugated human antibodies targeting membrane-distal and membrane-proximal non-overlapping epitopes," MABS 8(4):799-810 (2016).
Fife et al., "Inhibition of T cell activation and autoimmune diabetes using a B cell surface-linked CTLA-4 agonist," J Clin Invest 116(8):2252-2261 (2006).
Fischer et al., "Severe combined immunodeficiency. A model disease for molecular immunology and therapy," Immunol Rev 203:98-109 (2005).
Friedmann, "Progress Toward Human Gene Therapy," Science 244(4910):1275-1281 (1989).
Gade et al., "Targeted Elimination of Prostate Cancer by Genetically Directed Human T Lymphocytes," Cancer Res 65(19):9080-9088 (2005).
Garfall, "Safety and e cacy of anti-CD19 chimeric antigen receptor (CAR)-modi ed autologous T cells (CTL019) in advanced multiple myeloma," ASCO, Abstract (2015).
Gascon et al., "Polysialic acid-neural cell adhesion molecule in brain plasticity: From synapses to integration of new neurons," Brain Res Rev. 56:101-118 (2007).
Gattenloehner et al., "Novel RUNX1 isoforms determine the fate of acute myeloid leukemia cells by controlling CD56 expression," Blood 110:2027-2033 (2007).
Ghani et al., "Efficient Human Hematopoietic Cell Transduction Using RD114- and GALV-Pseudotyped Retroviral Vectors Produced in Suspension and Serum-Free Media," Hum Gene Ther. 20:966-974 (2009).
Giomarelli et al., "Inhibition of thrombin-induced platelet aggregation using human single-chain Fv antibodies specific for TREM-like transcript-I," Thromb Haemost 97:955-963 (2007).
Glennie et al., "Preparation and performance of bispecific F(ab' gamma)2 antibody containing thioether-linked FAB' gamma fragments," J. Immunol. 139:2367-2375 (1987).
Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia 1(2):123-127 (1999).
Grunstein et al., "Colony hybridization: A method for the isolation of cloned DNAs that contain a specific gene," Proc. Nat. Acad. Sci., USA 72(10):3961-3965 (1975).
Grupp et al., "Chimeric Antigen Receptor-Modified T cells for Acute Lymphoid Leukemia," N Engl J Med. 368(16):1509-1518 (2013).
Heffner et al., "BT062, an Antibody-Drug Conjugate Directed Against CD138, Given Weekly for 3 Weeks in Each 4 Week Cycle: Safety and Further Evidence of Clinical Activity," Blood 120:4042, 4 pages (2012).
Hellstrom et al., "Antibodies for Drug Delivery," in Controlled Drug Delivery (2nd Ed.), Robinson et al. (eds.), pp. 623-653 (Marcel Dekker, Inc. 1987).
Ho et al., BioChim Biophys Acta 1638(3):257-266 (2003).
Hollyman et al., "Manufacturing Validation of Biologically Functional T Cells Targeted to CD19 Antigen for Autologous Adoptive Cell Therapy," J Immunother 32:169-180 (2009).
Hsi et al., "CS1, a Potential New Therapeutic Antibody Target for the Treatment of Multiple Myeloma," Clin Cancer Res 14(9):2775-2784 (2008).
Hughes et al., "Retroviral Gene Transfer to Primitive Normal and Leukemic Hematopoietic Cells Using Clinically Applicable Procedures," J. Clin Invest. 89:1817-1824 (1992).
Hunder et al., "Treatment of Metastatic Melanoma with Autologous CD4+ T cells against NY- ESO-1," N. Engl. J. Med. 358:2698-2703 (2008).
Huston et al., "Protein engineering of antibody binding sites: Recovery of specific activity in an anti-digoxin single-chain Fv analogue produced in *Escherichia coli*," Proc. Natl. Acad. Sci. 85:5879-5883 (1988).
International Search Report dated Dec. 28, 2016 in International Application No. PCT/US16/45027.
Ishitsuka et al., "Targeting CD56 by the maytansinoid immunoconjugate IMGN901 (huN901-DM1): a potential therapeutic modality implication against natural killer/T cell malignancy," British Journal of Haematology, 141:129-131 (2008).
Jiang et al., "Transfection of chimeric anti-CD138 gene enhances natural killer cell activation and killing of multiple myeloma cells," Mol Oncol. 8:297-310 (2014).
Johnson, "Gene Therapy for Cystic Fibrosis," Chest 107:77S-83S (1995).
Jones et al., "Replacing the complementarity-determining regions in a human antibody with those from a mouse," Nature 321:522-525 (1986).
Kabat et al., Sequences of Proteins of Immunological Interest, 4th US Department of Health and Human Services, National Institutes of Health (1987).
Kabat, E. A., et al. (1991) Sequences of Proteins of Immunological Interest, Fifth Edition, U.S. Department of Health and Human Services, NIH Publication No. 91-3242.
Kalos, et al., "T Cells with Chimeric Antigen Receptors have Potent Antitumor Effects and Can Establish Memory in Patients with Advanced Leukemia," Sci Transl Med. 3(95):95ra73 (2011).

(56) References Cited

OTHER PUBLICATIONS

Karpovsky et al., "Production of Target-Specific Effector Cells Using Hetero-Cross—Linked Aggregates Containing Anti-Target Cell and Anti-Fcγ Receptor Antibodies," J. Exp. Med. 160:1686-1701 (1984).
Kawano et al., "Multiple myeloma cells expressing low levels of CD138 have an immature phenotype and reduced sensitivity to lenalidomide," Int. J Oncol 41:876-884 (2012).
Kershaw et al., "Gene-Engineered T cells as a Superior Adjuvant Therapy for Metastatic Cancer," J Immunol 173:2143-2150 (2004).
Kido et al., "Use of a retroviral vector with an internal opsin promoter to direct gene expression to retinal photoreceptor cells," Current Eye Research 15:833-844 (1996).
Kimmel, "Identification and Characterization of Specific Clones: Strategy for Confirming the Validity of Presumptive Clones," Methods Enzymol. 152:507-511 (1987).
Kitamura et al., "Specificity analysis of blood group Lewis-y (Le(y)) antibodies generated against synthetic and natural Le(y) determinants," Proc Natl Acad Sci USA 91:12957-12961 (1994).
Klechevsky et al., "Antitumor activity of immunotoxins with T-cell receptor-like specificity against human melanoma xenografts," Cancer Res 68(15):6360- 6367 (2008).
Klimka et al., "Human anti-CD30 recombinant antibodies by guided phage antibody selection using cell panning," British J of Cancer 83(2):252-260 (2000).
Kloss et al., "Combinatorial antigen recognition with balanced signaling promotes selective tumor eradication by engineered T cells," Nat Biotechnol. 31(1):71-75 (2013).
Krause et al., "Antigen-dependent CD28 Signaling Selectively Enhances Survival and Proliferation in Genetically Modified Activated Human Primary T Lymphocytes," J. Exp. Med. 188(4):619-626 (1998).
Krishnan et al., "Autologous haemopoietic stem-cell transplantation followed by allogeneic or autologous haemopoietic stem-cell transplantation in patients with multiple myeloma (BMT CTN 0102): a phase 3 biological assignment trial," Lancet Oncol. 12:1195-1203 (2011).
Le Gal La Salle et al., "An Adenovirus Vector for Gene Transfer into Neurons and Glia in the Brain Science," 259:988-990 (1993).
Ledbetter et al., "Agonistic Activity of a CD40-Specific Single-Chain Fv Constructed from the Variable Regions of mAb G28-5," Crit Rev Immunol 17:427-435 (1997).
Lin et al., "Flow Cytometric Immunophenotypic Analysis of 306 Cases of Multiple Myeloma," Am J Clin Pathol 121:482-488 (2004).
Linette et al., "Cardiovascular toxicity and titin cross-reactivity of affinity-enhanced T cells in myeloma and melanoma," Blood 122(6):863-871 (2013).
Liu et al., "Heteroantibody duplexes target cells for lysis by cytotoxic T lymphocytes," Proc. Natl. Acad. Sci. USA 82:8648-8652 (1985).
Loffler et al., "A recombinant bispecific single-chain antibody, CD19 3 CD3, induces rapid and high lymphoma-directed cytotoxicity by unstimulated T lymphocytes," Blood 95:2098-2103 (2000).
Lokhorst et al., "Donor Lymphocyte Infusions for Relapsed Multiple Myeloma after Allogeneic Stem-Cell Transplantation: Predictive Factors for Response and Long-Term Outcome," J. Clin Oncol. 18:3031-3037 (2000).
Lonial et al., "Elotuzumab in Combination With Lenalidomide and Low-Dose Dexamethasone in Relapsed or Refractory Multiple Myeloma," J Clin Oncol 30(16):1953-1959 (2012).
Lyddane et al., "Cutting Edge: CD28 Controls Dominant Regulatory T Cell Activity during Active Immunization," J Immunol. 176:3306-3310 (2006).
Maher et al., "Human T-lymphocyte cytotoxicity and proliferation directed by a single chimeric TCRζ/CD28 receptor," Nat Biotechnol. 20:70-75 (2002).
Markley et al., "IL-7 and IL-21 are superior to IL-2 and IL-15 in promoting human T cell-mediated rejection of systemic lymphoma in immunodeficient mice," Blood 115(17):3508-3519 (2010).

Mateo et al., "Prognostic Value of Immunophenotyping in Multiple Myeloma: A Study by the PETHEMA/GEM Cooperative Study Groups on Patients Uniformly Treated with High-Dose Therapy," J Clin Oncol. 26:2737-2744 (2008).
Matsui et al., "Characterization of clonogenic multiple myeloma cells," Blood 103:2332-2336 (2004).
Maude et al., "Chimeric Antigen Receptor T Cells for Sustained Remissions in Leukemia," N Engl. J Med. 371(16):1507-1517 (2014).
Maus et al., "T Cells Expressing Chimeric Antigen Receptors Can Cause Anaphylaxis in Humans," Cancer Immunol Res 1(1):26-31 (2013).
McCafferty et al., "Phage antibodies: filamentous phage displaying antibody variable domains," Nature 348:552-554 (1990).
Mihara et al., "Activated T-cell-mediated Immunotherapy with a Chimeric Receptor against CD38 in B-cell Non-Hodgkin Lymphoma," J Immunother. 32:737-743 (2009).
Mihara et al., "T-cell immunotherapy with a chimeric receptor against CD38 is effective in eliminating myeloma cells," Leukemia 26:365-367 (2012).
Miller et al., "Generation of Helper-Free Amphotropic Retroviruses That Transduce a Dominant-Acting, Methotrexate-Resistant Dihydrofolate Reductase Gene," Mol. Cell. Biol. 5(3):431-437 (1985).
Miller et al., "Improved Retroviral Vectors for Gene Transfer and Expression," Biotechniques 7(9):980-990 (1989).
Miller et al., "Redesign of Retrovirus Packaging Cell Lines to Avoid Recombination Leading to Helper Virus Production," Mol. Cell. Biol. 6(8):2895-2902 (1986).
Miller, "Retrovirus Packaging Cells," Human Gene Therapy 1:5-14 (1990).
Miyoshi et al., "Stable and efficient gene transfer into the retina using an HIV-based lentiviral vector," Proc. Natl. Acad. Sci. USA 94:10319-10323 (1997).
Moen, "Directions in Gene Therapy," Blood Cells 17:407-416 (1991).
Moosmayer et al., "A single-chain TNF receptor antagonist is an effective inhibitor of TNF mediated cytotoxicity," Ther Immunol. 2:31-40 (1995).
Moreaux et al., "BAFF and APRIL protect myeloma cells from apoptosis induced by interleukin 6 deprivation and dexamethasone," Blood 103:3148-3157 (2004).
Morgan et al., "Cancer Regression and Neurological Toxicity Following Anti-MAGE-A3 TCR Gene Therapy," J Immunother. 36:133-151 (2013).
Morgan et al., "Cancer Regression in Patients After Transfer of Genetically Engineered Lymphocytes," Science 314:126-129 (2006).
Morgan et al., "Case Report of a Serious Adverse Event following the Administration of T Cells Transduced with a Chimeric Antigen Receptor Recognizing ERBB2," Molecular Therapy 18(4):843-851 (2010).
Morris, "Epitope Mapping of Protein Antigens by Competition ELISA," The Protein Protocols Handbook, pp. 595-600 (1996).
Muller et al., "Improved Pharmacokinetics of Recombinant Bispecific Antibody Molecules by Fusion to Human Serum Albumin," J Biol. Chem 282(17):12650-12660 (2007).
Myers et al., "Optimal alignments in linear space," CABIOS 4(1):11-17 (1988).
Naldini et al., "In Vivo Gene Delivery and Stable Transduction of Nondividing Cells by a Lentiviral Vector," Science 272:263-267 (1996).
Needleman et al., "General Method Applicable to the Search for Similarities in the Amino Acid Sequence of Two Proteins," J. Mol. Biol. 48:443-453 (1970).
Ono et al., "Plasmid DNAs directly injected into mouse brain with lipofectin can be incorporated and expressed by brain cells," Neuroscience Letters 117:259-263 (1990).
Order, "Analysis, Results, and Future Prospective of the Therapeutic Use of Radiolabeled Antibody in Cancer Therapy," in Monoclonal Antibodies for Cancer Detection and Therapy, Baldwin et at. (eds.), pp. 303-316 (Academic Press 1985).

(56) References Cited

OTHER PUBLICATIONS

Panelli et al., "A Tumor-Infiltrating Lymphocyte from a Melanoma Metastasis with Decreased Expression of Melanoma Differentiation Antigens Recognizes MAGE-12," J. Immunol 164:4382-4392 (2000).
Panelli et al., "Expansion of Tumor-T Cell Pairs from Fine Needle Aspirates of Melanoma Metastases," J Immunol 164:495-504 (2000).
Papanicolaou et al., "Rapid expansion of cytomegalovirus—specific cytotoxic T lymphocytes by artificial antigen-presenting cells expressing a single HLA allele," Blood 102:2498-2505 (2003).
Pastan et al., "Immunotoxins in cancer therapy," Curr. Opin. Investig. Drugs 3(7):1089-1091 (2002).
Paulus, "Preparation and Biomedical Applications of Bispecific Antibodies," Behring Inst. Mitt. 78:118-132 (1985).
Payne, "Progress in immunoconjugate cancer therapeutics," Cancer Cell 3:207-212 (2003).
Peinert et al., "Gene-modified T cells as immunotherapy for multiple myeloma and acute myeloid leukemia expressing the Lewis Y antigen," Gene Ther. 17:678-686 (2010).
Peter et al., "Protective effects of an anti-melanocortin-4 receptor scFv derivative in lipopolysaccharide-induced cachexia in rats," J Cachexia Sarcopenia Muscle 4:79-88 (2013).
Peter et al., "scFv Single Chain Antibody Variable Fragment as Inverse Agonist of the β2-Adrenergic Receptor," J Biol. Chem 278(38):36740-36747 (2003).
Plesner et al., "Preliminary Safety and Efficacy Data of Daratumumab in Combination With Lenalidomide and Dexamethasone in Relapsed or Refractory Multiple Myeloma," Blood 122:1986, 5 pages (2013).
Porter et al., "Chimeric Antigen Receptor-Modified T cells in Chronic Lymphoid Leukemia," N. Engl. J. Med. 365:725-733 (2011).
Queen et al., "A humanized antibody that binds to the interleukin 2 receptor," Proc. Natl. Acad. Sci. USA 86:10029-10033 (1989).
Rader et al., "A phage display approach for rapid antibody humanization: Designed combinatorial V gene libraries," Proc. Natl. Acad. Sci. USA 95:8910-8915 (1998).
Ramos et al., "Clinical responses with T lymphocytes targeting malignancy-associated κ light chains," The Journal of Clinical Investigation 126(7):2588-2596 (2016).
Rapoport et al., "Engineered T-Cells Expressing an HLA-Restricted Affinity-Enhanced TCR in Advanced Multiple Myeloma Patients Post Auto-SCT Engraft and Are Associated with Encouraging Post Auto-SCT Responses," Blood 122:766, 6 pages (2013).
Raspadori et al., "CD56 antigenic expression in acute myeloid leukemia identifies patients with poor clinical prognosis," Leukemia 15:1161-1164 (2001).
Rawstron et al., "Distribution of myeloma plasma cells in peripheral blood and bone marrow correlates with CD56 expression," Br J Haematol. 104:138-143 (1999).
Riechmann et al., "Reshaping human antibodies for therapy," Nature 332:323-327 (1988).
Ritter et al., "Serological Analysis of Human Anti-Human Antibody Responses in Colon Cancer Patients Treated with Repeated Doses of Humanized Monoclonal Antibody A33," Cancer Res 61:6851-6859 (2001).
Riviere et al., "Novel Strategies for Cancer Therapy: The Potential of Genetically Modified T Lymphocytes," Curr Hematol Rep 3:290-297 (2004).
Roguska et al., "Humanization of murine monoclonal antibodies through variable domain resurfacing," Proc Natl Acad Sci USA 91:969-973 (1994).
Rosenberg et al., "Adoptive cell transfer: a clinical path to effective cancer immunotherapy," Nat. Rev. Cancer 8:299-308 (2008).
Rosenberg et al., "Screening for Diabetic Retinopathy," N Engl J. Med 376(16):1587-1588 (2017).
Sadelain et al., "Targeting Tumours With Genetically Enhanced T Lymphocytes," Nat Rev Cancer 3:35-45 (2003).
Sadelain et al., "The basic principles of chimeric antigen receptor (CAR) design," Cancer Discovery 3(4):388-398 (2013).
Sadelain et al., "The promise and potential pitfalls of chimeric antigen receptors," Curr Opin Immunol 21:215-223 (2009).
Saito et al., "Drug delivery strategy utilizing conjugation via reversible disulfide linkages: role and site of cellular reducing activities," Adv. Drug Deliv. Rev. 55:199-215 (2003).
Salama et al., "Donor leukocyte infusions for multiple myeloma," Bone Marrow Transplant. 26:1179-1184 (2000).
Senter et al., "Selective activation of anticancer prodrugs by monoclonal antibody-enzyme conjugates," Adv. Drug Deliv. Rev. 53:247-264 (2001).
Sentman et al., "NKG2D CARs as Cell Therapy for Cancer," Cancer J. 20:156-159 (2014).
Sharp, "Gene Therapy," The Lancet 337:1277-1278 (1991).
Shieh et al., "Transgenic Expression of Single-Chain Anti-CTLA-4 Fv on 13 Cells Protects Nonobese Diabetic Mice from Autoimmune Diabetes," J Immunol 183:2277-2285 (2009).
Stephan et al., "T cell-encoded CD80 and 4-1BBL induce auto- and transcostimulation, resulting in potent tumor rejection," Nat. Med. 13(12):1440-1449 (2007).
Straubinger et al., "Liposomes as Carriers for Intracellular Delivery of Nucleic Acids," Methods in Enzymology 101:512-527 (1983).
Supplementary European Search Report dated Mar. 19, 2019 in Application No. EP 16833684.
Tassone et al., "In Vitro and in Vivo Activity of the Maytansinoid Immunoconjugate huN901-N2'-Deacetyl -N2' -(3-Mercapto-1-Oxopropyl)-Maytansine against CD56+ Multiple Myeloma Cells," Cancer Res. 64:4629-4636 (2004).
Thorpe et al., "The Preparation and Cytotoxic Properties of Antibody-Toxin Conjugates," Immunol. Rev., 62:119-158 (1982).
Thorpe, "Antibody Carriers of Cytotoxic Agents in Cancer Therapy: A Review," in Monoclonal Antibodies '84: Biological and Clinical Applications, Pinchera et al. (eds.), pp. 475-506 (1985).
Tjandra et al., "Development of human anti-murine antibody (HAMA) response in patients," Immunol Cell Biol. 68:367-376 (1990).
Tolstoshev et al., "Gene expression using retroviral vectors," Current Opinion in Biotechnology 1:55-61 (1990).
Tomlinson et al., "The Repertoire of Human Germline VH Sequences Reveals about Fifty Groups of VH Segments with Different Hypervariable Loops", J. Mol. Biol. 227:776-798 (1992).
Trail et al., "Monoclonal antibody drug immunoconjugates for targeted treatment of cancer," Cancer Immunol. Immunother. 52:328-337 (2003).
Tse et al., "How I treat NK/T-cell lymphomas," Blood 121(25):4997-5005 (2013).
van Rhee et al., "NY-ESO-1 is highly expressed in poor-prognosis multiple myeloma and induces spontaneous humoral and cellular immune responses," Blood 105:3939-3944 (2005).
Vera et al., "T lymphocytes redirected against the κ light chain of human immunoglobulin efficiently kill mature B lymphocyte-derived malignant cells," Blood 108:3890-3897 (2006).
Vivier et al., "Innate or Adaptive Immunity? The Example of Natural Killer Cells," Science 331:44-49 (2011).
Wahl et al., "Improved Radioimaging and Tumor Localization with Monoclonal F(ab')2," J Nucl Med. 24:316-325 (1983).
Wahl et al., "Molecular Hybridization of Immobilized Nucleic Acids: Theoretical Concepts and Practical Considerations," Methods Enzymol 152:399-407 (1987).
Wajchman et al., "Ex vivo Expansion of CD8+CD56+ and CD8+ CD56– Natural Killer T Cells Specific for MUC1 Mucin," Cancer Res. 64:1171-1180 (2004).
Weiner et al., "The role of T cell activation in anti-CD3 x antitumor bispecific antibody therapy," J Immunology 152:2385-2392 (1994).
Whiteman et al., "Lorvotuzumab mertansine, a CD56-targeting antibody-drug conjugate with potent antitumor activity against small cell lung cancer in human xenograft models," MABS 6(2):556-566 (2014).
Wolff et al., "Direct Gene Transfer into Mouse Muscle in Vivo," Science 247(4949):1465-1468 (1990).
Wu et al., "Receptor-mediated Gene Delivery and Expression in Vivo," Journal of Biological Chemistry 263(29):14621-14624 (1988).
Wu et al., "Targeting Genes: Delivery and Persistent Expression of a Foreign Gene Driven by Mammalian Regulatory Elements in Vivo," Journal of Biological Chemistry 264(29):16985-16987 (1989).

(56) References Cited

OTHER PUBLICATIONS

Xie et al., "Direct demonstration of MuSK involvement in acetylcholine receptor clustering through identification of agonist ScFv," Nat Biotech 15:768-771 (1997).

Xu et al., "Correction of the enzyme deficiency in hematopoietic cells of Gaucher patients using a clinically acceptable retroviral supernatant transduction protocol," Exp. Hemat 22:223-230 (1994).

Yong et al., "Evaluation of Bcma as a Therapeutic Target in Multiple Myeloma Using an Antibody-Drug Conjugate," Blood 122:4447, 5 pages (2013).

Zhao et al., "Characteristics of an scFv Antibody Fragment That Binds to Immunoglobulin G of Graves' Disease Patients and Inhibits Autoantibody-Mediated Thyroid-Stimulating Activity," Hyrbidoma, 27(6):445-451 (2008).

Zonder et al., "A phase 1, multicenter, open-label, dose escalation study of elotuzumab in patients with advanced multiple myeloma," Blood 120(3):552-559 (2012).

\* cited by examiner

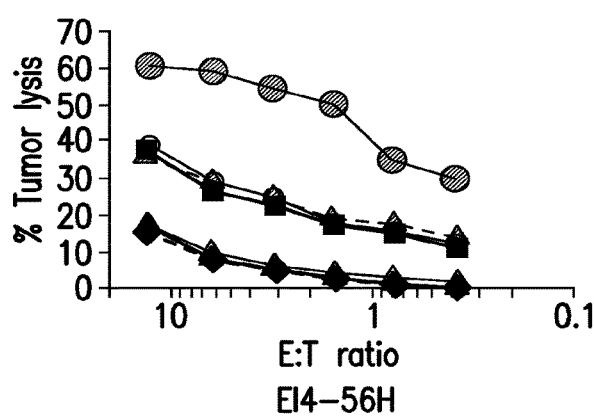
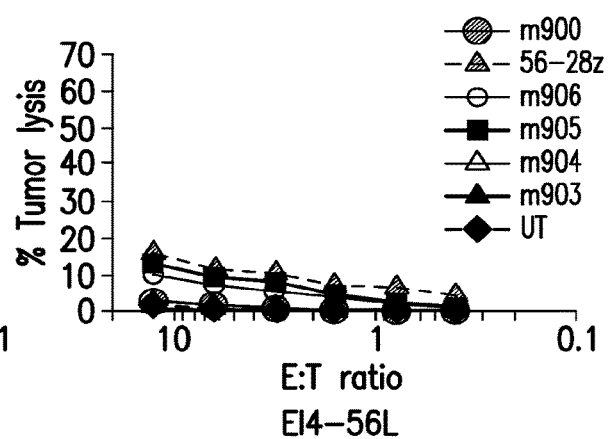
FIG. 2A  FIG. 2B
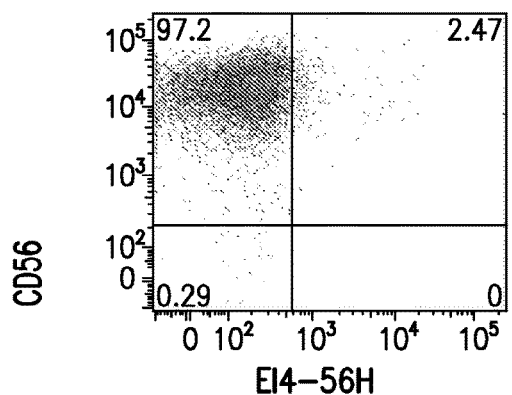
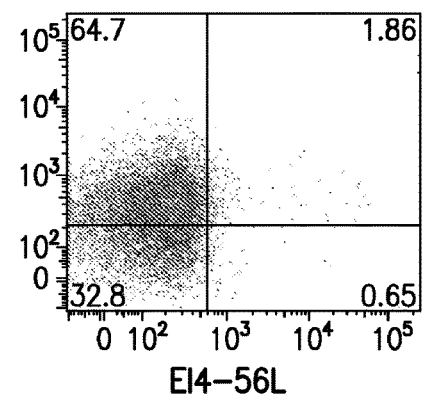
FIG. 2C  FIG. 2D

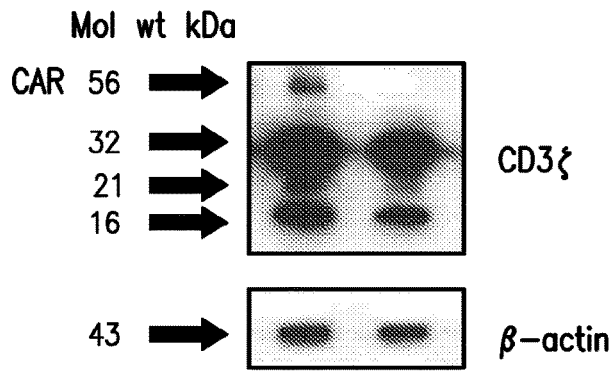
FIG. 6A
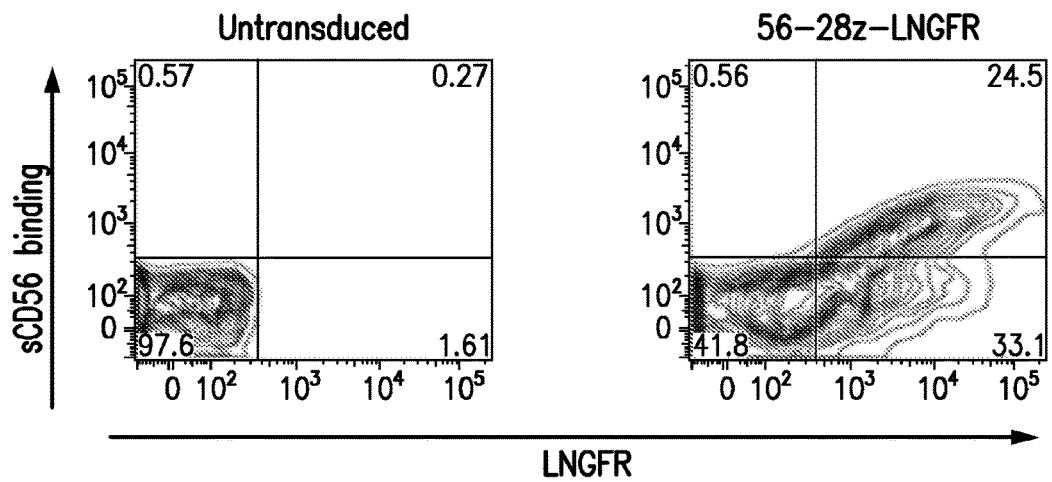
FIG. 6B
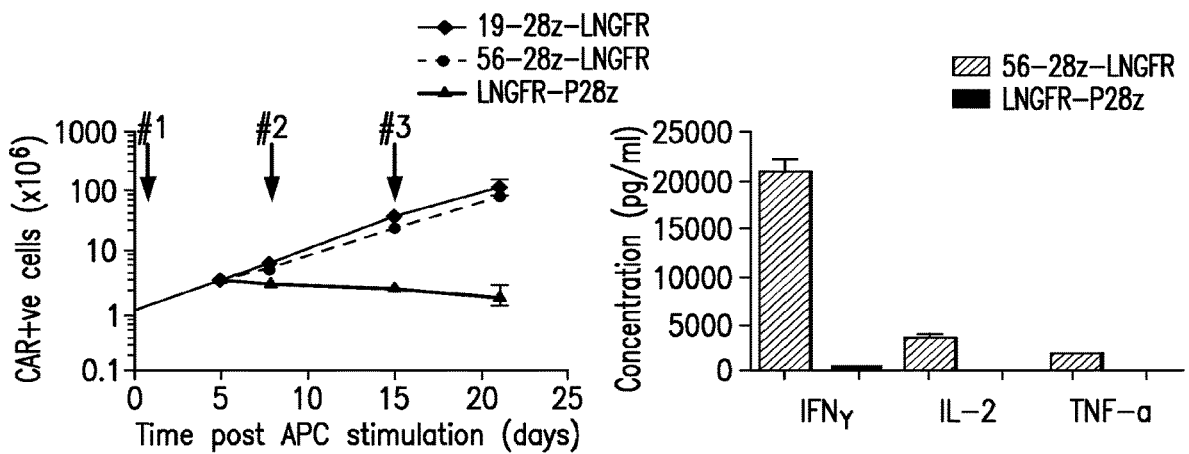
FIG. 6C
FIG. 6D

SEQUENCE LISTING

<160> NUMBER OF SEQ ID NOS: 60

<210> SEQ ID NO 1
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1

Gly Asp Ser Val Ser Ser Asn Ser Ala Ala
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Tyr Tyr Arg Ser Lys Trp Tyr Asn
1               5

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Arg Glu Asn Ile Ala Ala Trp Thr Trp Ala Phe Asp Ile Trp
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Val Ser Ser Ser Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Thr Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Tyr Gly Ser Ser Pro Thr Phe
1               5
```

```
<210> SEQ ID NO 7
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Asn Ile Ala Ala Trp Thr Trp Ala Phe Asp
            100                 105                 110

Ile Trp Gly Gln Gly Thr Met Val Thr Val Ser Ser
        115                 120

<210> SEQ ID NO 8
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Leu Ala Pro Arg Leu Leu
        35                  40                  45

Ile Tyr Asp Thr Ser Leu Arg Ala Thr Asp Ile Pro Asp Arg Phe Ser
    50                  55                  60

Gly Ser Gly Ser Gly Thr Ala Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gln Gly Thr Lys Val Glu Ile Lys Arg Thr Val Ala
            100                 105                 110

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Thr Phe Thr Gly Tyr Tyr
```

```
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Asn Pro Asn Ser Gly Gly Thr
1               5

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Arg Asp Leu Ser Ser Gly Tyr Ser Gly Tyr Phe Asp Tyr Trp
1               5                   10                  15

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ser Leu Leu His Ser Asn Gly Tyr Asn Tyr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Ser Leu Leu His Ser Asn Gly Tyr Asn Phe
1               5                   10

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Gly Ser
1

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 15

Met Gln Ala Leu Gln Thr Leu Thr Phe
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Gln Ala Leu Gln Thr Pro Pro Tyr Thr
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Gln Ala Leu Gln Ser Pro Phe Thr Phe
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Gln Ser Leu Gln Thr Pro Trp Thr Phe
1               5                   10

<210> SEQ ID NO 19
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Ser Ser Gly Tyr Ser Gly Tyr Phe Asp Tyr Trp Gly

-continued

```
                100                 105                 110
Gln Gly Thr Leu Val Thr Val Ser Ser
        115                 120

<210> SEQ ID NO 20
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Leu Thr Phe Gly Gln Gly Thr Arg Leu Glu Ile Lys Arg
            100                 105                 110

Thr Val Ala
        115

<210> SEQ ID NO 21
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Ser Ser Gly Tyr Ser Gly Tyr Phe Asp Tyr Trp Gly
            100                 105                 110

Gln Gly Thr Leu Val Thr Val Ser Ser
        115                 120

<210> SEQ ID NO 22
<211> LENGTH: 117
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 22

Asp Val Val Met Thr Gln Ser Pro Leu Ser Leu Pro Val Thr Pro Gly
1               5                   10                  15

Glu Pro Ala Ser Ile Ser Cys Arg Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Ala
                85                  90                  95

Leu Gln Thr Pro Pro Tyr Thr Phe Gly Gln Gly Thr Lys Leu Glu Ile
            100                 105                 110

Lys Arg Thr Val Ala
            115

<210> SEQ ID NO 23
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65              70                  75                  80

Met Glu Leu Ser Arg Leu Arg Ser Asp Asp Thr Ala Val Tyr Tyr Cys
                85                  90                  95

Ala Arg Asp Leu Ser Ser Gly Tyr Ser Gly Tyr Phe Asp Tyr Trp Gly
            100                 105                 110

Gln Gly Thr Leu Val Thr Val Ser Ser
            115                 120

<210> SEQ ID NO 24
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Val Val Met Thr Gln Ser Pro Leu Ser Leu Pro Val Thr Pro Gly
1               5                   10                  15
```

```
Glu Pro Ala Ser Ile Ser Cys Arg Ser Ser Gln Ser Leu Leu His Ser
            20                  25                  30

Asn Gly Tyr Asn Tyr Leu Asn Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Gly Glu Asp Val Gly Tyr Tyr Cys Met Gln Ala
                85                  90                  95

Leu Gln Ser Pro Phe Thr Phe Gly Gln Gly Thr Lys Leu Glu Ile Lys
            100                 105                 110

Arg Thr Val Ala
        115
```

<210> SEQ ID NO 25
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Ser Ser Gly Tyr Gly Tyr Phe Asp Tyr Trp Gly
            100                 105                 110

Gln Gly Thr Leu Val Thr Val Ser Ser
        115                 120
```

<210> SEQ ID NO 26
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Phe Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Asp Asp Val Gly Val Tyr Tyr Cys Met Gln Ser
                 85                  90                  95

Leu Gln Thr Pro Trp Thr Phe Gly His Gly Thr Lys Val Glu Ile Lys
            100                 105                 110

Arg Thr Val Ala
        115
```

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Gly Gly Gly Gly Ser Gly Gly Gly Gly Ser Gly Gly Gly Gly Ser
 1               5                  10                  15
```

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggcggcggcg gatctggagg tggtggctca ggtggcggag gctcc              45

<210> SEQ ID NO 29
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
caagtacagc tccaacagtc aggacccggt ctcgttaaac cttcccaaac gctgtccctc     60
acttgcgcca tcagcggaga ttccgtgagc tctaactctg ccgcttggaa ctggattagg    120
caatccccct cccgaggact ggaatggctg ggaagaactt actaccgctc caaatggtac    180
aacgactacg cagtgtccgt caagtctcga atcactatca accctgacac aagcaaaaat    240
cagttttccc tgcaactcaa ctcagtcacc cctgaggaca cggcggttta ctattgcgct    300
agagagaata ttgccgcatg gacctgggcg ttcgatatat ggggtcaggg aacaatggta    360
accgtcagct cc                                                        372

<210> SEQ ID NO 30
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gaaatcgtta tgacacagtc ccctggaaca ctctccctgt cctggtga aagagctact       60 ctgtcctgcc gcgctagtca atccgtatcc tcctcctacc ttgcttggta ccaacaaaag    120

```
cccggacttg ccccacgcct ccttatttac gacacctcac tccgcgcaac agatatccca    180
gatagattct ccggatcagg ctccgggacc gcttttacac tgacaatttc taggctcgaa    240
ccagaggact tcgctgtata ttactgccaa cagtatggct cttcaccaac attcggacaa    300
ggcaccaaag tcgaaatcaa acgcaccgta gcc                                 333
```

<210> SEQ ID NO 31
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
gaagttcagc tcgtccagtc cggcgctgag gtcaagaagc ccgggtcatc cgtgaaagtc    60
agttgtaaag ctagcggagg tacatttacg ggatattaca tgcattgggt gcggcaggcg    120
ccaggccaag gactcgaatg gatgggatgg atcaatccca actcaggcgg aacaaattat    180
gctcagaaat tccagggtag agtgactatg actcgggata ctagcatcag cacagcatac    240
atggaactgt cacggctgcg atccgacgac actgcagtgt actattgcgc cagggacctc    300
tcttcaggat actcaggtta cttcgactac tggggacaag gcacactcgt gactgtatct    360
agc                                                                  363
```

<210> SEQ ID NO 32
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
gacgtggtta tgacccaatc ccctctctct ctccctgtga ccctggaga acccgcttca     60 atctcatgtc gctcatctca atcactgctt cattccaatg gatacaatta cctcgattgg    120
tatcttcaaa agcccggcca gtcccctcaa ctgcttatct atctcggctc caatagagca    180
tcaggcgtgc ccgatcgatt ttccggctca ggctccggca cagatttac tctgaaaatt     240 agtagagttg aggcagaaga tgtgggtgtc tattattgca tgcaagctct gcagaccctc    300
acatttggac agggaacacg cctggaaatt aaacgcacag tcgcc                    345
```

<210> SEQ ID NO 33
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
gaagtacaat tggttcaatc cggggcggaa gtcaagaaac caggatctag tgtgaaagtc    60
agttgcaaag catctggagg gacattcaca ggttattaca tgcactgggt tagacaggcc    120
cctgggcaag gacttgaatg gatgggctgg ataaacccta atagcggagg aacaaattat    180
gctcaaaaat tccaagggag agttacaatg actcgagaca cttctatcag cactgcctat    240
atggaactca gcaggctccg ctccgacgac actgcggtat attattgtgc tagagatctc    300
agctccgggt atagtggtta ttttgattac tggggacagg gcactctcgt tactgtgtca    360
``` tca                                                                    363

<210> SEQ ID NO 34
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gatgtcgtga tgacccaatc cccactgtcc ctccctgtaa ccccaggaga acctgcatca    60
atatcttgtc gatcctcaca atctcttctg cactcaaacg gttataatta tcttgattgg   120
tatctccaaa agccagggca aagtccacag cttcttattt acctcggcag taatagagct   180
tcaggtgttc ccgatagatt tagtggcagc ggatctggta ctgactttac ccttaaaatt   240
tcccgagtgg aggccgaaga tgttggagtc tactactgca tgcaggcact gcaaacccca   300
ccatacactt tcggtcaagg tacgaagctt gaaattaaac gaaccgtagc a            351

<210> SEQ ID NO 35
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gaagttcagc tcgtccagtc cggcgctgag gtcaagaagc ccgggtcatc cgtgaaagtc    60
agttgtaaag ctagcggagg tacatttacg ggatattaca tgcattgggt gcggcaggcg   120
ccaggccaag gactcgaatg gatgggatgg atcaatccca actcaggcgg aacaaattat   180
gctcagaaat tccagggtag agtgactatg actcgggata ctagcatcag cacagcatac   240
atggaactgt cacggctgcg atccgacgac actgcagtgt actattgcgc cagggacctc   300
tcttcaggat actcaggtta cttcgactac tggggacaag gcacactcgt gactgtatct   360
agc                                                                  363

<210> SEQ ID NO 36
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gatgttgtta tgacccagag ccctttgtcc ctccctgtaa ccccaggtga acccgcaagc    60
atttcatgta gatcttctca atctcttctt cacagcaatg gctataatta cttgaattgg   120
tatctccaga agcccggtca gtcccctcaa cttcttatct acttgggatc taaccgcgca   180
tccggcgtgc ccgatcgatt ttccggatca ggcagcggca cagactttac actcaaaatc   240
tctagagtgg aaggcgaaga tgtgggcgac tattactgta tgcaggcttt gcaatccccc   300
ttcacctttg ggcagggtac taaacttgaa atcaaagaa ccgtagcc                 348

<210> SEQ ID NO 37
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
gaagtacagt tggtccaaag cggcgcagaa gttaagaaac caggctcctc agttaaagtc    60
tcatgtaaag catccggcgg cactttcaca gggtactata tgcattgggt cagacaagca   120
ccaggacaag gcctcgaatg gatgggttgg attaatccta attccggtgg aacgaactat   180
gcacagaaat tcaaggacg cgtaacgatg acacgagaca caagtatatc aacagcttat    240
atggaactca gcagattgcg atcagacgac acggcagtat actattgcgc tcgagatctc   300
tcctctggct attcaggata cttcgattat tggggacagg gcactctcgt cacagtttct   360
tct                                                                363
```

<210> SEQ ID NO 38
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
gatgtggtaa tgactcaaag tcctttgtcc cttcctgtga cccctggaga acctgcctca    60
atttcctgta gatcttctca aagtcttctt cactccaatg gatataattt tcttgattgg   120
tatcttcaaa aacccggaca gtccccacag ttgctcattt acctgggttc taatcgagcc   180
tccggcgtcc cagacaggtt ttcaggttca ggcagtggta ccgatttcac acttaagatt   240
tctcgcgtcg aagccgatga tgtaggcgtt tattattgta tgcaatccct tcagactcct   300
tggactttcg gtcatggaac gaaagtagaa attaaacgaa cagttgca                348
```

<210> SEQ ID NO 39
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Asn Ile Ala Ala Trp Thr Trp Ala Phe Asp
            100                 105                 110

Ile Trp Gly Gln Gly Thr Met Val Thr Val Ser Ser Gly Gly Gly Gly
        115                 120                 125

Ser Gly Gly Gly Gly Ser Gly Gly Gly Gly Ser Glu Ile Val Met Thr
```

```
            130                 135                 140
Gln Ser Pro Gly Thr Leu Ser Leu Ser Pro Gly Glu Arg Ala Thr Leu
145                 150                 155                 160

Ser Cys Arg Ala Ser Gln Ser Val Ser Ser Tyr Leu Ala Trp Tyr
                165                 170                 175

Gln Gln Lys Pro Gly Leu Ala Pro Arg Leu Leu Ile Tyr Asp Thr Ser
                180                 185                 190

Leu Arg Ala Thr Asp Ile Pro Asp Arg Phe Ser Gly Ser Gly Ser Gly
                195                 200                 205

Thr Ala Phe Thr Leu Thr Ile Ser Arg Leu Glu Pro Glu Asp Phe Ala
210                 215                 220

Val Tyr Tyr Cys Gln Gln Tyr Gly Ser Ser Pro Thr Phe Gly Gln Gly
225                 230                 235                 240

Thr Lys Val Glu Ile Lys Arg Thr Val Ala
                245                 250

<210> SEQ ID NO 40
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Ser Ser Gly Tyr Ser Gly Tyr Phe Asp Tyr Trp Gly
                100                 105                 110

Gln Gly Thr Leu Val Thr Val Ser Ser Gly Gly Gly Ser Gly Gly
                115                 120                 125

Gly Gly Ser Gly Gly Gly Ser Asp Val Val Met Thr Gln Ser Pro
                130                 135                 140

Leu Ser Leu Pro Val Thr Pro Gly Glu Pro Ala Ser Ile Ser Cys Arg
145                 150                 155                 160

Ser Ser Gln Ser Leu Leu His Ser Asn Gly Tyr Asn Tyr Leu Asp Trp
                165                 170                 175

Tyr Leu Gln Lys Pro Gly Gln Ser Pro Gln Leu Leu Ile Tyr Leu Gly
                180                 185                 190

Ser Asn Arg Ala Ser Gly Val Pro Asp Arg Phe Ser Gly Ser Gly Ser
                195                 200                 205

Gly Thr Asp Phe Thr Leu Lys Ile Ser Arg Val Glu Ala Glu Asp Val
                210                 215                 220

Gly Val Tyr Tyr Cys Met Gln Ala Leu Gln Thr Leu Thr Phe Gly Gln
225                 230                 235                 240
```

```
Gly Thr Arg Leu Glu Ile Lys Arg Thr Val Ala
                245                 250
```

<210> SEQ ID NO 41
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Ser Ser Gly Tyr Ser Gly Tyr Phe Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Val Val Met Thr Gln Ser Pro
    130                 135                 140

Leu Ser Leu Pro Val Thr Pro Gly Glu Pro Ala Ser Ile Ser Cys Arg
145                 150                 155                 160

Ser Ser Gln Ser Leu Leu His Ser Asn Gly Tyr Asn Tyr Leu Asp Trp
                165                 170                 175

Tyr Leu Gln Lys Pro Gly Gln Ser Pro Gln Leu Leu Ile Tyr Leu Gly
            180                 185                 190

Ser Asn Arg Ala Ser Gly Val Pro Asp Arg Phe Ser Gly Ser Gly Ser
        195                 200                 205

Gly Thr Asp Phe Thr Leu Lys Ile Ser Arg Val Glu Ala Glu Asp Val
    210                 215                 220

Gly Val Tyr Tyr Cys Met Gln Ala Leu Gln Thr Pro Pro Tyr Thr Phe
225                 230                 235                 240

Gly Gln Gly Thr Lys Leu Glu Ile Lys Arg Thr Val Ala
                245                 250
```

<210> SEQ ID NO 42
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Gly Tyr
            20                  25                  30
```

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Ser Ser Gly Tyr Ser Gly Tyr Phe Asp Tyr Trp Gly
                100                 105                 110

Gln Gly Thr Leu Val Thr Val Ser Ser Gly Gly Gly Ser Gly Gly
            115                 120                 125

Gly Gly Ser Gly Gly Gly Ser Asp Val Val Met Thr Gln Ser Pro
            130                 135                 140

Leu Ser Leu Pro Val Thr Pro Gly Glu Pro Ala Ser Ile Ser Cys Arg
145                 150                 155                 160

Ser Ser Gln Ser Leu Leu His Ser Asn Gly Tyr Asn Tyr Leu Asn Trp
                165                 170                 175

Tyr Leu Gln Lys Pro Gly Gln Ser Pro Gln Leu Leu Ile Tyr Leu Gly
                180                 185                 190

Ser Asn Arg Ala Ser Gly Val Pro Asp Arg Phe Ser Gly Ser Gly Ser
                195                 200                 205

Gly Thr Asp Phe Thr Leu Lys Ile Ser Arg Val Glu Gly Glu Asp Val
            210                 215                 220

Gly Asp Tyr Tyr Cys Met Gln Ala Leu Gln Ser Pro Phe Thr Phe Gly
225                 230                 235                 240

Gln Gly Thr Lys Leu Glu Ile Lys Arg Thr Val Ala
                245                 250

<210> SEQ ID NO 43
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Ser Ser Gly Tyr Ser Gly Tyr Phe Asp Tyr Trp Gly
                100                 105                 110

Gln Gly Thr Leu Val Thr Val Ser Ser Gly Gly Gly Ser Gly Gly
            115                 120                 125

Gly Gly Ser Gly Gly Gly Ser Asp Val Val Met Thr Gln Ser Pro
            130                 135                 140

Leu Ser Leu Pro Val Thr Pro Gly Glu Pro Ala Ser Ile Ser Cys Arg
145                 150                 155                 160

Ser Ser Gln Ser Leu Leu His Ser Asn Gly Tyr Asn Phe Leu Asp Trp
            165                 170                 175

Tyr Leu Gln Lys Pro Gly Gln Ser Pro Gln Leu Leu Ile Tyr Leu Gly
            180                 185                 190

Ser Asn Arg Ala Ser Gly Val Pro Asp Arg Phe Ser Gly Ser Gly Ser
        195                 200                 205

Gly Thr Asp Phe Thr Leu Lys Ile Ser Arg Val Glu Ala Asp Asp Val
        210                 215                 220

Gly Val Tyr Tyr Cys Met Gln Ser Leu Gln Thr Pro Trp Thr Phe Gly
225                 230                 235                 240

His Gly Thr Lys Val Glu Ile Lys Arg Thr Val Ala
                245                 250

```
<210> SEQ ID NO 44
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44
```

Thr Ala Met Ala Leu Pro Val Thr Ala Leu Leu Leu Pro Leu Ala Leu
1               5                   10                  15

Leu Leu His Ala Ala Arg Pro
                20

```
<210> SEQ ID NO 45
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
```
actgccatgg ccctgccagt aacggctctg ctgctgccac ttgctctgct cctccatgca     60
gccaggcct                                                            69

```
<210> SEQ ID NO 46
<211> LENGTH: 220
<212> TYPE: PRT
<213> ORGANISM: Homo sapiens

<400> SEQUENCE: 46
```

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

```
Phe Tyr Leu Gln Asn Leu Tyr Val Asn Gln Thr Asp Ile Tyr Phe Cys
                100                 105                 110

Lys Ile Glu Val Met Tyr Pro Pro Tyr Leu Asp Asn Glu Lys Ser
            115                 120                 125

Asn Gly Thr Ile Ile His Val Lys Gly Lys His Leu Cys Pro Ser Pro
        130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
                180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
            210                 215                 220

<210> SEQ ID NO 47
<211> LENGTH: 321
<212> TYPE: DNA
<213> ORGANISM: Homo sapiens

<400> SEQUENCE: 47
attgaagtta tgtatcctcc tccttaccta gacaatgaga gagcaatgg aaccattatc      60 catgtgaaag ggaaacacct tgtccaagt cccctatttc ccggaccttc taagcccttt    120
tgggtgctgg tggtggttgg tggagtcctg gcttgctata gcttgctagt aacagtggcc    180
tttattattt tctgggtgag gagtaagagg agcaggctcc tgcacagtga ctacatgaac    240
atgactcccc gccgccccgg gcccacccgc aagcattacc agccctatgc cccaccacgc    300
gacttcgcag cctatcgctc c                                             321

<210> SEQ ID NO 48
<211> LENGTH: 164
<212> TYPE: PRT
<213> ORGANISM: Homo sapiens

<400> SEQUENCE: 48

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
130                 135                 140
```

```
Leu Ser Thr Ala Thr Lys Asp Thr Tyr Asp Ala Leu His Met Gln Ala
145                 150                 155                 160

Leu Pro Pro Arg

<210> SEQ ID NO 49
<211> LENGTH: 337
<212> TYPE: DNA
<213> ORGANISM: Homo sapiens

<400> SEQUENCE: 49
agagtgaagt tcagcaggag cgcagagccc cccgcgtacc agcagggcca gaaccagctc      60
tataacgagc tcaatctagg acgaagagag gagtacgatg ttttggacaa gagacgtggc     120
cgggaccctg agatggggg aaagccgaga aggaagaacc ctcaggaagg cctgtacaat     180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgcg                             337

<210> SEQ ID NO 50
<211> LENGTH: 255
<212> TYPE: PRT
<213> ORGANISM: Homo sapiens

<400> SEQUENCE: 50

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240
```

```
Cys Ser Cys Arg Phe Pro Glu Glu Glu Gly Gly Cys Glu Leu
                245                 250                 255
```

<210> SEQ ID NO 51
<211> LENGTH: 277
<212> TYPE: PRT
<213> ORGANISM: Homo sapiens

<400> SEQUENCE: 51

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
                100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275
```

<210> SEQ ID NO 52
<211> LENGTH: 199
<212> TYPE: PRT
<213> ORGANISM: Homo sapiens

<400> SEQUENCE: 52

```
Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
                20                  25                  30
```

```
Phe His Asn Gly Gly Val Gln Ile Leu Cys Lys Tyr Pro Asp Ile Val
         35                  40                  45

Gln Gln Phe Lys Met Gln Leu Leu Lys Gly Gly Gln Ile Leu Cys Asp
 50                  55                  60

Leu Thr Lys Thr Lys Gly Ser Gly Asn Thr Val Ser Ile Lys Ser Leu
 65                  70                  75                  80

Lys Phe Cys His Ser Gln Leu Ser Asn Asn Ser Val Ser Phe Phe Leu
                 85                  90                  95

Tyr Asn Leu Asp His Ser His Ala Asn Tyr Tyr Phe Cys Asn Leu Ser
            100                 105                 110

Ile Phe Asp Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
            195

<210> SEQ ID NO 53
<211> LENGTH: 223
<212> TYPE: PRT
<213> ORGANISM: Homo sapiens

<400> SEQUENCE: 53

Met Ala Cys Leu Gly Phe Gln Arg His Lys Ala Gln Leu Asn Leu Ala
 1               5                  10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
             35                  40                  45

Ser Ser Arg Gly Ile Ala Ser Phe Val Cys Glu Tyr Ala Ser Pro Gly
 50                  55                  60

Lys Ala Thr Glu Val Arg Val Thr Val Leu Arg Gln Ala Asp Ser Gln
 65                  70                  75                  80

Val Thr Glu Val Cys Ala Ala Thr Tyr Met Met Gly Asn Glu Leu Thr
                 85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Leu Gly Ile Gly
        130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
            195                 200                 205
```

```
Pro Glu Cys Glu Lys Gln Phe Gln Pro Tyr Phe Ile Pro Ile Asn
    210                 215                 220

<210> SEQ ID NO 54
<211> LENGTH: 288
<212> TYPE: PRT
<213> ORGANISM: Homo sapiens

<400> SEQUENCE: 54

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 55
<211> LENGTH: 525
<212> TYPE: PRT
<213> ORGANISM: Homo sapiens

<400> SEQUENCE: 55

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30
```

```
Trp Ala Gln Glu Gly Ala Pro Ala Gln Leu Pro Cys Ser Pro Thr Ile
         35                  40                  45

Pro Leu Gln Asp Leu Ser Leu Leu Arg Arg Ala Gly Val Thr Trp Gln
 50                  55                  60

His Gln Pro Asp Ser Gly Pro Pro Ala Ala Pro Gly His Pro Leu
 65                  70                  75                  80

Ala Pro Gly Pro His Pro Ala Ala Pro Ser Ser Trp Gly Pro Arg Pro
                 85                  90                  95

Arg Arg Tyr Thr Val Leu Ser Val Gly Pro Gly Leu Arg Ser Gly
                100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
        130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445
```

```
His Leu Leu Phe Leu Ile Leu Gly Val Leu Ser Leu Leu Leu Leu
        450                 455                 460

Val Thr Gly Ala Phe Gly Phe His Leu Trp Arg Arg Gln Trp Arg Pro
465             470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Pro Glu Gln Leu
        515                 520                 525
```

<210> SEQ ID NO 56
<211> LENGTH: 370
<212> TYPE: PRT
<213> ORGANISM: Homo sapiens

<400> SEQUENCE: 56

```
Met Leu Gly Gln Val Val Thr Leu Ile Leu Leu Leu Leu Lys Val
1               5                   10                  15

Tyr Gln Gly Lys Gly Cys Gln Gly Ser Ala Asp His Val Val Ser Ile
                20                  25                  30

Ser Gly Val Pro Leu Gln Leu Gln Pro Asn Ser Ile Gln Thr Lys Val
            35                  40                  45

Asp Ser Ile Ala Trp Lys Lys Leu Leu Pro Ser Gln Asn Gly Phe His
50                  55                  60

His Ile Leu Lys Trp Glu Asn Gly Ser Leu Pro Ser Asn Thr Ser Asn
65                  70                  75                  80

Asp Arg Phe Ser Phe Ile Val Lys Asn Leu Ser Leu Ile Lys Ala
                85                  90                  95

Ala Gln Gln Gln Asp Ser Gly Leu Tyr Cys Leu Glu Val Thr Ser Ile
                100                 105                 110

Ser Gly Lys Val Gln Thr Ala Thr Phe Gln Val Phe Val Phe Glu Ser
            115                 120                 125

Leu Leu Pro Asp Lys Val Glu Lys Pro Arg Leu Gln Gly Gln Gly Lys
130                 135                 140

Ile Leu Asp Arg Gly Arg Cys Gln Val Ala Leu Ser Cys Leu Val Ser
145                 150                 155                 160

Arg Asp Gly Asn Val Ser Tyr Ala Trp Tyr Arg Gly Ser Lys Leu Ile
                165                 170                 175

Gln Thr Ala Gly Asn Leu Thr Tyr Leu Asp Glu Glu Val Asp Ile Asn
            180                 185                 190

Gly Thr His Thr Tyr Thr Cys Asn Val Ser Asn Pro Val Ser Trp Glu
        195                 200                 205

Ser His Thr Leu Asn Leu Thr Gln Asp Cys Gln Asn Ala His Gln Glu
    210                 215                 220

Phe Arg Phe Trp Pro Phe Leu Val Ile Ile Val Ile Leu Ser Ala Leu
225                 230                 235                 240

Phe Leu Gly Thr Leu Ala Cys Phe Cys Val Trp Arg Arg Lys Arg Lys
                245                 250                 255

Glu Lys Gln Ser Glu Thr Ser Pro Lys Glu Phe Leu Thr Ile Tyr Glu
            260                 265                 270

Asp Val Lys Asp Leu Lys Thr Arg Arg Asn His Glu Gln Glu Gln Thr
        275                 280                 285

Phe Pro Gly Gly Gly Ser Thr Ile Tyr Ser Met Ile Gln Ser Gln Ser
    290                 295                 300
```

Ser Ala Pro Thr Ser Gln Glu Pro Ala Tyr Thr Leu Tyr Ser Leu Ile
305                 310                 315                 320

Gln Pro Ser Arg Lys Ser Gly Ser Arg Lys Arg Asn His Ser Pro Ser
            325                 330                 335

Phe Asn Ser Thr Ile Tyr Glu Val Ile Gly Lys Ser Gln Pro Lys Ala
            340                 345                 350

Gln Asn Pro Ala Arg Leu Ser Arg Lys Glu Leu Glu Asn Phe Asp Val
            355                 360                 365

Tyr Ser
    370

<210> SEQ ID NO 57
<211> LENGTH: 289
<212> TYPE: PRT
<213> ORGANISM: Homo sapiens

<400> SEQUENCE: 57

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
130                 135                 140

Lys Asp Glu Met Ala Ser Arg Pro Trp Leu Leu Tyr Arg Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Thr Gly
    210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Pro Asn Ser Arg Leu Ala
            260                 265                 270

Arg Asn Val Lys Glu Ala Pro Thr Glu Tyr Ala Ser Ile Cys Val Arg
        275                 280                 285

Ser

<210> SEQ ID NO 58
<211> LENGTH: 112
<212> TYPE: PRT
<213> ORGANISM: Homo sapiens

<400> SEQUENCE: 58

```
Arg Val Lys Phe Ser Arg Ser Ala Glu Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 59
<211> LENGTH: 16
<212> TYPE: PRT
<213> ORGANISM: Homo sapiens

<400> SEQUENCE: 59

```
Cys Ala Arg Glu Asn Ile Ala Ala Trp Thr Trp Ala Phe Asp Ile Trp
1               5                   10                  15
```

<210> SEQ ID NO 60
<211> LENGTH: 235
<212> TYPE: PRT
<213> ORGANISM: Homo sapiens

<400> SEQUENCE: 60

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
130                 135                 140

Pro Pro Thr Pro Ala Pro Thr Ile Ala Ser Gln Pro Leu Ser Leu Arg
145                 150                 155                 160
```

-continued

```
Pro Glu Ala Cys Arg Pro Ala Ala Gly Gly Ala Val His Thr Arg Gly
                165             170             175

Leu Asp Phe Ala Cys Asp Ile Tyr Ile Trp Ala Pro Leu Ala Gly Thr
            180             185             190

Cys Gly Val Leu Leu Leu Ser Leu Val Ile Thr Leu Tyr Cys Asn His
        195             200             205

Arg Asn Arg Arg Arg Val Cys Lys Cys Pro Arg Pro Val Val Lys Ser
    210             215             220

Gly Asp Lys Pro Ser Leu Ser Ala Arg Tyr Val
225             230             235
```

ANTIGEN-BINDING PROTEINS TARGETING CD56 AND USES THEREOF

CROSS-REFERENCE TO RELATED APPLICATIONS

This application a Continuation of International Patent Application No. PCT/US2016/045027, filed Aug. 1, 2016, which claims priority to U.S. Provisional Patent Application Ser. No. 62/199,775, filed Jul. 31, 2015, the contents of each of which are hereby incorporated by reference in their entirety herein, and to each of which priority is claimed.

SEQUENCE LISTING

The specification further incorporates by reference the Sequence Listing submitted herewith via EFS on Jan. 30, 2018. Pursuant to 37 C.F.R. § 1.52(e)(5), the Sequence Listing text file, identified as 0727340661SL.txt, is 63,861 bytes and was created on Jan. 30, 2018. The entire contents of the Sequence Listing are hereby incorporated by reference. The Sequence Listing does not extend beyond the scope of the specification and thus does not contain new matter.

INTRODUCTION

The presently disclosed subject matter provides for methods and compositions for treating cancer. It relates to antigen-binding proteins that include antibodies, or antigen-binding portions thereof, and chimeric antigen receptors (CARs) that specifically target CD56. The presently disclosed subject matter further includes immunoresponsive cells comprising such CARs, and methods of using such cells for treating cancers (e.g., multiple myeloma).

BACKGROUND OF THE INVENTION

Cell-based immunotherapy is a therapy with curative potential for the treatment of cancer. T cells and other immune cells may be modified to target tumor antigens through the introduction of genetic material coding for artificial or synthetic receptors for antigen, termed Chimeric Antigen Receptors (CARs), specific to selected antigens. Targeted T cell therapy using CARs has shown recent clinical success in treating hematologic malignancies.

Multiple Myeloma, the second most common hematological malignancy, remains incurable despite recent advances in treatment protocols incorporating the immunomodulatory drugs (IMiDs) lenalidomide, and pomalidomide as well as the proteosomal inhibitors bortezomib and carfilzomib. A number of immunotherapeutic strategies are therefore being actively investigated in myeloma with the aim of improving disease-free survival. The evidence that myeloma is amenable to immunotherapy comes from the clinical experience of treating myeloma patients with allogeneic hematopoietic stem cell transplantation where a graft versus myeloma effect has been demonstrated in high risk patients (Krishnan, et al. Autologous haemopoietic stem-cell transplantation followed by allogeneic or autologous haemopoietic stem-cell transplantation in patients with multiple myeloma (BMT CTN 0102): a phase 3 biological assignment trial. *Lancet Oncol.* 12:1195-1203 (2011)) and from the use of donor lymphocyte infusions where response rates of up to 30-40% have been seen (Lokhorst, et al. Donor lymphocyte infusions for relapsed multiple myeloma after allogeneic stem-cell transplantation: predictive factors for response and long-term outcome. *J. Clin. Oncol.* 18:3031-3037 (2000); Salama, et al. Donor leukocyte infusions for multiple myeloma. *Bone Marrow Transplant.* 26:1179-1184 (2000)). Further supporting evidence comes from the successful therapeutic use of the IMiDs and from the promising results of clinical trials using monoclonal antibodies directed against the myeloma associated tumor antigens CS-1, CD38, CD56 and CD138 (Kaufman, et al. Elotuzumab in Combination With Lenalidomide and Low-Dose Dexamethasone in Relapsed or Refractory Multiple Myeloma. *J. Clin. Oncol.* 30:1953-1959 (2012)).

The neural cell adhesion molecule CD56 is one of the most frequently expressed antigens in myeloma and therefore a potential target for CAR immunotherapy. CD56 plays an important role in tumorigenesis by mediating cell-cell adhesion, thereby facilitating the interaction of myeloma cells with bone marrow stromal cells, as well as by promoting tumor cell migration, invasion and proliferation and inhibiting apoptosis (Gattenloehner, et al. Novel RUNX1 isoforms determine the fate of acute myeloid leukemia cells by controlling CD56 expression. *Blood.* 110:2027-2033 (2007)). CD56 is expressed normally on natural killer cells, a subset of T lymphocytes, neuroendocrine tissue and in the brain where its expression peaks during embryogenesis but remains expressed at low levels even in the adult brain. Importantly, it is uniformly expressed at a significantly higher density in over 70% of patients with myeloma (Tassone, et al. In vitro and in vivo activity of the maytansinoid immunoconjugate huN901-N2'-deacetyl-N2'-(3-mercapto-1-oxopropyl)-maytansine against CD56+ multiple myeloma cells. *Cancer Res.* 64:4629-4636 (2004)).

There has been emerging interest in cellular immunotherapy using T cells expressing either T cell receptors (TCRs) or CARs targeted against myeloma associated antigens following the successful use of CD19 targeted CARs in patients with chronic lymphocytic leukemia and acute lymphoblastic leukemia (Brentjens, R. J., et al. Eradication of systemic B-cell tumors by genetically targeted human T lymphocytes co-stimulated by CD80 and interleukin-15. *Nature medicine* 9, 279-286 (2003); Brentjens, R. J., et al. CD19-Targeted T Cells Rapidly Induce Molecular Remissions in Adults with Chemotherapy-Refractory Acute Lymphoblastic Leukemia. *Science translational medicine* 5, 177ra138 (2013); Porter, et al. Chimeric antigen receptor-modified T cells in chronic lymphoid leukemia. *N. Engl. J. Med.* 365:725-733 (2011)). While there are various reasons to expect that adoptive T cell therapy may work well in multiple myeloma, expanding adoptive T cell therapy to myeloma also poses unique challenges. Unlike other B-cell malignancies, CD19 expression is seen in only 2% of myeloma patients (Bataille, R., et al. The phenotype of normal, reactive and malignant plasma cells. Identification of "many and multiple myelomas" and of new targets for myeloma therapy. *Haematologica* 91, 1234-1240 (2006)). Furthermore, unlike CD19, the common extracellular immunophenotypic markers in myeloma (CD138, CD38, and CD56) are all co-expressed on other essential cell types, and it is predicted that CARs to any of these targets would lead to unacceptable "off tumor, on target" toxicity (Brentjens (2013)) which can be fatal even in targets where antibodies are well tolerated, as was the case with a HER2 targeted CAR (Morgan, R. A., et al. Case report of a serious adverse event following the administration of T cells transduced with a chimeric antigen receptor recognizing ERBB2. *Molecular therapy: the journal of the American Society of Gene Therapy* 18, 843-851 (2010)). Accordingly, there are needs for novel therapeutic strategies to design CARs targeting antigens that are highly expressed in multiple myeloma cells and limited expression in normal tissues for treating multiple myeloma, and for strategies capable of inducing potent tumor eradication with minimal toxicity and immunogenicity.

SUMMARY OF THE INVENTION

The presently disclosed subject matter generally provides antigen-binding proteins that include antibodies, or antigen-binding portions thereof, and chimeric antigen receptors (CARs) that specifically target CD56, immunoresponsive cells comprising such CARs, and uses of these antibodies, or antigen-binding portions thereof, CARs and immunoresponsive cells for treating cancers.

The presently disclosed subject matter provides CARs comprising an extracellular antigen-binding domain, a transmembrane domain and an intracellular domain, where the extracellular antigen-binding domain cross-competes for binding to human CD56 with a reference antibody or an antigen-binding portion thereof comprising a heavy chain variable region CDR1 comprising amino acids having the sequence set forth in SEQ ID NO: 1; a heavy chain variable region CDR2 comprising amino acids having the sequence set forth in SEQ ID NO: 2; a heavy chain variable region CDR3 comprising amino acids having the sequence set forth in SEQ ID NO: 3 or SEQ ID NO: 59; a light chain variable region CDR1 comprising amino acids having the sequence set forth in SEQ ID NO: 4; a light chain variable region CDR2 comprising amino acids having the sequence set forth in SEQ ID NO:5; and a light chain variable region CDR3 comprising amino acids having the sequence set forth in SEQ ID NO:6. In certain embodiments, the extracellular antigen-binding domain reduces binding of the reference antibody or antigen-binding portion thereof to human CD56 by at least about 20%.

The presently disclosed subject matter also provides CARs comprising an extracellular antigen-binding domain, a transmembrane domain and an intracellular domain, where the extracellular antigen-binding domain binds to the same epitope on human CD56 as a reference antibody or an antigen-binding portion thereof comprising a heavy chain variable region CDR1 comprising amino acids having the sequence set forth in SEQ ID NO:1; a heavy chain variable region CDR2 comprising amino acids having the sequence set forth in SEQ ID NO:2; a heavy chain variable region CDR3 comprising amino acids having the sequence set forth in SEQ ID NO:3 or SEQ ID NO: 59; a light chain variable region CDR1 comprising amino acids having the sequence set forth in SEQ ID NO: 4; a light chain variable region CDR2 comprising amino acids having the sequence set forth in SEQ ID NO:5; and a light chain variable region CDR3 comprising amino acids having the sequence set forth in SEQ ID NO:6.

In certain embodiments, the reference antibody or antigen-binding portion thereof comprises a heavy chain variable region comprising amino acids having the sequence set forth in SEQ ID NO:7, and a light chain variable region comprising amino acids having the sequence set forth in SEQ ID NO:8.

Furthermore, the presently disclosed subject matter provides CARs comprising an extracellular antigen-binding domain, a transmembrane domain and an intracellular domain, wherein the extracellular antigen-binding domain specifically binds to human CD56 with a binding affinity ($K_d$) of about $3 \times 10^{-9}$ or less. In certain embodiments, the extracellular antigen-binding domain comprises a heavy chain variable region CDR1 comprising amino acids having the sequence set forth in SEQ ID NO:1; a heavy chain variable region CDR2 comprising amino acids having the sequence set forth in SEQ ID NO: 2; and a heavy chain variable region CDR3 comprising amino acids having the sequence set forth in SEQ ID NO:3 or SEQ ID NO: 59. In certain embodiments, the extracellular antigen-binding domain comprises a light chain variable region CDR1 comprising amino acids having the sequence set forth in SEQ ID NO:4; a light chain variable region CDR2 comprising amino acids having the sequence set forth in SEQ ID NO:5; and a light chain variable region CDR3 comprising amino acids having the sequence set forth in SEQ ID NO:6. In certain embodiments, the extracellular antigen-binding domain comprises a heavy chain variable region CDR3 comprising amino acids having the sequence set forth in SEQ ID NO:3, a conservative modification of SEQ ID NO: 3, SEQ ID NO: 59, or a conservative modification of of SEQ ID NO: 59, and a a light chain variable region CDR3 comprising amino acids having the sequence set forth in SEQ ID NO:6 or a conservative modification thereof. In certain embodiments, the extracellular antigen-binding domain comprises a heavy chain variable region CDR2 comprising amino acids having the sequence set forth in SEQ ID NO: 2 or a conservative modification thereof, and a light chain variable region CDR2 comprising amino acids having the sequence set forth in SEQ ID NO: 5 or a conservative modification thereof. In certain embodiments, the extracellular antigen-binding domain comprises a heavy chain variable region CDR1 comprising amino acids having the sequence set forth in SEQ ID NO: 1 or a conservative modification thereof, and a light chain variable region CDR1 comprising amino acids having the sequence set forth in SEQ ID NO: 4. In certain embodiments, the extracellular antigen-binding domain comprises a heavy chain variable region CDR1 comprising amino acids having the sequence set forth in SEQ ID NO: 1; a heavy chain variable region CDR2 comprising amino acids having the sequence set forth in SEQ ID NO: 2; a heavy chain variable region CDR3 comprising amino acids having the sequence set forth in SEQ ID NO: 3 or SEQ ID NO: 59; a light chain variable region CDR1 comprising amino acids having the sequence set forth in SEQ ID NO: 4; a light chain variable region CDR2 comprising amino acids having the sequence set forth in SEQ ID NO: 5; and a light chain variable region CDR3 comprising amino acids having the sequence set forth in SEQ ID NO: 6. In certain embodiments, the extracellular antigen-binding domain comprises a heavy chain variable region comprising an amino acid sequence that is at least about 80% homologous to SEQ ID NO:7. In certain embodiments, the extracellular antigen-binding domain comprises a heavy chain variable region comprising amino acids having the sequence set forth in SEQ ID NO:7. In certain embodiments, the extracellular antigen-binding domain comprises a light chain variable region comprising an amino acid sequence that is at least about 80% homologous to SEQ ID NO:8. In certain embodiments, wherein the extracellular antigen-binding domain comprises a light chain variable region comprising amino acids having the sequence set forth in SEQ ID NO:8. In certain embodiments, the extracellular antigen-binding domain comprises a heavy chain variable region comprising an amino acid sequence that is at least about 80% homologous to SEQ ID NO:7, and a light chain variable region comprising an amino acid sequence that is at least about 80% homologous to SEQ ID NO:8. In certain embodiments, the extracellular antigen-binding domain comprises a heavy chain variable region comprising amino acids having the sequence set forth in SEQ ID NO:7, and a light chain variable region comprising amino acids having the sequence set forth in SEQ ID NO:8.

Also provided by the presently disclosed subject matter are CARs comprising an extracellular antigen-binding domain, a transmembrane domain and an intracellular domain, wherein the extracellular antigen-binding domain specifically binds to human CD56 with a binding affinity ($K_d$) of from about $3 \times 10^{-9}$ to about $2 \times 10^{-7}$. In certain embodiments, the extracellular antigen-binding domain comprises: a heavy chain variable region CDR1 comprising amino acids having the sequence set forth in SEQ ID NO: 9; a heavy chain variable region CDR2 comprising amino acids having the sequence set forth in SEQ ID NO: 10; and a heavy chain variable region CDR3 comprising amino acids having the sequence set forth in SEQ ID NO: 11. In certain embodiments, the extracellular antigen-binding domain comprises: a light chain variable region CDR1 comprising amino acids having the sequence set forth in SEQ ID NO: 12; a light chain variable region CDR2 comprising amino acids having the sequence set forth in SEQ ID NO: 14; and a light chain variable region CDR3 comprising amino acids having the sequence set forth in SEQ ID NO: 15. In certain embodiments, the extracellular antigen-binding domain comprises: a light chain variable region CDR1 comprising amino acids having the sequence set forth in SEQ ID NO: 12; a light chain variable region CDR2 comprising amino acids having the sequence set forth in SEQ ID NO: 14; and a light chain variable region CDR3 comprising amino acids having the sequence set forth in SEQ ID NO: 16. In certain embodiments, the extracellular antigen-binding domain comprises: a light chain variable region CDR1 comprising amino acids having the sequence set forth in SEQ ID NO: 12; a light chain variable region CDR2 comprising amino acids having the sequence set forth in SEQ ID NO: 14; and a light chain variable region CDR3 comprising amino acids having the sequence set forth in SEQ ID NO: 17. In certain embodiments, the extracellular antigen-binding domain comprises: a light chain variable region CDR1 comprising amino acids having the sequence set forth in SEQ ID NO: 13; a light chain variable region CDR2 comprising amino acids having the sequence set forth in SEQ ID NO: 14; and a light chain variable region CDR3 comprising amino acids having the sequence set forth in SEQ ID NO: 18.

In certain embodiments, the extracellular antigen-binding domain comprises: a heavy chain variable region CDR3 comprising amino acids having the sequence set forth in SEQ ID NO: 11 or a conservative modification thereof; and a light chain variable region CDR3 comprising amino acids having a sequence selected from the group consisting of SEQ ID NO: 15, a conservative modification of of SEQ ID NO: 15, SEQ ID NO: 16 or a conservative modification thereof, SEQ ID NO: 17, a conservative modification of SEQ ID NO: 16, and SEQ ID NO: 18, and a conservative modification of of SEQ ID NO: 18. In certain embodiments, the extracellular antigen-binding domain comprises: a heavy chain variable region CDR2 comprising amino acids having the sequence set forth in SEQ ID NO: 10 or a conservative modification thereof; and a light chain variable region CDR2 comprising amino acids having the sequence set forth in SEQ ID NO: 14. In certain embodiments, the extracellular antigen-binding domain comprises: a heavy chain variable region CDR1 comprising amino acids having the sequence set forth in SEQ ID NO: 9 or a conservative modification thereof; and a light chain variable region CDR1 comprising amino acids having a sequence selected from the group consisting of SEQ ID NO: 12, a conservative modification of SEQ ID NO: 12, SEQ ID NO: 13, and a conservative modification of SEQ ID NO: 13.

In certain embodiments, the extracellular antigen-binding domain comprises: (a) a heavy chain variable region CDR1 comprising amino acids having the sequence set forth in SEQ ID NO: 9; a heavy chain variable region CDR2 comprising amino acids having the sequence set forth in SEQ ID NO: 10; a heavy chain variable region CDR3 comprising amino acids having the sequence set forth in SEQ ID NO: 11; a light chain variable region CDR1 comprising amino acids having the sequence set forth in SEQ ID NO: 12; a light chain variable region CDR2 comprising amino acids having the sequence set forth in SEQ ID NO: 14; and a light chain variable region CDR3 comprising amino acids having the sequence set forth in SEQ ID NO: 15;

(b) a heavy chain variable region CDR1 comprising amino acids having the sequence set forth in SEQ ID NO: 9; a heavy chain variable region CDR2 comprising amino acids having the sequence set forth in SEQ ID NO: 10; a heavy chain variable region CDR3 comprising amino acids having the sequence set forth in SEQ ID NO: 11; a light chain variable region CDR1 comprising amino acids having the sequence set forth in SEQ ID NO: 12; a light chain variable region CDR2 comprising amino acids having the sequence set forth in SEQ ID NO: 14; and a light chain variable region CDR3 comprising amino acids having the sequence set forth in SEQ ID NO: 16;

(c) a heavy chain variable region CDR1 comprising amino acids having the sequence set forth in SEQ ID NO: 9; a heavy chain variable region CDR2 comprising amino acids having the sequence set forth in SEQ ID NO: 10; a heavy chain variable region CDR3 comprising amino acids having the sequence set forth in SEQ ID NO: 11; a light chain variable region CDR1 comprising amino acids having the sequence set forth in SEQ ID NO: 12; a light chain variable region CDR2 comprising amino acids having the sequence set forth in SEQ ID NO: 14; and a light chain variable region CDR3 comprising amino acids having the sequence set forth in SEQ ID NO: 17; or (d) a heavy chain variable region CDR1 comprising amino acids having the sequence set forth in SEQ ID NO: 9; a heavy chain variable region CDR2 comprising amino acids having the sequence set forth in SEQ ID NO: 10; a heavy chain variable region CDR3 comprising amino acids having the sequence set forth in SEQ ID NO: 11; a light chain variable region CDR1 comprising amino acids having the sequence set forth in SEQ ID NO: 13; a light chain variable region CDR2 comprising amino acids having the sequence set forth in SEQ ID NO: 14; and a light chain variable region CDR3 comprising amino acids having the sequence set forth in SEQ ID NO: 18.

In certain embodiments, the extracellular antigen-binding domain comprises: a heavy chain variable region comprising an amino acid sequence that is at least about 80% homologous to SEQ ID NO: 19, SEQ ID NO: 21, SEQ ID NO: 23, or SEQ ID NO: 25. In certain embodiments, the extracellular antigen-binding domain comprises a heavy chain variable region comprising amino acids having a sequence selected from the group consisting of SEQ ID NOS: 19, 21, 23, and 25. In certain embodiments, the extracellular antigen-binding domain comprises: a light chain variable region comprising an amino acid sequence that is at least about 80% homologous to SEQ ID NO: SEQ ID NO: 20, SEQ ID NO: 22, SEQ ID NO: 24, or SEQ ID NO: 26. In certain embodiments, the extracellular antigen-binding domain comprises a light chain variable region comprising amino acids having a sequence selected from the group consisting of SEQ ID NOS: 20, 22, 24, and 26. In certain embodiments, the extracellular antigen-binding domain comprises: a heavy chain variable region comprising an amino acid sequence that is at least about 80% homologous to SEQ ID NO: 19, SEQ ID NO: 21, SEQ ID NO: 23, or SEQ ID NO: 25; and a light chain variable region comprising an amino acid sequence that is at least about 80% homologous to SEQ ID NO: 20, SEQ ID NO: 22, SEQ ID NO: 24, or SEQ ID NO: 26. In certain embodiments, the extracellular antigen-binding domain comprises: a heavy chain variable region comprising amino acids having a sequence selected from the group consisting of SEQ ID NOS: 19, 21, 23, and 25; and a light chain variable region comprising amino acids having a sequence selected from the group consisting of SEQ ID NOS: 20, 22, 24, and 26.

In certain embodiments, the extracellular antigen-binding domain comprises:

(a) a heavy chain variable region comprising amino acids having a sequence selected from the group consisting of SEQ ID NO: 19; and a light chain variable region comprising amino acids having a sequence selected from the group consisting of SEQ ID NO: 20;

(b) a heavy chain variable region comprising amino acids having a sequence selected from the group consisting of SEQ ID NO: 21; and a light chain variable region comprising amino acids having a sequence selected from the group consisting of SEQ ID NO: 22;

(c) a heavy chain variable region comprising amino acids having a sequence selected from the group consisting of SEQ ID NO: 23; and a light chain variable region comprising amino acids having a sequence selected from the group consisting of SEQ ID NO: 24; or (d) a heavy chain variable region comprising amino acids having a sequence selected from the group consisting of SEQ ID NO: 25; and a light chain variable region comprising amino acids having a sequence selected from the group consisting of SEQ ID NO: 26.

In certain non-limiting embodiments, the human scFv comprises both of said heavy and light chains, optionally with a linker sequence, for example a linker peptide, between the heavy chain variable region and the light chain variable region. In certain embodiments, the extracellular antigen-binding domain is a scFv. In certain embodiments, the extracellular antigen-binding domain is a Fab, which is optionally crosslinked. In certain embodiments, the extracellular binding domain is a F(ab)$_2$. In certain embodiments, any of the foregoing molecules can be comprised in a fusion protein with a heterologous sequence to form the extracellular antigen-binding domain.

In accordance with the presently disclosed subject matter, the extracellular antigen-binding domain is covalently joined to a transmembrane domain. The extracellular antigen-binding domain can comprise a signal peptide that is covalently joined to the 5' terminus of the extracellular antigen-binding domain. In certain embodiments, the transmembrane domain of a presently disclosed CAR comprises a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide (not based on a protein associated with the immune response), or a combination thereof. In certain embodiments, the transmembrane domain comprises a CD28 polypeptide.

In accordance with the presently disclosed subject matter, the intracellular domain comprises a CD3ζ polypeptide. In certain embodiments, the intracellular domain further comprises at least one signaling region. In certain embodiments, the at least one signaling region comprises a CD28 polypeptide, a 4-1BB polypeptide, an OX40 polypeptide, an ICOS polypeptide, a DAP-10 polypeptide, a PD-1 polypeptide, a CTLA-4 polypeptide, a LAG-3 polypeptide, a 2B4 polypeptide, a BTLA polypeptide, a synthetic peptide (not based on a protein associated with the immune response), or a combination thereof. In certain embodiments, the signaling region is a co-stimulatory signaling region. In certain embodiments, the co-stimulatory signaling region comprises a a CD28 polypeptide, a 4-1BB polypeptide, an OX40 polypeptide, an ICOS polypeptide, a DAP-10 polypeptide, or a combination thereof. In certain embodiments, the at least one co-stimulatory signaling region comprises a CD28 polypeptide. In certain non-limiting embodiments, the transmembrane domain comprises a CD28 polypeptide, the intracellular domain comprises a CD3 polypeptide, and the co-stimulatory signaling domain comprises a CD28 polypeptide.

In certain embodiments, the CAR is recombinantly expressed. The CAR can be expressed from a vector. In certain embodiments, the vector is a γ-retroviral vector.

The presently disclosed subject matter also provides isolated immunoresponsive cells comprising the above-described CARs. In certain embodiments, the isolated immunoresponsive cell is transduced with the CAR, for example, the CAR is constitutively expressed on the surface of the immunoresponsive cell. In certain embodiments, the isolated immunoresponsive cell is selected from the group consisting of a T cell, a Natural Killer (NK) cell, a human embryonic stem cell, a lymphoid progenitor cell, a T cell-precursor cell, and a pluripotent stem cell from which lymphoid cells may be differentiated. In certain embodiments, the immunoresponsive cell is a T cell. The T cell can be selected from the group consisting of a cytotoxic T lymphocyte (CTL), a regulatory T cell, and central memory T cells.

The isolated immunoresponsive cell can further comprise an antigen recognizing receptor that binds to a second antigen that is different than CD56. In certain embodiments, the second antigen is selected from the group consisting of CD138, CS-1, BCMA, CT-7, carbonic anhydrase IX (CAIX), carcinoembryonic antigen (CEA), CD5, CD7, CD10, CD19, CD20, CD22, CD30, CD33, CD34, CD38, CD41, CD44, CD49f, CD74, CD123, CD133, an antigen of a cytomegalovirus (CMV) infected cell (e.g., a cell surface antigen), epithelial glycoprotein2 (EGP 2), epithelial glycoprotein-40 (EGP-40), epithelial cell adhesion molecule (Ep-CAM), receptor tyrosine-protein kinases erb-B2,3,4, folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1CAM), melanoma antigen family A1 (MAGE-A1), MAGE-A3, Mucin 16 (Muc-16), Mucin 1 (Muc-1), methoselin, NKG2D ligands, cancer-testis antigen NY-ESO-1, oncofetal antigen (h5T4), prostate stem cell antigen (PSCA), prostate-specific membrane antigen (PSMA), tumor-associated glycoprotein 72 (TAG-72), vascular endothelial growth factor R2 (VEGF-R2), Wilms tumor protein (WT-1), and a combination thereof. In certain embodiments, the second antigen is CD138. In certain embodiments, the antigen recognizing receptor is a truncated CAR. In certain embodiments, the antigen recognizing receptor is a chimeric co-stimulatory receptor (CCR).

The presently disclosed subject matter further provides nucleic acid molecules encoding the presently disclosed CARs, vectors comprising the nucleic acid molecules, and host cells expressing such nucleic acid molecules. In certain embodiments, the vector is a γ-retroviral vector. In certain embodiments, the host cell is a T cell.

The presently disclosed subject matter further provides antibodies, or antigen-binding fragments thereof, that specifically target CD56. In certain embodiments, an antibody, or antigen-binding portion, thereof comprises: (a) a $V_H$ comprising an amino acid sequence selected from the group consisting of SEQ ID NO: 7, SEQ ID NO: 19, SEQ ID NO: 21, SEQ ID NO: 23, and SEQ ID NO: 25; and/or (b) a $V_L$ comprising an amino acid sequence selected from the group consisting of SEQ ID NO: 8, SEQ ID NO: 20, SEQ ID NO: 22, SEQ ID NO: 24 and SEQ ID NO: 26.

In certain embodiments, a presently disclosed antibody, or antigen-binding portion thereof, comprises:

(a) a heavy chain variable region comprising an amino acid sequence set forth in SEQ ID NO: 7, and a light chain variable region that comprising an amino acid sequence set forth in SEQ ID NO: 8;

(b) a heavy chain variable region comprising an amino acid sequence set forth in SEQ ID NO: 19, and a light chain variable region that comprising an amino acid sequence set forth in SEQ ID NO: 20;

(c) a heavy chain variable region comprising an amino acid sequence set forth in SEQ ID NO: 21, and a light chain variable region that comprising an amino acid sequence set forth in SEQ ID NO: 22;

(d) a heavy chain variable region comprising an amino acid sequence set forth in SEQ ID NO: 23, and a light chain variable region that comprising an amino acid sequence set forth in SEQ ID NO: 24; or (e) a heavy chain variable region comprising an amino acid sequence set forth in SEQ ID NO: 25, and a light chain variable region that comprising an amino acid sequence set forth in SEQ ID NO: 26.

In certain embodiments, a presently disclosed antibody, or antigen-binding portion thereof, comprises:

(a) a heavy chain variable region CDR1 comprising an amino acid sequence selected from the group consisting of SEQ ID NO: 1 and SEQ ID NO: 9;

(b) a heavy chain variable region CDR2 comprising an amino acid sequence selected from the group consisting of SEQ ID NO: 2 and SEQ ID NO: 10;

(c) a heavy chain variable region CDR3 comprising an amino acid sequence selected from the group consisting of SEQ ID NO: 3, SEQ ID NO: 11 and SEQ ID NO: 59;

(d) a light chain variable region CDR1 comprising an amino acid sequence selected from the group consisting of SEQ ID NO: 4, SEQ ID NO: 12 and SEQ ID NO: 13;

(e) a light chain variable region CDR2 comprising an amino acid sequence selected from the group consisting of SEQ ID NO: 5 and SEQ ID NO: 14; and (f) a light chain variable region CDR3 comprising an amino acid sequence selected from the group consisting of SEQ ID NO: 6, SEQ ID NO: 15, SEQ ID NO: 16, SEQ ID NO: 17 and SEQ ID NO: 18.

In certain embodiments, a presently disclosed antibody, or antigen-binding portion thereof, comprises:

(i) a heavy chain variable region CDR3 comprising an amino acid sequence selected from the group consisting of SEQ ID NO: 3, SEQ ID NO: 11 and SEQ ID NO: 59; and/or (ii) a light chain variable region CDR3 comprising an amino acid sequence selected from the group consisting of SEQ ID NO: 6, SEQ ID NO: 15, SEQ ID NO: 16, SEQ ID NO: 17 and SEQ ID NO: 18.

The presently disclosed subject matter further provides nucleic acid molecules encoding the presently disclosed anti-CD56 antibodies, or antigen-binding portions thereof, vectors comprising the nucleic acid molecules, and host cells expressing such nucleic acid molecules.

Furthermore, the presently disclosed subject matter provides methods of using the above-described immunoresponsive cells or anti-CD56 antibodies (or antigen-binding portions thereof) for reducing tumor burden in a subject. For example, and not by way of limitation, the presently disclosed subject matter provides methods of reducing tumor burden in a subject, where the method comprises administering an effective amount of the presently disclosed immunoresponsive cell to the subject, thereby inducing tumor cell death in the subject. In certain embodiments, the method reduces the number of tumor cells. In certain embodiments, the method reduces the tumor size. In certain embodiments, the method eradicates the tumor in the subject. In certain embodiments, the tumor is associated with overexpression of CD56. In certain embodiments, the tumor is selected from the group consisting of multiple myeloma, neuroblastoma, glioma, acute myeloid leukemia, colon cancer, pancreatic cancer, thyroid cancer, small cell lung cancer, and NK cell lymphoma.

Furthermore, the presently disclosed subject matter provides methods of using the above-described immunoresponsive cells or anti-CD56 antibodies (or antigen-binding portions thereof) for increasing or lengthening survival of a subject having neoplasia. For example, and not by way of limitation, the presently disclosed subject matter provides methods of increasing or lengthening survival of a subject having neoplasia, where the method comprises administering an effective amount of the presently disclosed immunoresponsive cell to the subject, thereby increasing or lengthening survival of the subject. In certain embodiments, the neoplasia is associated with overexpression of CD56. In certain embodiments, the neoplasia is selected from the group consisting of multiple myeloma, neuroblastoma, glioma, acute myeloid leukemia, colon cancer, pancreatic cancer, thyroid cancer, small cell lung cancer, and NK cell lymphoma. In certain embodiments, the neoplasia is multiple myeloma. In certain embodiments, the method reduces or eradicates tumor burden in the subject.

In certain embodiments, the tumor is multiple myeloma. In certain embodiments, the subject is a human. In certain embodiments, the immunoresponsive cell is a T cell.

The presently disclosed subject matter also provides methods for producing an immunoresponsive cell that binds to human CD56. In one non-limiting example, the method comprises introducing into the immunoresponsive cell a nucleic acid sequence that encodes the above-described CAR.

The presently disclosed subject matter further provides pharmaceutical compositions comprising an effective amount of the presently disclosed immunoresponsive cells or anti-CD56 antibodies (or antigen-binding portions thereof) and a pharmaceutically acceptable excipient. In certain embodiments, the pharmaceutical compositions are for treating a neoplasia. The presently disclosed subject matter further provides kits for treating a neoplasia, comprising the presently disclosed immunoresponsive cells or anti-CD56 antibodies (or antigen-binding portions thereof). In some embodiments, the kit further includes written instructions for using the immunoresponsive cell for treating a neoplasia. In certain embodiments, the neoplasia is associated with overexpression of CD56. In certain embodiments, the neoplasia is selected from the group consisting of multiple myeloma, neuroblastoma, glioma, acute myeloid leukemia, colon cancer, pancreatic cancer, thyroid cancer, small cell lung cancer, and NK cell lymphoma. In certain embodiments, the neoplasia is multiple myeloma.

The presently disclosed subject matter further provides bispecific molecule comprising a presently disclosed anti-CD56 antibody (or an antigen-binding fragment thereof) linked to a second functional moiety. In certain embodiments, the second functional moiety has a different binding specificity than said antibody or antigen binding fragment thereof. The presently disclosed subjectmatter also provides compositions comprising the bispecific molecules and a pharmaceutically acceptable carrier.

BRIEF DESCRIPTION OF THE FIGURES

The following Detailed Description, given by way of example but not intended to limit the invention to specific embodiments described, may be understood in conjunction with the accompanying drawings.

FIGS. 2A-2D depict the CTL assays showing the relationship between cytotoxicity and affinity of CD56 targeted CARs. Five different CARs corresponding to the Fabs generated by phage display as well as the original 56-28z CAR were compared in a CTL assay for their cytotoxicity against E14 cells expressing high (A) and low levels of CD56 (B). Of all the CARs tested the m900 CAR showed striking activity against $CD56^{high}$ tumor cells (C) but minimal activity when $CD56^{low}$ cells (D) were used as the target.

FIGS. 6A-6D depict expansion and cytokine secretion of 56-28z CAR transduced T cells. 56-28z CAR transduced T cells show antigen dependent expansion and cytokine secretion in vitro. (A) Western blot of T cells showing CAR expression at the expected molecular weight when stained for the cytoplasmic domain of the CD3 zeta chain. Bands shown represent the unphosphorylated and phosphorylated endogenous zeta chain monomers (16 and 21 kD respectively), the zeta chain dimer (32 kD) and 56-28z CAR (56 kD). The left lane shows 56-28z CAR T cells with untransduced T cells in the right lane. (B) Flow cytometry plot demonstrating soluble CD56 binding to 56-28z CAR transduced T cells confirming antigen specificity. (C) In vitro cell growth of 56-28z CAR T cells following weekly stimulation with $CD56^+19^+$ OPM2-19 myeloma cell line in the presence of 20 IU/ml of interleukin-2. The arrows mark stimulation time points. Proliferation of control 19-28z and P28z CARs stimulated under identical conditions is shown for compa-rision. (D) Cytokine concentrations measured in supernatants of 56-28z or P28z CAR and OPM2-19 cocultures at 24 hours post first stimulation. Results shown are the mean of two experiments.

DETAILED DESCRIPTION OF THE INVENTION

Figure 1:
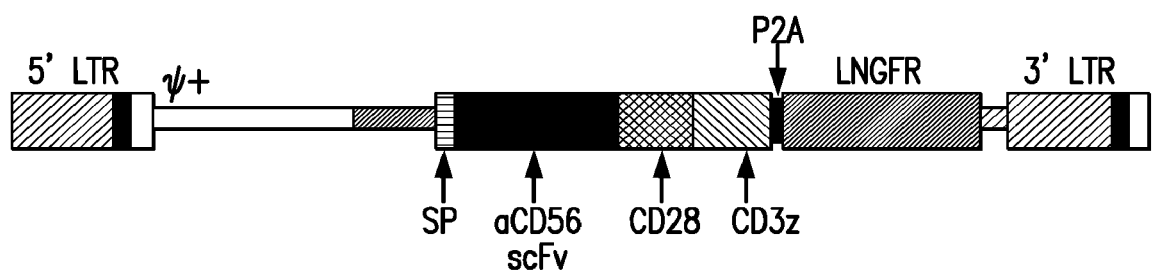
FIG. 1 depicts a chimeric antigen receptor targeting human CD56 in accordance with one non-limiting embodiment of the presently disclosed subject matter.

The presently disclosed subject matter generally provides antigen-binding proteins such as antibodies, or antigen-binding fragments thereof, and chimeric antigen receptors (CARs) targeting human CD56.

In certain embodiments, the CAR comprises an extracellular antigen-binding domain, a transmembrane domain and an intracellular domain, where the extracellular antigen-binding domain cross-competes for binding to human CD56 with a reference antibody or an antigen-binding portion thereof comprising a heavy chain variable region CDR1 comprising amino acids having the sequence set forth in SEQ ID NO: 1; a heavy chain variable region CDR2 comprising amino acids having the sequence set forth in SEQ ID NO: 2; a heavy chain variable region CDR3 comprising amino acids having the sequence set forth in SEQ ID NO: 3 or SEQ ID NO: 59; a light chain variable region CDR1 comprising amino acids having the sequence set forth in SEQ ID NO: 4; a light chain variable region CDR2 comprising amino acids having the sequence set forth in SEQ ID NO: 5; and a light chain variable region CDR3 comprising amino acids having the sequence set forth in SEQ ID NO: 6. In certain embodiments, the CAR comprises an extracellular antigen-binding domain, a transmembrane domain and an intracellular domain, where the extracellular antigen-binding domain binds to the same epitope on human CD56 as a reference antibody or an antigen-binding portion thereof comprising a heavy chain variable region CDR1 comprising amino acids having the sequence set forth in SEQ ID NO: 1; a heavy chain variable region CDR2 comprising amino acids having the sequence set forth in SEQ ID NO: 2; a heavy chain variable region CDR3 comprising amino acids having the sequence set forth in SEQ ID NO: 3 or SEQ ID NO: 59; a light chain variable region CDR1 comprising amino acids having the sequence set forth in SEQ ID NO: 4; a light chain variable region CDR2 comprising amino acids having the sequence set forth in SEQ ID NO: 5; and a light chain variable region CDR3 comprising amino acids having the sequence set forth in SEQ ID NO: 6. In certain embodiments, the CAR comprises an extracellular antigen-binding domain, a transmembrane domain and an intracellular domain, where the extracellular antigen-binding domain specifically binds to human CD56 with a binding affinity ($K_d$) of about $3\times10^{-9}$ or less. In a further non-limiting example, the CAR comprises an extracellular antigen-binding domain, a transmembrane domain and an intracellular domain, where the extracellular antigen-binding domain specifically binds to human CD56 with a binding affinity ($K_d$) of from about $3\times10^{-9}$ to about $2\times10^{-7}$.

In certain non-limiting embodiments of the present disclosure, an anti-CD56 antibody (or antigen-binding portion thereof) comprises: (a) a $V_H$ comprising an amino acid sequence selected from the group consisting of SEQ ID NO: 7, SEQ ID NO: 19, SEQ ID NO: 21, SEQ ID NO: 23, and SEQ ID NO: 25; and/or (b) a $V_L$ comprising an amino acid sequence selected from the group consisting of SEQ ID NO: 8, SEQ ID NO: 20, SEQ ID NO: 22, SEQ ID NO: 24 and SEQ ID NO: 26. The presently disclosed subject matter further provides methods for using such anti-CD56 antibodies (or antigen-binding portions thereof) for treating a tumor.

The presently disclosed subject matter also provides immunoresponsive cells (e.g., a T cell (e.g., a cytotoxic T lymphocyte (CTL), a regulatory T cell, a central memory T cell, etc.), a Natural Killer (NK) cell, a human embryonic stem cell, a lymphoid progenitor cell, a T cell-precursor cell, and a pluripotent stem cell from which lymphoid cells may be differentiated) expressing the CD56-targeted CARs, and methods of using such immunoresponsive cells for treating a tumor, e.g., multiple myeloma.

I. Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "cell population" refers to a group of at least two cells expressing similar or different phenotypes. In non-limiting examples, a cell population can include at least about 10, at least about 100, at least about 200, at least about 300, at least about 400, at least about 500, at least about 600, at least about 700, at least about 800, at least about 900, at least about 1000 cells expressing similar or different phenotypes.

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments that lack the Fc fragment of intact antibody, clear more rapidly from the circulation, and may have less non-specific tissue binding of an intact antibody (Wahl et al., *J. Nucl. Med.* 24:316-325 (1983)). The antibodies of the invention comprise whole native antibodies, bispecific antibodies; chimeric antibodies; Fab, Fab', single chain V region fragments (scFv), fusion polypeptides, and unconventional antibodies. In certain embodiments, an antibody is a glycoprotein comprising at least two heavy (H) chains and two light (L) chains interconnected by disulfide bonds. Each heavy chain is comprised of a heavy chain variable region (abbreviated herein as $V_H$) and a heavy chain constant ($C_H$) region. The heavy chain constant region is comprised of three domains, CH1, CH2 and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further sub-divided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1 q) of the classical complement system.

As used herein interchangeably, the terms "antigen-binding portion", "antigen-binding fragment", or "antigen-binding region" of an antibody, refer to the region or portion of an antibody that binds to the antigen and which confers antigen specificity to the antibody; fragments of antigen-binding proteins, for example, antibodies includes one or more fragments of an antibody that retain the ability to specifically bind to an antigen (e.g., an peptide/HLA complex). It has been shown that the antigen-binding function of an antibody can be performed by fragments of a full-length antibody. Examples of antigen-binding portions encompassed within the term "antibody fragments" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules. These are known as single chain Fv (scFv); see e.g., Bird et al., 1988 Science 242:423-426; and Huston et al., 1988 Proc. Natl. Acad. Sci. 85:5879-5883. These antibody fragments are obtained using conventional techniques known to those of ordinary skill in the art, and the fragments are screened for utility in the same manner as are intact antibodies.

An "isolated antibody" or "isolated antigen-binding protein" is one which has been identified and separated and/or recovered from a component of its natural environment. "Synthetic antibodies" or "recombinant antibodies" are generally generated using recombinant technology or using peptide synthetic techniques known to those of skill in the art.

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H$::$V_L$ heterodimer. The heavy ($V_H$) and light chains ($V_L$) are either joined directly or joined by a peptide-encoding linker (e.g., about 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain. In certain embodiments, the linker comprises amino acids having the sequence set forth in SEQ ID NO:27 as provided below.

GGGGSGGGGSGGGGS [SEQ ID NO:27]

In certain embodiments, the nucleic acid sequence encoding the amino acid sequence of SEQ ID NO:27 is set forth in SEQ ID NO:28, which is provided below:

GGCGGCGGCGGATCTGGAGGTGGTGGCTCAG-GTGGCGGAGGCTCC [SEQ ID NO:28]

Despite removal of the constant regions and the introduction of a linker, scFv proteins retain the specificity of the original immunoglobulin. Single chain Fv polypeptide antibodies can be expressed from a nucleic acid comprising $V_H$- and $V_L$-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chem 2003 25278(38):36740-7; Xie et al., Nat Biotech 1997 15(8):768-71; Ledbetter et al., Crit Rev Immuno 11997 17(5-6):427-55; Ho et al., BioChim Biophys Acta 2003 1638(3):257-66).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "F(ab')$_2$" refers to an antibody fragment generated by pepsin digestion of whole IgG antibodies, wherein this fragment has two antigen binding (zab') (bivalent) regions, wherein each (ab') region comprises two separate amino acid chains, a part of a H chain and a light (L) chain linked by an S—S bond for binding an antigen and where the remaining H chain portions are linked together. A "F(ab')$_2$" fragment can be split into two individual Fab' fragments.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

As used herein, the term "expression vector" refers to a recombinant nucleic acid sequence, e.g., a recombinant DNA molecule, containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat system (Kabat, E. A., et al. (1991) Sequences of Proteins of Immunological Interest, Fifth Edition, U.S. Department of Health and Human Services, NIH Publication No. 91-3242).

As used herein, the term "affinity" is meant a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes. Methods for calculating the affinity of an antibody for an antigen are known in the art, comprising use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay).

Nucleic acid molecules useful in the presently disclosed subject matter include any nucleic acid molecule that encodes a polypeptide or a fragment thereof. In certain embodiments, nucleic acid molecules useful in the presently disclosed subject matter include nucleic acid molecules that encode an antibody or an antigen-binding portion thereof. Such nucleic acid molecules need not be 100% identical with an endogenous nucleic acid sequence, but will typically exhibit substantial identity. Polynucleotides having "substantial homology" or "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In certain embodiments, hybridization will occur at 30° C. in 750 mM NaCl, 75 mM trisodium citrate, and 1% SDS. In certain embodiments, hybridization will occur at 37° C. in 500 mM NaCl, 50 mM trisodium citrate, 1% SDS, 35% formamide, and 100 μg/ml denatured salmon sperm DNA (ssDNA). In certain embodiments, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In certain embodiments, wash steps will occur at 25° C. in 30 mM NaCl, 3 mM trisodium citrate, and 0.1% SDS. In certain embodiments, wash steps will occur at 42° C. in 15 mM NaCl, 1.5 mM trisodium citrate, and 0.1% SDS. In certain embodiments, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Rogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

The terms "substantially homologous" or "substantially identical" mean a polypeptide or nucleic acid molecule that exhibits at least 50% homology or identity to a reference amino acid sequence (for example, any one of the amino acid sequences described herein) or nucleic acid sequence (for example, any one of the nucleic acid sequences described herein). For example, such a sequence is at least about 60%, about 65%, about 70%, about 75%, about 80%, about 85%, about 90%, about 95% or even about 99% homologous or identical at the amino acid level or nucleic acid to the sequence used for comparison.

Sequence homology or sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. In an exemplary approach to determining the degree of identity, a BLAST program may be used, with a probability score between $e^{-3}$ and $e^{-100}$ indicating a closely related sequence.

In certain embodiments, the term "cross-compete" or "compete" refers to the situation where binding of an extracellular antigen-binding domain of a presently disclosed CAR to a given antigen, i.e., CD56 (e.g., human CD56), decreases or reduces binding of a reference antibody or an antigen-binding portion thereof, e.g., that comprises the $V_H$ and $V_L$ CDR1, CDR2, and CDR3 sequences or $V_H$ and $V_L$ sequences of any one of the presently disclosed scFvs (e.g., m903, m904, m905, m906, and m900 (which can also be referred to herein as m907)), to the same antigen, i.e., CD56 (e.g., human CD56). The term "cross-compete" or "compete" also refers to the situation where binding of a reference antibody or an antigen-binding portion thereof to a given antigen, i.e., CD56 (e.g., human CD56), decreases or reduces binding of an extracellular antigen-binding domain of a presently disclosed CAR to the same antigen. In certain embodiments, the "cross-competing" or "competing" extracellular antigen-binding domain binds to the same or substantially the same epitope, an overlapping epitope, or an adjacent epitope on CD56 (e.g., human CD56) as the reference antibody or antigen-binding portion thereof.

As used herein, the term "analog" refers to a structurally related polypeptide or nucleic acid molecule having the function of a reference polypeptide or nucleic acid molecule.

As used herein, the term "ligand" refers to a molecule that binds to a receptor. In particular, the ligand binds a receptor on another cell, allowing for cell-to-cell recognition and/or interaction.

As used herein, the term "disease" refers to any condition or disorder that damages or interferes with the normal function of a cell, tissue, or organ. Examples of diseases include neoplasia or pathogen infection of cell.

An "effective amount" (or "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease (e.g., a neoplasia), or otherwise reduce the pathological consequences of the disease (e.g., a neoplasia). The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

As used herein, the term "neoplasia" refers to a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, colon, bone, brain, breast, cartilage, glia, esophagus, fallopian tube, gallbladder, heart, intestines, kidney, liver, lung, lymph node, nervous tissue, ovaries, pleura, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells).

As used herein, the term "heterologous nucleic acid molecule or polypeptide" refers to a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

As used herein, the term "immunoresponsive cell" refers to a cell that functions in an immune response or a progenitor, or progeny thereof.

As used herein, the term "modulate" refers positively or negatively alter. Exemplary modulations include an about 1%, about 2%, about 5%, about 10%, about 25%, about 50%, about 75%, or about 100% change.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, the term "isolated cell" refers to a cell that is separated from the molecular and/or cellular components that naturally accompany the cell.

As used herein, the term "isolated," "purified," or "biologically pure" refers to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or polypeptide of the presently disclosed subject matter is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

As used herein, the term "secreted" is meant a polypeptide that is released from a cell via the secretory pathway through the endoplasmic reticulum, Golgi apparatus, and as a vesicle that transiently fuses at the cell plasma membrane, releasing the proteins outside of the cell.

As used herein, the term "specifically binds" or "specifically binds to" or "specifically target" is meant a polypeptide or fragment thereof that recognizes and binds a biological molecule of interest (e.g., a polypeptide), but which does not substantially recognize and bind other molecules in a sample, for example, a biological sample, which includes or expresses a human CD56.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject" refers to any animal (e.g., a mammal), including, but not limited to, humans, non-human primates, rodents, and the like (e.g., which is to be the recipient of a particular treatment, or from whom cells are harvested).

II. CD56

The neural cell adhesion molecule CD56 is one of the most frequently expressed antigens in myeloma. CD56 plays an important role in tumorigenesis by mediating cell-cell adhesion, thereby facilitating the interaction of myeloma cells with bone marrow stromal cells, as well as by promoting tumor cell migration, invasion and proliferation and inhibiting apoptosis (Gattenloehner, et al. Novel RUNX1 isoforms determine the fate of acute myeloid leukemia cells by controlling CD56 expression. *Blood.* 2007; 110:2027-2033). It is expressed normally on natural killer cells, a subset of T lymphocytes, neuroendocrine tissue and in the brain where its expression peaks during embryogenesis but remains expressed at low levels even in the adult brain. Importantly, CD56 is uniformly expressed at a significantly higher density in over 70% of patients with myeloma (Tassone, et al. In vitro and in vivo activity of the maytansinoid immunoconjugate huN901-N2'-deacetyl-N2'-(3-mercapto-1-oxopropyl)-maytansine against CD56+ multiple myeloma cells. Cancer Res. 2004; 64:4629-4636). A Phase I trial with the anti-CD56 monoclonal antibody lorvotuzumab in combination with lenalidomide and prednisolone showed encouraging clinical responses and minimal toxicity in relapsed, refractory myeloma patients (Jesus G. Berdej a et al., "Phase I Study of Lorvotuzumab Mertansine (LM, IMGN901) in Combination with Lenalidomide (Len) and Dexamethasone (Dex) in Patients with CD56-Positive Relapsed or Relapsed/Refractory Multiple Myeloma (MM) ", Blood (ASH Annual Meeting Abstracts), November 2012; 120: 728). In certain non-limiting embodiments, CD56 is a human CD56 polypeptide.

III. Chimeric Antigen Receptor (CAR)

Chimeric antigen receptors (CARs) are engineered receptors, which graft or confer a specificity of interest onto an immune effector cell. CARs can be used to graft the specificity of a monoclonal antibody onto a T cell; with transfer of their coding sequence facilitated by retroviral vectors.

There are three generations of CARs. "First generation" CARs are typically composed of an extracellular antigen binding domain (e.g., a single-chain variable fragments (scFv)) fused to a transmembrane domain, fused to cytoplasmic/intracellular domain of the T cell receptor chain. "First generation" CARs typically have the intracellular domain from the CD3ζ-chain, which is the primary transmitter of signals from endogenous TCRs. "First generation" CARs can provide de novo antigen recognition and cause activation of both CD4⁻ and CD8⁻ T cells through their CD3t chain signaling domain in a single fusion molecule, independent of HLA-mediated antigen presentation. "Second generation" CARs add intracellular domains from various co-stimulatory molecules (e.g., CD28, 4-1BB, ICOS, OX40) to the cytoplasmic tail of the CAR to provide additional signals to the T cell. "Second generation" CARs comprise those that provide both co-stimulation (e.g., CD28 or 4-1BB) and activation (CD3ζ). Preclinical studies have indicated that "Second Generation" CARs can improve the anti-tumor activity of T cells. For example, robust efficacy of "Second Generation" CAR modified T cells was demonstrated in clinical trials targeting the CD19 molecule in patients with chronic lymphoblastic leukemia (CLL) and acute lymphoblastic leukemia (ALL). "Third generation" CARs comprise those that provide multiple co-stimulation (e.g., CD28 and 4-1BB) and activation (CD3).

In certain non-limiting embodiments, the extracellular antigen-binding domain of a presently disclosed CAR has a high binding specificity as well as high binding affinity to human CD56. For example, in such embodiments, the extracellular antigen-binding domain of the CAR (embodied, for example, in a human scFv or an analog thereof) binds to human CD56 with a dissociation constant ($K_d$) of about $2 \times 10^{-7}$ M or less. In certain embodiments, the $K_d$ is about $2 \times 10^{-7}$ M or less, about $1 \times 10^{-7}$ M or less, about $9 \times 10^{-8}$ M or less, about $1 \times 10^{-8}$ M or less, about $9 \times 10^{-9}$ or less, about $5 \times 10^{-9}$ or less, about $4 \times 10'$ or less, about $3 \times 10^{-9}$ or less, about $2 \times 10^{-9}$ or less, or about $1 \times 10^{-9}$ M or less. In certain non-limiting embodiments, the $K_d$ is from about $3 \times 10^{-9}$ M or less. In certain non-limiting embodiments, the $K_d$ is from about $3 \times 10^{-9}$ to about $2 \times 10^{-7}$.

Binding of the extracellular antigen-binding domain (embodiment, for example, in a human scFv or an analog thereof) of a presently disclosed CAR56-targeted CAR can be confirmed by, for example, enzyme-linked immunosorbent assay (ELISA), radioimmunoassay (RIA), FACS analysis, bioassay (e.g., growth inhibition), or Western Blot assay.

Each of these assays generally detect the presence of protein-antibody complexes of particular interest by employing a labeled reagent (e.g., an antibody, or a scFv) specific for the complex of interest. For example, the scFv can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography. In certain embodiments, the extracellular antigen-binding domain of the CD56-targeted CAR is labeled with a fluorescent marker. Non-limiting examples of fluorescent markers include green fluorescent protein (GFP), blue fluorescent protein (e.g., EBFP, EBFP2, Azurite, and mKalama1), cyan fluorescent protein (e.g., ECFP, Cerulean, and CyPet), and yellow fluorescent protein (e.g., YFP, Citrine, Venus, and YPet). In certain embodiments, the human scFv of a presently disclosed CD56-targeted CAR is labeled with GFP.

In accordance with the presently disclosed subject matter, the CARs comprise an extracellular antigen-binding domain, a transmembrane domain and an intracellular domain, where the extracellular antigen-binding domain specifically binds to CD56 (e.g., human CD56). In certain embodiments, the extracellular antigen-binding domain is an scFv. In certain embodiments, the extracellular antigen-binding domain is a Fab, which is optionally crosslinked. In a certain embodiments, the extracellular binding domain is a F(ab)$_2$. In certain embodiments, any of the foregoing molecules may be comprised in a fusion protein with a heterologous sequence to form the extracellular antigen-binding domain. In certain embodiments, the extracellular antigen-binding domain comprises a human scFv that binds specifically to human CD56. In certain embodiments, the scFv is identified by screening scFv phage library with CD56-Fc fusion protein.

Extracellular Antigen Binding Domain of A CAR

In certain embodiments, the extracellular antigen-binding domain (e.g., human scFv) comprises a heavy chain variable region comprising amino acids having a sequence selected from the group consisting of: SEQ ID NOS: 7, 19, 21, 23 and 25. The nucleic acid sequences encoding the amino acid sequence of SEQ ID NOS: 7, 19, 21, 23 and 25 are 35, 37, 39, 41, and 43, respectively. In some embodiments, the extracellular antigen-binding domain (e.g., human scFv) comprises a light chain variable region comprising amino acids having a sequence selected from the group consisting of SEQ ID NOS: 8, 20, 22, 24, and 26. The nucleic acid sequences encoding the amino acid sequence of SEQ ID NOS: 8, 20, 22, 24, and 26 are 36, 38, 40, 42, and 44, respectively. The sequences of SEQ ID NOS:1-26, 35-49 and 59 are described in the following Tables 1-5.

In certain embodiments, the extracellular antigen-binding domain is a human scFv, which comprises the amino acid sequence of SEQ ID NO: 39 and specifically binds to a CD56 polypeptide (e.g., a human CD56 polypeptide), which is designated as scFv m900 (also referred to herein as scFv m907).

In certain embodiments, the extracellular antigen-binding domain is a human scFv, which comprises a heavy chain variable region comprising amino acids having the sequence set forth in SEQ ID NO:7 and a light chain variable region comprising amino acids having the sequence set forth in SEQ ID NO:8, optionally with (iii) a linker sequence, for example a linker peptide, between the heavy chain variable region and the light chain variable region. In certain embodiments, the linker comprises amino acids having the sequence set forth in SEQ ID NO:27. In certain embodiments, the extracellular antigen-binding domain is a human scFv-Fc fusion protein or full length human IgG with $V_H$ and $V_L$ regions or CDRs selected from Table 1. In certain embodiments, the extracellular antigen-binding domain comprises a $V_H$ comprising an amino acid sequence that is at least about 80% (e.g., at least about 85%, at least about 90%, or at least about 95%) homologous to SEQ ID NO: 7, as shown in Table 1. For example, the extracellular antigen-binding domain comprises a $V_H$ comprising an amino acid sequence that is about 80%, 81%, 82%, 83%, 84%, 85%, 86%, 87%, 88%, 89%, 90%, 91%, 92%, 93%, 94%, 95%, 96%, 97%, 98%, or 99% homologous to SEQ ID NO: 7. In certain embodiments, the extracellular antigen-binding domain comprises a $V_H$ comprising amino acids having the sequence set forth in SEQ ID NO:7. In certain embodiments, the extracellular antigen-binding domain comprises a $V_L$ comprising an amino acid sequence that is at least about 80% (e.g., at least about 85%, at least about 90%, or at least about 95%) homologous to SEQ ID NO: 8, as shown in Table 1. For example, the extracellular antigen-binding domain comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous to SEQ ID NO: 8. In certain embodiments, the extracellular antigen-binding domain comprises a $V_L$ comprising amino acids having the sequence set forth in SEQ ID NO:8. In certain embodiments, the extracellular antigen-binding domain comprises a $V_H$ comprising an amino acid sequence that is at least about 80% (e.g., at least about 85%, at least about 90%, or at least about 95%) homologous to SEQ ID NO: 7, and a $V_L$ comprising an amino acid sequence that is at least about 80% (e.g., at least about 85%, at least about 90%, or at least about 95%) homologous to SEQ ID NO: 8. In certain embodiments, the extracellular antigen-binding domain comprises a VH comprising amino acids having the sequence set forth in SEQ ID NO:7 and a $V_L$ comprising amino acids having the sequence set forth in SEQ ID NO:8. In certain embodiments, the extracellular antigen-binding domain comprises a $V_H$ CDR1 comprising amino acids having the sequence set forth in SEQ ID NO:1 or a conservative modification thereof, a $V_H$ CDR2 comprising amino acids having the sequence set forth in SEQ ID NO:2 or a conservative modification thereof, and a $V_H$ CDR3 comprising amino acids having the sequence set forth in SEQ ID NO:3, a conservative modification of SEQ ID NO: 3, SEQ ID NO: 59, or a conservative modification of of SEQ ID NO: 59, as shown in Table 1. In certain embodiments, the extracellular antigen-binding domain comprises a $V_H$ CDR1 comprising amino acids having the sequence set forth in SEQ ID NO:1, a $V_H$ CDR2 comprising amino acids having the sequence set forth in SEQ ID NO:2, and a $V_H$ CDR3 comprising amino acids having the sequence set forth in SEQ ID NO:3 or SEQ ID NO: 59. In certain embodiments, the extracellular antigen-binding domain comprises a $V_L$ CDR1 comprising amino acids having the sequence set forth in SEQ ID NO:4 or a conservative modification thereof, a $V_L$ CDR2 comprising amino acids having the sequence set forth in SEQ ID NO: 5 or a conservative modification thereof, and a $V_L$ CDR3 comprising amino acids having the sequence set forth in SEQ ID NO: 6 or a conservative modification thereof, as shown in Table 1. In certain embodiments, the extracellular antigen-binding domain comprises a $V_L$ CDR1 comprising amino acids having the sequence set forth in SEQ ID NO:4, a $V_L$ CDR2 comprising amino acids having the sequence set forth in SEQ ID NO: 5, and a $V_L$ CDR3 comprising amino acids having the sequence set forth in SEQ ID NO: 6. In certain embodiments, the extracellular antigen-binding domain comprises a $V_H$ CDR1 comprising amino acids having the sequence set forth in SEQ ID NO: 1 or a conservative modification thereof, a $V_H$ CDR2 comprising amino acids having the sequence set forth in SEQ ID NO: 2 or a conservative modification thereof, a $V_H$ CDR3 comprising amino acids having the sequence set forth in SEQ ID NO: 3, a conservative modification of SEQ ID NO: 3, SEQ ID NO: 59, or a conservative modification of of SEQ ID NO: 59, a $V_L$ CDR1 comprising amino acids having the sequence set forth in SEQ ID NO: 4 or a conservative modification thereof, a $V_L$ CDR2 comprising amino acids having the sequence set forth in SEQ ID NO: 5 or a conservative modification thereof, and a $V_L$ CDR3 comprising amino acids having the sequence set forth in SEQ ID NO: 6 or a conservative modification thereof. In certain embodiments, the extracellular antigen-binding domain comprises a $V_H$ CDR1 comprising amino acids having the sequence set forth in SEQ ID NO: 1, a $V_H$ CDR2 comprising amino acids having the sequence set forth in SEQ ID NO: 2, a $V_H$ CDR3 comprising amino acids having the sequence set forth in SEQ ID NO: 3 (or SEQ ID NO: 59), a $V_L$ CDR1 comprising amino acids having the sequence set forth in SEQ ID NO: 4, a $V_L$ CDR2 comprising amino acids having the sequence set forth in SEQ ID NO: 5, and a $V_L$ CDR3 comprising amino acids having the sequence set forth in SEQ ID NO: 6.

TABLE 1

| Antigen | A CD56 polypeptide | | |
|---|---|---|---|
| CDRs | 1 | 2 | 3 |
| $V_H$ | GDSVSSNSAA [SEQ ID NO: 1] | TYYRSKWYN [SEQ ID NO: 2] | ARENIAAWTWAFDIW [SEQ ID NO: 3] or CARENIAAWTWAFDIW [SEQ ID NO: 59] |
| $V_L$ | QSVSSSY [SEQ ID NO: 4] | DTS [SEQ ID NO: 5] | QQYGSSPTF [SEQ ID NO: 6] |
| Full $V_H$ | QVQLQQSGPGLVKPSQTLSLTCAISGDSVSSNSAAWNWIRQSPS RGLEWLGRTYYRSKWYNDYAVSVKSRITINPDTSKNQFSLQLNS VTPEDTAVYYCARENIAAWTWAFDIWGQGTMVTVSS [SEQ ID NO: 7] | | |
| DNA | CAAGTACAGCTCCAACAGTCAGGACCCGGTCTCGTTAAACCTTC CCAAACGCTGTCCCTCACTTGCGCCATCAGCGGAGATTCCGTGA GCTCTAACTCTGCCGCTTGGAACTGGATTAGGCAATCCCCCTCC CGAGGACTGGAATGGCTGGGAAGAACTTACTACCGCTCCAAATG GTACAACGACTACGCAGTGTCCGTCAAGTCTCGAATCACTATCA ACCCTGACACAAGCAAAAATCAGTTTTCCCTGCAACTCAACTCA GTCACCCCTGAGGACACGGCGGTTTACTATTGCGCTAGAGAGAA TATTGCCGCATGGACCTGGGCGTTCGATATATGGGGTCAGGGAA CAATGGTAACCGTCAGCTCC [SEQ ID NO: 29] | | |
| Full $V_L$ | EIVMTQSPGTLSLSPGERATLSCRASQSVSSSYLAWYQQKPGLA PRLLIYDTSLRATDIPDRFSGSGSGTAFTLTISRLEPEDFAVYY CQQYGSSPTFGQGTKVEIKRTVA [SEQ ID NO: 8] | | |
| DNA | GAAATCGTTATGACACAGTCCCCTGGAACACTCTCCCTGTCTCC TGGTGAAAGAGCTACTCTGTCCTGCCGCGCTAGTCAATCCGTAT CCTCCTCCTACCTTGCTTGGTACCAACAAAAGCCCGGACTTGCC CCACGCCTCCTTATTTACGACACCTCACTCCGCGCAACAGATAT CCCAGATAGATTCTCCGGATCAGGCTCCGGGACCGCTTTTACAC ATGACATTTCTAGGCTCGAACCAGAGGACTTCGCTGTATATTAC | | |

TABLE 1-continued

| | |
|---|---|
| | TGCCAACAGTATGGCTCTTCACCAACATTCGGACAAGGCACCAA AGTCGAAATCAAACGCACCGTAGCC [SEQ ID NO: 30] |
| scFv | QVQLQQSGPGLVKPSQTLSLTCAISGDSVSSNSAAWNWIRQSPS RGLEWLGRTYYRSKWYNDYAVSVKSRITINPDTSKNQFSLQLNS VTPEDTAVYYCARENIAAWTWAFDIWGQGTMVTVSSGGGGSGGG GSGGGGSEIVMTQSPGTLSLSPGERATLSCRASQSVSSSYLAWY QQKPGLAPRLLIYDTSLRATDIPDRFSGSGSGTAFTLTISRLEP EDFAVYYCQQYGSSPTFGQGTKVEIKRTVA [SEQ ID NO: 39] |

In certain embodiments, the extracellular antigen-binding domain is a human scFv, which comprises the amino acid sequence of SEQ ID NO: 40 and specifically binds to a CD56 polypeptide (e.g., a human CD56 polypeptide), which is designated as scFv m903.

In certain embodiments, the extracellular antigen-binding domain is a human scFv, which comprises a heavy chain variable region comprising amino acids having the sequence set forth in SEQ ID NO: 19 and a light chain variable region comprising amino acids having the sequence set forth in SEQ ID NO: 20, optionally with (iii) a linker sequence, for example a linker peptide, between the heavy chain variable region and the light chain variable region. In certain embodiments, the linker comprises amino acids having the sequence set forth in SEQ ID NO: 27. In certain embodiments, the extracellular antigen-binding domain is a human scFv-Fc fusion protein or full length human IgG with $V_H$ and $V_L$ regions or CDRs selected from Table 2. In certain embodiments, the extracellular antigen-binding domain comprises a $V_H$ comprising an amino acid sequence that is at least about 80% (e.g., at least about 85%, at least about 90%, or at least about 95%) homologous to SEQ ID NO: 19, as shown in Table 2. For example, the extracellular antigen-binding domain comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous to SEQ ID NO: 19. In certain embodiments, the extracellular antigen-binding domain comprises a $V_H$ comprising amino acids having the sequence set forth in SEQ ID NO: 19. In certain embodiments, the extracellular antigen-binding domain comprises a $V_L$ comprising an amino acid sequence that is at least about 80% (e.g., at least about 85%, at least about 90%, or at least about 95%) homologous to SEQ ID NO: 20, as shown in Table 2. For example, the extracellular antigen-binding domain comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous to SEQ ID NO: 20. In certain embodiments, the extracellular antigen-binding domain comprises a $V_L$ comprising amino acids having the sequence set forth in SEQ ID NO: 20. In certain embodiments, the extracellular antigen-binding domain comprises a $V_H$ comprising an amino acid sequence that is at least about 80% (e.g., at least about 85%, at least about 90%, or at least about 95%) homologous to SEQ ID NO: 19, and a $V_L$ comprising an amino acid sequence that is at least about 80% (e.g., at least about 85%, at least about 90%, or at least about 95%) homologous to SEQ ID NO: 20. In certain embodiments, the extracellular antigen-binding domain comprises a $V_H$ comprising amino acids having the sequence set forth in SEQ ID NO: 19 and a $V_L$ comprising amino acids having the sequence set forth in SEQ ID NO: 20. In certain embodiments, the extracellular antigen-binding domain comprises a $V_H$ CDR1 comprising amino acids having the sequence set forth in SEQ ID NO: 9 or a conservative modification thereof, a $V_H$ CDR2 comprising amino acids having the sequence set forth in SEQ ID NO: 10 or a conservative modification thereof, and a $V_H$ CDR3 comprising amino acids having the sequence set forth in SEQ ID NO: 11 or a conservative modification thereof, as shown in Table 2. In certain embodiments, the extracellular antigen-binding domain comprises a $V_H$ CDR1 comprising amino acids having the sequence set forth in SEQ ID NO: 9, a $V_H$ CDR2 comprising amino acids having the sequence set forth in SEQ ID NO: 10, and a $V_H$ CDR3 comprising amino acids having the sequence set forth in SEQ ID NO: 11. In certain embodiments, the extracellular antigen-binding domain comprises a $V_L$ CDR1 comprising amino acids having the sequence set forth in SEQ ID NO: 12 or a conservative modification thereof, a $V_L$ CDR2 comprising amino acids having the sequence set forth in SEQ ID NO: 14 or a conservative modification thereof, and a $V_L$ CDR3 comprising amino acids having the sequence set forth in SEQ ID NO: 15 or a conservative modification thereof, as shown in Table 2. In certain embodiments, the extracellular antigen-binding domain comprises a $V_L$ CDR1 comprising amino acids having the sequence set forth in SEQ ID NO: 12, a $V_L$ CDR2 comprising amino acids having the sequence set forth in SEQ ID NO: 14, and a $V_L$ CDR3 comprising amino acids having the sequence set forth in SEQ ID NO: 15. In certain embodiments, the extracellular antigen-binding domain comprises a $V_H$ CDR1 comprising amino acids having the sequence set forth in SEQ ID NO: 9 or a conservative modification thereof, a $V_H$ CDR2 comprising amino acids having the sequence set forth in SEQ ID NO: 10 or a conservative modification thereof, a $V_H$ CDR3 comprising amino acids having the sequence set forth in SEQ ID NO: 11 or a conservative modification thereof, a $V_L$ CDR1 comprising amino acids having the sequence set forth in SEQ ID NO: 12 or a conservative modification thereof, a $V_L$ CDR2 comprising amino acids having the sequence set forth in SEQ ID NO: 14 or a conservative modification thereof, and a $V_L$ CDR3 comprising amino acids having the sequence set forth in SEQ ID NO: 15 or a conservative modification thereof.

TABLE 2

| Antigen | A CD56 polypeptide | | |
|---|---|---|---|
| CDRs | 1 | 2 | 3 |
| $V_H$ | GGTFTGYY [SEQ ID NO: 9] | INPNSGGT [SEQ ID NO: 10] | ARDLSSGYSGYFDYW [SEQ ID NO: 11] |
| $V_L$ | QSLLHSNGYNY [SEQ ID NO: 12] | LGS [SEQ ID NO: 14] | MQALQTLTF [SEQ ID NO: 15] |
| Full $V_H$ | EVQLVQSGAEVKKPGSSVKVSCKASGGTFTGYYMHWVRQAPGQ GLEWMGWINPNSGGTNYAQKFQGRVTMTRDTSISTAYMELSRL RSDDTAVYYCARDLSSGYSGYFDYWGQGTLVTVSS [SEQ ID NO: 19] | | |
| DNA | GAAGTTCAGCTCGTCCAGTCCGGCGCTGAGGTCAAGAAGCCCG GGTCATCCGTGAAAGTCAGTTGTAAAGCTAGCGGAGGTACATT TACGGGATATTACATGCATTGGGTGCGGCAGGCGCCAGGCCAA GGACTCGAATGGATGGGATGGATCAATCCCAACTCAGGCGGAA CAAATTATGCTCAGAAATTCCAGGGTAGAGTGACTATGACTCG GGATACTAGCATCAGCACAGCATACATGGAACTGTCACGGCTG CGATCCGACGACACTGCAGTGTACTATTGCGCCAGGGACCTCT CTTCAGGATACTCAGGTTACTTCGACTACTGGGGACAAGGCAC ACTCGTGACTGTATCTAGC [SEQ ID NO: 31] | | |
| Full $V_L$ | DVVMTQSPLSLPVTPGEPASISCRSSQSLLHSNGYNYLDWYLQ KPGQSPQLLIYLGSNRASGVPDRFSGSGSGTDFTLKISRVEAE DVGVYYCMQALQTLTFGQGTRLEIKRTVA [SEQ ID NO: 20] | | |
| DNA | GACGTGGTTATGACCCAATCCCCTCTCTCTCCCTGTGACCC CTGGAGAACCCGCTTCAATCTCATGTCGCTCATCTCAATCACT GCTTCATTCCAATGGATACAATTACCTCGATTGGTATCTTCAA AAGCCCGGCCAGTCCCCTCAACTGCTTATCTATCTCGGCTCCA ATAGAGCATCAGGCGTGCCCGATCGATTTTCCGGCTCAGGCTC CGGCACAGATTTTACTCTGAAAATTAGTAGAGTTGAGGCAGAA GATGTGGGTGTCTATTATTGCATGCAAGCTCTGCAGACCCTCA CATTTGGACAGGGAACACGCCTGGAAATTAAACGCACAGTCGC C [SEQ ID NO: 32] | | |
| scFv | EVQLVQSGAEVKKPGSSVKVSCKASGGTFTGYYMHWVRQAPGQ GLEWMGWINPNSGGTNYAQKFQGRVTMTRDTSISTAYMELSRL RSDDTAVYYCARDLSSGYSGYFDYWGQGTLVTVSSGGGGSGGG GSGGGGSDVVMTQSPLSLPVTPGEPASISCRSSQSLLHSNGYN YLDWYLQKPGQSPQLLIYLGSNRASGVPDRFSGSGSGTDFTLK ISRVEAEDVGVYYCMQALQTLTFGQGTRLEIKRTVA [SEQ ID NO: 40] | | |

In certain embodiments, the extracellular antigen-binding domain is a human scFv, which comprises the amino acid sequence of SEQ ID NO: 41 and specifically binds to a CD56 polypeptide (e.g., a human CD56 polypeptide), which is designated as scFv m904.

In certain embodiments, the extracellular antigen-binding domain is a human scFv, which comprises a heavy chain variable region comprising amino acids having the sequence set forth in SEQ ID NO: 21 and a light chain variable region comprising amino acids having the sequence set forth in SEQ ID NO: 22, optionally with (iii) a linker sequence, for example a linker peptide, between the heavy chain variable region and the light chain variable region. In certain embodiments, the linker comprises amino acids having the sequence set forth in SEQ ID NO: 27. In certain embodiments, the extracellular antigen-binding domain is a human scFv-Fc fusion protein or full length human IgG with $V_H$ and $V_L$ regions or CDRs selected from Table 3. In certain embodiments, the extracellular antigen-binding domain comprises a $V_H$ comprising an amino acid sequence that is at least about 80% (e.g., at least about 85%, at least about 90%, or at least about 95%) homologous to SEQ ID NO: 21, as shown in Table 3. For example, the extracellular antigen-binding domain comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous to SEQ ID NO: 21. In certain embodiments, the extracellular antigen-binding domain comprises a $V_H$ comprising amino acids having the sequence set forth in SEQ ID NO: 21. In certain embodiments, the extracellular antigen-binding domain comprises a $V_L$ comprising an amino acid sequence that is at least about 80% (e.g., at least about 85%, at least about 90%, or at least about 95%) homologous to SEQ ID NO: 22, as shown in Table 2. For example, the extracellular antigen-binding domain comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous to SEQ ID NO: 22. In certain embodiments, the extracellular antigen-binding domain comprises a $V_L$ comprising amino acids having the sequence set forth in SEQ ID NO: 22. In certain embodiments, the extracellular antigen-binding domain comprises a $V_H$ comprising an amino acid sequence that is at least about 80% (e.g., at least about 85%, at least about 90%, or at least about 95%) homologous to SEQ ID NO: 21, and a $V_L$ comprising an amino acid sequence that is at least about 80% (e.g., at least about 85%, at least about 90%, or at least about 95%) homologous to SEQ ID NO: 22. In certain embodiments, the extracellular antigen-binding domain comprises a $V_H$ comprising amino acids having the sequence set forth in SEQ ID NO: 21 and a $V_L$ comprising amino acids having the sequence set forth in SEQ ID NO: 22. In certain embodiments, the extracellular antigen-binding domain comprises a VH CDR1 comprising amino acids having the sequence set forth in SEQ ID NO: 9 or a conservative modification thereof, a $V_H$ CDR2 comprising amino acids having the sequence set forth in SEQ ID NO: 10 or a conservative modification thereof, and a $V_H$ CDR3 comprising amino acids having the sequence set forth in SEQ ID NO: 11 or a conservative modification thereof, as shown in Table 3. In certain embodiments, the extracellular antigen-binding domain comprises a $V_H$ CDR1 comprising amino acids having the sequence set forth in SEQ ID NO: 9, a $V_H$ CDR2 comprising amino acids having the sequence set forth in SEQ ID NO: 10, and a $V_H$ CDR3 comprising amino acids having the sequence set forth in SEQ ID NO: 11. In certain embodiments, the extracellular antigen-binding domain comprises a $V_L$ CDR1 comprising amino acids having the sequence set forth in SEQ ID NO: 12 or a conservative modification thereof, a $V_L$ CDR2 comprising amino acids having the sequence set forth in SEQ ID NO: 14 or a conservative modification thereof, and a $V_L$ CDR3 comprising amino acids having the sequence set forth in SEQ ID NO: 16 or a conservative modification thereof, as shown in Table 3. In certain embodiments, the extracellular antigen-binding domain comprises a $V_L$ CDR1 comprising amino acids having the sequence set forth in SEQ ID NO: 12, a $V_L$ CDR2 comprising amino acids having the sequence set forth in SEQ ID NO: 14, and a $V_L$ CDR3 comprising amino acids having the sequence set forth in SEQ ID NO: 16. In certain embodiments, the extracellular antigen-binding domain comprises a $V_H$ CDR1 comprising amino acids having the sequence set forth in SEQ ID NO: 9 or a conservative modification thereof, a $V_H$ CDR2 comprising amino acids having the sequence set forth in SEQ ID NO: 10 or a conservative modification thereof, a $V_H$ CDR3 comprising amino acids having the sequence set forth in SEQ ID NO: 11 or a conservative modification thereof, a $V_L$ CDR1 comprising amino acids having the sequence set forth in SEQ ID NO: 12 or a conservative modification thereof, a $V_L$ CDR2 comprising amino acids having the sequence set forth in SEQ ID NO: 14 or a conservative modification thereof, and a $V_L$ CDR3 comprising amino acids having the sequence set forth in SEQ ID NO: 16 or a conservative modification thereof. In certain embodiments, the extracellular antigen-binding domain comprises a $V_H$ CDR1 comprising amino acids having the sequence set forth in SEQ ID NO: 9, a $V_H$ CDR2 comprising amino acids having the sequence set forth in SEQ ID NO: 10, a $V_H$ CDR3 comprising amino acids having the sequence set forth in SEQ ID NO: 11, a $V_L$ CDR1 comprising amino acids having the sequence set forth in SEQ ID NO: 12, a $V_L$ CDR2 comprising amino acids having the sequence set forth in SEQ ID NO: 14, and a $V_L$ CDR3 comprising amino acids having the sequence set forth in SEQ ID NO: 16.

TABLE 3

| Antigen | A CD56 polypeptide | | |
|---|---|---|---|
| CDRs | 1 | 2 | 3 |
| $V_H$ | GGTFTGYY [SEQ ID NO: 9] | INPNSGGT [SEQ ID NO: 10] | ARDLSSGYSGYFDY W [SEQ ID NO: 11] |
| $V_L$ | QSLLHSNGYNY [SEQ ID NO: 12] | LGS [SEQ ID NO: 14] | MQALQTPPYT [SEQ ID NO: 16] |
| Full $V_H$ | EVQLVQSGAEVKKPGSSVKVSCKASGGTFTGYYMHWVRQAPGQ GLEWMGWINPNSGGTNYAQKFQGRVTMTRDTSISTAYMELSRL RSDDTAVYYCARDLSSGYSGYFDYWGQGTLVTVSS [SEQ ID NO: 21] | | |
| DNA | GAAGTACAATTGGTTCAATCCGGGGCGGAAGTCAAGAAACCAG GATCTAGTGTGAAAGTCAGTTGCAAAGCATCTGGAGGGACATT CACAGGTTATTACATGCACTGGGTTAGACAGGCCCCTGGGCAA GGACTTGAATGGATGGGCTGGATAAACCCTAATAGCGGAGGAA CAAATTATGCTCAAAAATTCCAAGGGAGAGTTACAATGACTCG AGACACTTCTATCAGCACTGCCTATATGGAACTCAGCAGGCTC CGCTCCGACGACACTGCGGTATATTATTGTGCTAGAGATCTCA GCTCCGGGTATAGTGGTTATTTTGATTACTGGGGACAGGGCAC TCTCGTTACTGTGTCATCA [SEQ ID NO: 33] | | |
| Full $V_L$ | DVVMTQSPLSLPVTPGEPASISCRSSQSLLHSNGYNYLDWYLQ KPGQSPQLLIYLGSNRASGVPDRFSGSGSGTDFTLKISRVEAE DVGVYYCMQALQTPPYTFGQGTKLEIKRTVA [SEQ ID NO: 22] | | |
| DNA | GATGTCGTGATGACCCAATCCCCACTGTCCCTCCCTGTAACCC CAGGAGAACCTGCATCAATATCTTGTCGATCCTCACAATCTCT TCTGCACTCAAACGGTTATAATTATCTTGATTGGTATCTCCAA AAGCCAGGGCAAAGTCCACAGCTTCTTATTTACCTCGGCAGTA ATAGAGCTTCAGGTGTTCCCGATAGATTTAGTGGCAGCGGATC TGGTACTGACTTTACCCTTAAAATTTCCCGAGTGGAGGCCGAA AGATGTTGGAGTCTCTACTGCATGCAGGCACTGCAAACCCCAC CATACACTTTCGGTCAAGGTACGAAGCTTGAAATTAAACGAAC CGTAGCA [SEQ ID NO: 34] | | |
| scFv | EVQLVQSGAEVKKPGSSVKVSCKASGGTFTGYYMHWVRQAPGQ GLEWMGWINPNSGGTNYAQKFQGRVTMTRDTSISTAYMELSRL RSDDTAVYYCARDLSSGYSGYFDYWGQGTLVTVSSGGGGSGGG GSGGGGSDVVMTQSPLSLPVTPGEPASISCRSSQSLLHSNGYN YLDWYLQKPGQSPQLLIYLGSNRASGVPDRFSGSGSGTDFTLK ISRVEAEDVGVYYCMQALQTPPYTFGQGTKLEIKRTVA [SEQ ID NO: 41] | | |

In certain embodiments, the extracellular antigen-binding domain is a human scFv, which comprises the amino acid sequence of SEQ ID NO: 42 and specifically binds to a CD56 polypeptide (e.g., a huamn CD56 polypeptide), which is designated as scFv m905.

In certain embodiments, the extracellular antigen-binding domain is a human scFv, which comprises a heavy chain variable region comprising amino acids having the sequence set forth in SEQ ID NO: 23 and a light chain variable region comprising amino acids having the sequence set forth in SEQ ID NO: 24, optionally with (iii) a linker sequence, for example a linker peptide, between the heavy chain variable region and the light chain variable region. In certain embodiments, the linker comprises amino acids having the sequence set forth in SEQ ID NO: 27. In certain embodiments, the extracellular antigen-binding domain is a scFv-Fc fusion protein or full length human IgG with $V_H$ and $V_L$ regions or CDRs selected from Table 4. In certain embodiments, the extracellular antigen-binding domain comprises a V$_H$ comprising an amino acid sequence that is at least about 80% (e.g., at least about 85%, at least about 90%, or at least about 95%) homologous to SEQ ID NO: 23, as shown in Table 2. For example, the extracellular antigen-binding domain comprises a V$_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous to SEQ ID NO: 23. In certain embodiments, the extracellular antigen-binding domain comprises a V$_H$ comprising amino acids having the sequence set forth in SEQ ID NO: 23. In certain embodiments, the extracellular antigen-binding domain comprises a V$_L$ comprising an amino acid sequence that is at least about 80% (e.g., at least about 85%, at least about 90%, or at least about 95%) homologous to SEQ ID NO: 24, as shown in Table 4. For example, the extracellular antigen-binding domain comprises a V$_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous to SEQ ID NO: 24. In certain embodiments, the extracellular antigen-binding domain comprises a V$_L$ comprising amino acids having the sequence set forth in SEQ ID NO: 24. In certain embodiments, the extracellular antigen-binding domain comprises a V$_H$ comprising an amino acid sequence that is at least about 80% (e.g., at least about 85%, at least about 90%, or at least about 95%) homologous to SEQ ID NO: 23, and a V$_L$ comprising an amino acid sequence that is at least about 80% (e.g., at least about 85%, at least about 90%, or at least about 95%) homologous to SEQ ID NO: 24. In certain embodiments, the extracellular antigen-binding domain comprises a V$_H$ comprising amino acids having the sequence set forth in SEQ ID NO: 23 and a V$_L$ comprising amino acids having the sequence set forth in SEQ ID NO: 24. In certain embodiments, the extracellular antigen-binding domain comprises a V$_H$ CDR1 comprising amino acids having the sequence set forth in SEQ ID NO: 9 or a conservative modification thereof, a V$_H$ CDR2 comprising amino acids having the sequence set forth in SEQ ID NO: 10 or a conservative modification thereof, and a V$_H$ CDR3 comprising amino acids having the sequence set forth in SEQ ID NO: 11 or a conservative modification thereof, as shown in Table 4. In certain embodiments, the extracellular antigen-binding domain comprises a V$_H$ CDR1 comprising amino acids having the sequence set forth in SEQ ID NO: 9, a V$_H$ CDR2 comprising amino acids having the sequence set forth in SEQ ID NO: 10, and a V$_H$ CDR3 comprising amino acids having the sequence set forth in SEQ ID NO: 11. In certain embodiments, the extracellular antigen-binding domain comprises a V$_L$ CDR1 comprising amino acids having the sequence set forth in SEQ ID NO: 12 or a conservative modification thereof, a V$_L$ CDR2 comprising amino acids having the sequence set forth in SEQ ID NO: 14 or a conservative modification thereof, and a V$_L$ CDR3 comprising amino acids having the sequence set forth in SEQ ID NO: 17 or a conservative modification thereof, as shown in Table 4. In certain embodiments, the extracellular antigen-binding domain comprises a V$_L$ CDR1 comprising amino acids having the sequence set forth in SEQ ID NO: 12, a V$_L$ CDR2 comprising amino acids having the sequence set forth in SEQ ID NO: 14, and a V$_L$ CDR3 comprising amino acids having the sequence set forth in SEQ ID NO: 17. In certain embodiments, the extracellular antigen-binding domain comprises a V$_H$ CDR1 comprising amino acids having the sequence set forth in SEQ ID NO: 9 or a conservative modification thereof, a V$_H$ CDR2 comprising amino acids having the sequence set forth in SEQ ID NO: 10 or a conservative modification thereof, a V$_H$ CDR3 comprising amino acids having the sequence set forth in SEQ ID NO: 11 or a conservative modification thereof, a V$_L$ CDR1 comprising amino acids having the sequence set forth in SEQ ID NO: 12 or a conservative modification thereof, a V$_L$ CDR2 comprising amino acids having the sequence set forth in SEQ ID NO: 14 or a conservative modification thereof, and a V$_L$ CDR3 comprising amino acids having the sequence set forth in SEQ ID NO: 17 or a conservative modification thereof. In certain embodiments, the extracellular antigen-binding domain comprises a V$_H$ CDR1 comprising amino acids having the sequence set forth in SEQ ID NO: 9, a V$_H$ CDR2 comprising amino acids having the sequence set forth in SEQ ID NO: 10, a V$_H$ CDR3 comprising amino acids having the sequence set forth in SEQ ID NO: 11, a V$_L$ CDR1 comprising amino acids having the sequence set forth in SEQ ID NO: 12, a V$_L$ CDR2 comprising amino acids having the sequence set forth in SEQ ID NO: 14, and a V$_L$ CDR3 comprising amino acids having the sequence set forth in SEQ ID NO: 17.

TABLE 4

| Antigen | A CD56 polypeptide | | |
|---|---|---|---|
| CDRs | 1 | 2 | 3 |
| V$_H$ | GGTFTGYY [SEQ ID NO: 9] | INPNSGGT [SEQ ID NO: 10] | ARDLSSGYSGYFDY W [SEQ ID NO: 11] |
| V$_L$ | QSLLHSNGYNY [SEQ ID NO: 12] | LGS [SEQ ID NO: 14] | MQALQSPFTF [SEQ ID NO: 17] |
| Full V$_H$ | EVQLVQSGAEVKKPGSSVKVSCKASGGTFTGYYMHWVRQAPGQ GLEWMGWINPNSGGTNYAQKFQGRVTMTRDTSISTAYMELSRL RSDDTAVYYCARDLSSGYSGYFDYWGQGTLVTVSS [SEQ ID NO: 23] | | |
| DNA | GAAGTTCAGCTCGTCCAGTCCGGCGCTGAGGTCAAGAAGCCCG GGTCATCCGTGAAAGTCAGTTGTAAAGCTAGCGGAGGTACATT GTACGGATATTACATGCATTGGGTGCGGCAGGCGCCAGGCCAA GGACTCGAATGGATGGGATGGATCAATCCCAACTCAGGCGGAA CAAATTATGCTCAGAAATTCCAGGGTAGAGTGACTATGACTCG AGCAGGATACTTCAGCACAGCATACATGGAACTGTCACGGCTG CGATCCGACGACACTGCAGTGTACTATTGCGCCAGGGACCTCT CTTCAGGATACTCAGGTTACTTCGACTACTGGGGACAAGGCAC ACTCGTGACTGTATCTAGC [SEQ ID NO: 35] | | |
| Full V$_L$ | DVVMTQSPLSLPVTPGEPASISCRSSQSLLHSNGYNYLNWYLQ KPGQSPQLLIYLGSNRASGVPDRFSGSGSGTDFTLKISRVEGE DVGDYYCMQALQSPFTFGQGTKLEIKRTVA [SEQ ID NO: 24] | | |
| DNA | GATGTTGTTATGACCCAGAGCCCTTTGTCCCTCCCTGTAACCC CAGGTGAACCCGCAAGCATTTCATGTAGATCTTCTCAATCTCT TCTTCACAGCAATGGCTATAATTACTTGAATTGGTATCTCCAG AAGCCCGGTCAGTCCCCTCAACTTCTTATCTACTTGGGATCTA ACCGCGCATCCGGCGTGCCCGATCGATTTTCCGGATCAGGCAG ACACGGCACAGACTTTCTCAAAATCTCTAGAGTGGAAGGCGAA GATGTGGGCGACTATTACTGTATGCAGGCTTTGCAATCCCCCT TCACCTTTGGGCAGGGTACTAAACTTGAAATCAAAAGAACCGT AGCC [SEQ ID NO: 36] | | |
| scFv | EVQLVQSGAEVKKPGSSVKVSCKASGGTFTGYYMHWVRQAPGQ EGLWMGWINPNSGGTNYAQKFQGRVTMTRDTSISTAYMELSRL RSDDTAVYYCARDLSSGYSGYFDYWGQGTLVTVSSGGGGSGGG GSGGGGSDVVMTQSPLSLPVTPGEPASISCRSSQSLLHSNGYN YLNWYLQKPGQSPQLLIYLGSNRASGVPDRFSGSGSGTDFTLK | | |

TABLE 4-continued

ISRVEGEDVGDYYCMQALQSPFTFGQGTKLEIKRTVA
[SEQ ID NO: 42]

In certain embodiments, the extracellular antigen-binding domain is a human scFv, which comprises the amino acid sequence of SEQ ID NO: 43 and specifically binds to a CD56 polypeptide (e.g., a human CD56 polypeptide), which is designated as scFv m906.

In certain embodiments, the extracellular antigen-binding domain is a human scFv, which comprises a heavy chain variable region comprising amino acids having the sequence set forth in SEQ ID NO: 25 and a light chain variable region comprising amino acids having the sequence set forth in SEQ ID NO: 26, optionally with (iii) a linker sequence, for example a linker peptide, between the heavy chain variable region and the light chain variable region. In certain embodiments, the linker comprises amino acids having the sequence set forth in SEQ ID NO: 27. In certain embodiments, the extracellular antigen-binding domain is a human scFv-Fc fusion protein or full length human IgG with $V_H$ and $V_L$ regions or CDRs selected from Table 5. In certain embodiments, the extracellular antigen-binding domain comprises a $V_H$ comprising an amino acid sequence that is at least about 80% (e.g., at least about 85%, at least about 90%, or at least about 95%) homologous to SEQ ID NO: 25, as shown in Table 5. For example, the extracellular antigen-binding domain comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous to SEQ ID NO: 25. In certain embodiments the extracellular antigen-binding domain comprises a $V_H$ comprising amino acids having the sequence set forth in SEQ ID NO: 25. In certain embodiments, the extracellular antigen-binding domain comprises a $V_L$ comprising an amino acid sequence that is at least about 80% (e.g., at least about 85%, at least about 90%, or at least about 95%) homologous to SEQ ID NO: 26, as shown in Table 5. For example, the extracellular antigen-binding domain comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous to SEQ ID NO: 26. In certain embodiments, the extracellular antigen-binding domain comprises a $V_L$ comprising amino acids having the sequence set forth in SEQ ID NO: 26. In certain embodiments, the extracellular antigen-binding domain comprises a $V_H$ comprising an amino acid sequence that is at least about 80% (e.g., at least about 85%, at least about 90%, or at least about 95%) homologous to SEQ ID NO: 25, and a $V_L$ comprising an amino acid sequence that is at least about 80% (e.g., at least about 85%, at least about 90%, or at least about 95%) homologous to SEQ ID NO: 26. In certain embodiments, the extracellular antigen-binding domain comprises a $V_H$ comprising amino acids having the sequence set forth in SEQ ID NO: 25 and a $V_L$ comprising amino acids having the sequence set forth in SEQ ID NO: 26. In certain embodiments, the extracellular antigen-binding domain comprises a $V_H$ CDR1 comprising amino acids having the sequence set forth in SEQ ID NO: 9 or a conservative modification thereof, a $V_H$ CDR2 comprising amino acids having the sequence set forth in SEQ ID NO: 10 or a conservative modification thereof, and a $V_H$ CDR3 comprising amino acids having the sequence set forth in SEQ ID NO: 11 or a conservative modification thereof, as shown in Table 5. In certain embodiments, the extracellular antigen-binding domain comprises a $V_H$ CDR1 comprising amino acids having the sequence set forth in SEQ ID NO: 9, a $V_H$ CDR2 comprising amino acids having the sequence set forth in SEQ ID NO: 10, and a $V_H$ CDR3 comprising amino acids having the sequence set forth in SEQ ID NO: 11. In certain embodiments, the extracellular antigen-binding domain comprises a $V_L$ CDR1 comprising amino acids having the sequence set forth in SEQ ID NO: 13 or a conservative modification thereof, a $V_L$ CDR2 comprising amino acids having the sequence set forth in SEQ ID NO: 14 or a conservative modification thereof, and a $V_L$ CDR3 comprising amino acids having the sequence set forth in SEQ ID NO: 18 or a conservative modification thereof, as shown in Table 5. In certaine mbodiments, the extracellular antigen-binding domain comprises a $V_L$ CDR1 comprising amino acids having the sequence set forth in SEQ ID NO: 13, a $V_L$ CDR2 comprising amino acids having the sequence set forth in SEQ ID NO: 14, and a $V_L$ CDR3 comprising amino acids having the sequence set forth in SEQ ID NO: 18. In certainembodiments, the extracellular antigen-binding domain comprises a $V_H$ CDR1 comprising amino acids having the sequence set forth in SEQ ID NO: 9 or a conservative modification thereof, a $V_H$ CDR2 comprising amino acids having the sequence set forth in SEQ ID NO: 10 or a conservative modification thereof, a $V_H$ CDR3 comprising amino acids having the sequence set forth in SEQ ID NO: 11 or a conservative modification thereof, a $V_L$ CDR1 comprising amino acids having the sequence set forth in SEQ ID NO: 13 or a conservative modification thereof, a $V_L$ CDR2 comprising amino acids having the sequence set forth in SEQ ID NO: 14 or a conservative modification thereof, and a $V_L$ CDR3 comprising amino acids having the sequence set forth in SEQ ID NO: 18 or a conservative modification thereof, as shown in Table 5. In certain embodiments, the extracellular antigen-binding domain comprises a $V_H$ CDR1 comprising amino acids having the sequence set forth in SEQ ID NO: 9, a $V_H$ CDR2 comprising amino acids having the sequence set forth in SEQ ID NO: 10, a $V_H$ CDR3 comprising amino acids having the sequence set forth in SEQ ID NO: 11, a $V_L$ CDR1 comprising amino acids having the sequence set forth in SEQ ID NO: 13, a $V_L$ CDR2 comprising amino acids having the sequence set forth in SEQ ID NO: 14 or a conservative modification thereof, and a $V_L$ CDR3 comprising amino acids having the sequence set forth in SEQ ID NO: 18.

TABLE 5

| Antigen | A CD polypeptide | | |
|---|---|---|---|
| CDRs | 1 | 2 | 3 |
| $V_H$ | GGTFTGYY [SEQ ID NO: 9] | INPNSGGT [SEQ ID NO: 10] | ARDLSSGYSGYFDYW [SEQ ID NO: 11] |
| $V_L$ | QSLLHSNGYNF [SEQ ID NO: 13] | LGS [SEQ ID NO: 14] | MQSLQTPWTF [SEQ ID NO: 18] |
| Full $V_H$ | EVQLVQSGAEVKKPGSSVKVSCKASGGTFTGYYMHWVRQAPGQ GLEWMGWINPNSGGTNYAQKFQGRVTMTRDTSISTAYMELSRL RSDDTAVYYCARDLSSGYSGYFDYWGQGTLVTVSS [SEQ ID NO: 25] | | |

TABLE 5-continued

| | |
|---|---|
| DNA | GAAGTACAGTTGGTCCAAAGCGGCGCAGAAGTTAAGAAACCAG<br>GCTCCTCAGTTAAAGTCTCATGTAAAGCATCCGGCGGCACTTT<br>CACAGGGTACTATATGCATTGGGTCAGACAAGCACCAGGACAA<br>GGCCTCGAATGGATGGGTTGGATTAATCCTAATTCCGGTGGAA<br>CGAACTATGCACAGAAATTTCAAGGACGCGTAACGATGACACG<br>AGACACAAGTATATCAACAGCTTATATGGAACTCAGCAGATTG<br>CGATCAGACGACACGGCAGTATACTATTGCGCTCGAGATCTCT<br>CCTCTGGCTATTCAGGATACTTCGATTATTGGGGACAGGGCAC<br>TCTCGTCACAGTTTCTTCT [SEQ ID NO: 37] |
| Full<br>V$_L$ | DVVMTQSPLSLPVTPGEPASISCRSSQSLLHSNGYNFLDWYLQ<br>KPGQSPQLLIYLGSNRASGVPDRFSGSGSGTDFTLKISRVEAD<br>DVGVYYCMQSLQTPWTFGHGTKVEIKRTVA<br>[SEQ ID NO: 26] |
| DNA | GATGTGGTAATGACTCAAAGTCCTTTGTCCCTTCCTGTGACCC<br>CTGGAGAACCTGCCTCAATTTCCTGTAGATCTTCTCAAAGTCT<br>TCTTCACTCCAATGGATATAATTTTCTTGATTGGTATCTTCAA<br>AAACCCGGACAGTCCCCACAGTTGCTCATTTACCTGGGTTCTA<br>ATCGAGCCTCCGGCGTCCCAGACAGGTTTTCAGGTTCAGGCAG<br>TGGTACCGATTTCACACTTAAGATTTCTCGCGTCGAAGCCGAT<br>GATGTAGGCGTTTATTATTGTATGCAATCCCTTCAGACTCCTT<br>GGACTTTCGGTCATGGAACGAAAGTAGAAATTAAACGAACAGT<br>TGCA [SEQ ID NO: 38] |
| scFv | EVQLVQSGAEVKKPGSSVKVSCKASGGTFTGYYMHWVRQAPGQ<br>GLEWMGWINPNSGGTNYAQKFQGRVTMTRDTSISTAYMELSRL<br>RSDDTAVYYCARDLSSGYSGYFDYWGQGTLVTVSSGGGGSGGG<br>GSGGGGSDVVMTQSPLSLPVTPGEPASISCRSSQSLLHSNGYN<br>FLDWYLQKPGQSPQLLIYLGSNRASGVPDRFSGSGSGTDFTLK<br>ISRVEADDVGVYYCMQSLQTPWTFGHGTKVEIKRTVA<br>[SEQ ID NO: 43] |

As used herein, the term "a conservative sequence modification" refers to an amino acid modification that does not significantly affect or alter the binding characteristics of the presently disclosed CAR (e.g., the extracellular antigen-binding domain of the CAR) comprising the amino acid sequence. Conservative modifications can include amino acid substitutions, additions and deletions. Modifications can be introduced into the human scFv of the presently disclosed CAR by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (l) above) using the functional assays described herein. In certain embodiments, no more than one, no more than two, no more than three, no more than four, no more than five residues within a specified sequence or a CDR region are altered.

The $V_H$ and/or $V_L$ amino acid sequences having at least about 80%, at least about 85%, at least about 90%, or at least about 95% (e.g., about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%) homology to the specified sequences (e.g., SEQ ID NOs: 7, 8, 19, 20, 21, 22, 23, 24, 25, and 26) contain substitutions (e.g., conservative substitutions), insertions, or deletions relative to the specified sequence(s), but retain the ability to bind to CD56 (e.g., human CD56). In certain embodiments, the extracellular antigen-binding domain specifically binds to CD56 (e.g., human CD56) with a binding affinity ($K_d$) of about $3 \times 10^{-9}$ or less. In certain embodiments, the extracellular antigen-binding domain binds to CD56 (e.g., human CD56) with a binding affinity ($K_d$) of from about $3 \times 10^{-9}$ to about $2 \times 10^{-7}$. In certain embodiments, a total of 1 to 10 amino acids are substituted, inserted and/or deleted in SEQ ID NOs: 7, 8, 19, 20, 21, 22, 23, 24, 25, and 26. In certain embodiments, substitutions, insertions, or deletions occur in regions outside the CDRs (e.g., in the FRs) of the extracellular antigen-binding domain. In certain embodiments, the extracellular antigen-binding domain comprises $V_H$ and/or $V_L$ sequence selected from the group consisting of SEQ ID NOs: 7, 8, 19, 20, 21, 22, 23, 24, 25, and 26, including post-translational modifications of that sequence (SEQ ID NO: 7, 8, 19, 20, 21, 22, 23, 24, 25, or 26).

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm.

The percent homology between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent homology between two amino acid sequences can be determined using the Needleman and Wunsch (J. Mol. Biol. 48:444-453 (1970)) algorithm which has been incorporated into the GAP program in the GCG software package (available at www world wide web.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the amino acids sequences of the presently disclosed subject matter can further be used as a "query sequence" to perform a search against public databases to, for example, identify related sequences. Such searches can be performed using the)(BLAST program (version 2.0) of Altschul, et al. (1990) J. Mol. Biol. 215: 403-10. BLAST protein searches can be performed with the XBLAST program, score=50, wordlength=3 to obtain amino acid sequences homologous to the specified sequences (e.g., heavy and light chain variable region sequences of scFv m903, m904, m905, m906, and m900) disclosed herein. To obtain gapped alignments for comparison purposes, Gapped BLAST can be utilized as described in Altschul et al., (1997) Nucleic Acids Res. 25(17):3389-

3402. When utilizing BLAST and Gapped BLAST programs, the default parameters of the respective programs (e.g.,)(BLAST and NBLAST) can be used.

In certain embodiments, the extracellular antigen-binding domain of a presently disclosed CAR cross-competes for binding to CD56 (e.g., human CD56) with a reference antibody or an antigen-binding portion thereof comprising the $V_H$ CDR1, CDR2, and CDR3 sequences and the and $V_L$ CDR1, CDR2, and CDR3 sequences of, for example, any one of the presently disclosed scFvs (e.g., m903, m904, m905, m906, and m900). In certain embodiments, the extracellular antigen-binding domain of a presently disclosed CAR cross-competes for binding to CD56 (e.g., human CD56) with a reference antibody or an antigen-binding portion thereof comprising the $V_H$ and $V_L$ sequences of, for example, any one of the presently disclosed scFvs (e.g., m903, m904, m905, m906, and m900). In certain embodiments, the extracellular antigen-binding domain of a presently disclosed CAR cross-competes for binding to CD56 (e.g., human CD56) with a reference antibody or an antigen-binding portion thereof comprising the $V_H$ CDR1, CDR2, and CDR3 sequences and and the $V_L$ CDR1, CDR2, and CDR3 sequences of scFv m900. For example, the extracellular antigen-binding domain of a presently disclosed CAR cross-competes for binding to CD56 (e.g., human CD56) with a reference antibody or an antigen-binding portion thereof comprising a $V_H$ CDR1 comprising amino acids having the sequence set forth in SEQ ID NO: 1; a $V_H$ CDR2 comprising amino acids having the sequence set forth in SEQ ID NO: 2; a $V_H$ CDR3 comprising amino acids having the sequence set forth in SEQ ID NO: 3 or SEQ ID NO: 59; a $V_L$ CDR1 comprising amino acids having the sequence set forth in SEQ ID NO: 4; a $V_L$ CDR2 comprising amino acids having the sequence set forth in SEQ ID NO: 5; and a $V_L$ CDR3 comprising amino acids having the sequence set forth in SEQ ID NO: 6. In certain embodiments, the extracellular antigen-binding domain of a presently disclosed CAR cross-competes for binding to CD56 (e.g., human CD56) with a reference antibody or an antigen-binding portion thereof comprising the VH and $V_L$ sequences of scFv m900. For example, the extracellular antigen-binding domain of a presently disclosed CAR cross-competes for binding to CD56 (e.g., human CD56) with a reference antibody or an antigen-binding portion thereof comprising a $V_H$ comprising amino acids having the sequence set forth in SEQ ID NO: 7, and a $V_L$ comprising amino acids having the sequence set forth in SEQ ID NO: 8.

In certain embodiments, the extracellular antigen-binding domain binds to the same epitope on CD56 (e.g., human CD56) as the reference antibody or antigen-binding portion thereof. For example, the extracellular antigen-binding domain of a presently disclosed CAR binds to the same epitope on CD56 (e.g., human CD56) as a reference antibody or an antigen-binding portion thereof comprising the $V_H$ CDR1, CDR2, and CDR3 sequences and the $V_L$ CDR1, CDR2, and CDR3 sequences of, for example, any one of the presently disclosed scFvs (e.g., m903, m904, m905, m906, and m900). In certain embodiments, the extracellular antigen-binding domain of a presently disclosed CAR binds to the same epitope on CD56 (e.g., human CD56) as a reference antibody or an antigen-binding portion thereof comprising the $V_H$ and $V_L$ sequences of, for example, any one of the presently disclosed scFvs (e.g., m903, m904, m905, m906, and m900). In certain embodiments, the extracellular antigen-binding domain of a presently disclosed CAR binds to the same epitope on CD56 (e.g., human CD56) as a reference antibody or an antigen-binding portion thereof comprising the $V_H$ CDR1, CDR2, and CDR3 sequences and the $V_L$ CDR1, CDR2, and CDR3 sequences of scFv m900. For example, the extracellular antigen-binding domain of a presently disclosed CAR binds to the same epitope on CD56 (e.g., human CD56) as a reference antibody or an antigen-binding portion thereof comprising a $V_H$ CDR1 comprising amino acids having the sequence set forth in SEQ ID NO: 1; a $V_H$ CDR2 comprising amino acids having the sequence set forth in SEQ ID NO: 2; a $V_H$ CDR3 comprising amino acids having the sequence set forth in SEQ ID NO: 3 or SEQ ID NO: 59; a $V_L$ CDR1 comprising amino acids having the sequence set forth in SEQ ID NO: 4; a $V_L$ CDR2 comprising amino acids having the sequence set forth in SEQ ID NO: 5; and a $V_L$ CDR3 comprising amino acids having the sequence set forth in SEQ ID NO: 6. In certain embodiments, the extracellular antigen-binding domain of a presently disclosed CAR binds to the same or substantially the same epitope on CD56 (e.g., human CD56) as a reference antibody or an antigen-binding portion thereof comprising the $V_H$ and $V_L$ sequences of scFv m900 (which can also be referred to as m907). For example, the extracellular antigen-binding domain of a presently disclosed CAR binds to the same epitope on CD56 (e.g., human CD56) as a reference antibody or an antigen-binding portion thereof comprising a $V_H$ comprising amino acids having the sequence set forth in SEQ ID NO: 7, and a $V_L$ comprising amino acids having the sequence set forth in SEQ ID NO: 8.

Extracellular antigen-binding domains that cross-compete or compete with the reference antibody or antigen-binding portions thereof for binding to CD56 (e.g., human CD56) can be identified by using routine methods known in the art, including, but not limited to, ELISAs, radioimmunoassays (RIAs), Biacore, flow cytometry, Western blotting, and any other suitable quantitative or qualitative antibody-binding assays. Competition ELISA is described in Morris, "Epitope Mapping of Protein Antigens by Competition ELISA", *The Protein Protocols Handbook* (1996), pp 595-600, edited by J. Walker, which is incorporated by reference in its entirety. In certain embodiments, the antibody-binding assay comprises measuring an initial binding of a reference antibody to a CD56 polypeptide, admixing the reference antibody with a test extracellular antigen-binding domain, measuring a second binding of the reference antibody to the CD56 polypeptide in the presence of the test extracellular antigen-binding domain, and comparing the initial binding with the second binding of the reference antibody, wherein a decreased second binding of the reference antibody to the CD56 polypeptide in comparison to the initial binding indicates that the test extracellular antigen-binding domain cross-competes with the reference antibody for binding to CD56, e.g., one that recognizes the same or substantially the same epitope, an overlapping epitope, or an adjacent epitope. In certain embodiments, the reference antibody is labeled, e.g., with a fluorochrome, biotin, or peroxidase. In certain embodiments, the CD56 polypeptide is expressed in cells, e.g., in a flow cytometry test. In certain embodiments, the CD56 polypeptide is immobilized onto a surface, including a Biacore ship (e.g., in a Biacore test), or other media suitable for surface plasmon resonance analysis. The binding of the reference antibody in the presence of a completely irrelevant antibody (that does not bind to CD56) can serve as the control high value. The control low value can be obtained by incubating a labeled reference antibody with an unlabeled reference antibody, where competition and reduced binding of the labeled reference antibody would occur. In certain embodiments, a test extracellular antigen-binding domain that reduces the binding of the reference antibody to a CD56 polypeptide by at least about 20%, at least about 30%, at least about 40%, at least about 50%, at least about 60%, at least about 70%, at least about 80%, at least about 90%, or at least about 95% is considered to be an extracellular antigen-binding domain that cross-competes with the reference antibody for binding to CD56. In certain embodiments, the assays are performed at room temperature.

In certain embodiments, the antibody-binding assay comprises measuring an initial binding of a test extracellular antigen-binding domain to a CD56 polypeptide, admixing the test extracellular antigen-binding domain with a reference antibody, measuring a second binding of the test extracellular antigen-binding domain to the CD56 polypeptide in the presence of the reference antibody, and comparing the initial binding with the second binding of the test extracellular antigen-binding domain, where a decreased second binding of the test extracellular antigen-binding domain to the CD56 polypeptide in comparison to the initial binding indicates that the test extracellular antigen-binding domain cross-competes with the reference antibody for binding to CD56, e.g., one that recognizes the same or substantially the same epitope, an overlapping epitope, or an adjacent epitope. In certain embodiments, the test extracellular antigen-binding domain is labeled, e.g., with a fluorochrome, biotin, or peroxidase. In certain embodiments, the CD56 polypeptide is expressed in cells, e.g., in a flow cytometry test. In certain embodiments, the CD56 polypeptide is immobilized onto a surface, including a Biacore ship (e.g., in a Biacore test), or other media suitable for surface plasmon resonance analysis. The binding of the test extracellular antigen-binding domain in the presence of a completely irrelevant antibody (that does not bind to CD56) can serve as the control high value. The control low value can be obtained by incubating a labeled test extracellular antigen-binding domain with an unlabeled test extracellular antigen-binding domain, where competition and reduced binding of the labeled test extracellular antigen-binding domain would occur. In certain embodiments, a test extracellular antigen-binding domain, whose binding to a CD56 polypeptide is decreased by at least about 20%, at least about 30%, at least about 40%, at least about 50%, at least about 60%, at least about 70%, at least about 80%, at least about 90%, or at least about 95% in the presence of a reference antibody, is considered to be an extracellular antigen-binding domain that cross-competes with the reference antibody for binding to CD56. In certain embodiments, the assays are performed at room temperature.

It is well known in the art that the CDR3 domain, independently from the CDR1 and/or CDR2 domain(s), alone can determine the binding specificity of an antibody or an antigen-binding portion thereof, for a cognate antigen and that multiple antibodies can predictably be generated having the same binding specificity based on a common CDR3 sequence. See, for example, Klimka et al., *British J. of Cancer* 83(2):252-260 (2000) (describing the production of a humanized anti-CD30 antibody using only the heavy chain variable domain CDR3 of murine anti-CD30 antibody Ki-4); Beiboer et al., *J. Mol. Bioi.* 296:833-849 (2000) (describing recombinant epithelial glycoprotein-2 (EGP-2) antibodies using only the heavy chain CDR3 sequence of the parental murine MOC-31 anti-EGP-2 antibody); Rader et al., *Proc. Natl. Acad Sci. US.A.* 95:8910-8915 (1998) (describing a panel of humanized anti-integrin $\alpha v \beta_3$ antibodies using a heavy and light chain variable CDR3 domain of a murine anti-integrin $\alpha v \beta_3$ antibody LM609 wherein each member antibody comprises a distinct sequence outside the CDR3 domain and capable of binding the same epitope as the parent muring antibody with affinities as high or higher than the parent murine antibody); Barbas et al., *J. Am. Chem. Soc.* 116:2161-2162 (1994) (disclosing that the CDR3 domain provides the most significant contribution to antigen binding); Barbas et al., *Proc. Natl. Acad Sci. US.A.* 92:2529-2533 (1995) (describing the grafting of heavy chain CDR3 seqeunces of three Fabs (SI-1, SI-40, and SI-32) against human placental DNA onto the heavy chain of an anti-tetanus toxoid Fab thereby replacing the existing heavy chain CDR3 and demonstrating that the CDR3 domain alone conferred binding specificity); and Ditzel et ai., *J. Immunol.* 157:739-749 (1996) (describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab). Each of these references is hereby incorporated by reference in its entirety. In certain embodiments, the extracellular antigen-binding domain comprises a heavy chain variable region CDR3 comprising amino acids having the sequence set forth in SEQ ID NO: 3, a conservative modification of SEQ ID NO: 3, SEQ ID NO: 59, or a conservative modification of of SEQ ID NOL 59, and/or a light chain variable region CDR3 comprising amino acids having the sequence set forth in SEQ ID NO: 6 or a conservative modification thereof. The extracellular antigen-binding domain can comprise a heavy chain variable region CDR2 comprising amino acids having the sequence set forth in SEQ ID NO: 2 or a conservative modification thereof, and a light chain variable region CDR2 comprising amino acids having the sequence set forth in SEQ ID NO: 5 or a conservative modification thereof. The extracellular antigen-binding domain can further comprise a heavy chain variable region CDR1 comprising amino acids having the sequence set forth in SEQ ID NO: 1 or a conservative modification thereof, and a light chain variable region CDR1 comprising amino acids having the sequence set forth in SEQ ID NO: 4 or a conservative modification thereof.

In certain embodiments, the extracellular antigen-binding domain comprises a $V_H$ CDR1 comprising amino acids having the sequence set forth in SEQ ID NO: 9, a $V_H$ CDR2 comprising amino acids having the sequence set forth in SEQ ID NO: 10, a $V_H$ CDR3 comprising amino acids having the sequence set forth in SEQ ID NO: 11, a $V_L$ CDR1 comprising amino acids having the sequence set forth in SEQ ID NO: 12, a $V_L$ CDR2 comprising amino acids having the sequence set forth in SEQ ID NO: 14, and a $V_L$ CDR3 comprising amino acids having the sequence set forth in SEQ ID NO: 15.

Furthermore, in certain embodiments, the extracellular antigen-binding domain comprises a heavy chain variable region CDR3 comprising amino acids having the sequence set forth in SEQ ID NO: 11 or a conservative modification thereof; and a light chain variable region CDR3 comprising amino acids having a sequence selected from the group consisting of SEQ ID NO: 15, a conservative modification of of SEQ ID NO: 15, SEQ ID NO: 16, a conservative modification of of SEQ ID NO: 16, SEQ ID NO: 17, a conservative modification of of SEQ ID NO: 17, SEQ ID NO: 18, and a conservative modification of of SEQ ID NO: 18. In certain embodiments, the extracellular antigen-binding domain comprises a heavy chain variable region CDR3 comprising amino acids having the sequence set forth in SEQ ID NO: 11 or a conservative modification thereof; and a light chain variable region CDR3 comprising amino acids having the sequence set forth in SEQ ID NO: 15 or a conservative modification thereof. In certain embodiments, the extracellular antigen-binding domain comprises a heavy chain variable region CDR3 comprising amino acids having the sequence set forth in SEQ ID NO: 11 or a conservative modification thereof; and a light chain variable region CDR3 comprising amino acids having the sequence set forth in SEQ ID NO: 16 or a conservative modification thereof. In certain embodiments, the extracellular antigen-binding domain comprises a heavy chain variable region CDR3 comprising amino acids having the sequence set forth in SEQ ID NO: 11 or a conservative modification thereof; and a light chain variable region CDR3 comprising amino acids having the sequence set forth in SEQ ID NO: 17 or a conservative modification thereof. In certain embodiments, the extracellular antigen-binding domain comprises a heavy chain variable region CDR3 comprising amino acids having the sequence set forth in SEQ ID NO: 11 or a conservative modification thereof; and a light chain variable region CDR3 comprising amino acids having the sequence set forth in SEQ ID NO: 18 or a conservative modification thereof. The extracellular antigen-binding domain can further comprise: a heavy chain variable region CDR2 comprising amino acids having the sequence set forth in SEQ ID NO: 10 or a conservative modification thereof; and a light chain variable region CDR2 comprising amino acids having the sequence set forth in SEQ ID NO: 14. The extracellular antigen-binding domain can further comprise: a heavy chain variable region CDR1 comprising amino acids having the sequence set forth in SEQ ID NO: 9 or a conservative modification thereof; and a light chain variable region CDR1 comprising amino acids having a sequence selected from the group consisting of SEQ ID NO: 12 or a conservative modification thereof, and SEQ ID NO: 13 or a conservative modification thereof. In certain embodiments, the extracellular antigen-binding domain can further comprise: a heavy chain variable region CDR1 comprising amino acids having the sequence set forth in SEQ ID NO: 9 or a conservative modification thereof; and a light chain variable region CDR1 comprising amino acids having the set forth in SEQ ID NO: 12 or a conservative modification thereof. In certain embodiments, the extracellular antigen-binding domain can further comprise: a heavy chain variable region CDR1 comprising amino acids having the sequence set forth in SEQ ID NO: 9 or a conservative modification thereof; and a light chain variable region CDR1 comprising amino acids having the sequence set forth in SEQ ID NO: 13 or a conservative modification thereof.

In certain non-limiting embodiments, an extracellular antigen-binding domain of the presently disclosed CAR can comprise a linker connecting the heavy chain variable region and light chain variable region of the extracellular antigen-binding domain. As used herein, the term "linker" refers to a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple $V_H$ and $V_L$ domains). In certain embodiments, the linker comprises amino acids having the sequence set forth in SEQ ID NO: 27. In certain embodiments, the nucleotide sequence encoding the amino acid sequence of SEQ ID NO: 27 is set forth in SEQ ID NO: 28.

In addition, the extracellular antigen-binding domain can comprise a leader or a signal peptide that directs the nascent protein into the endoplasmic reticulum. Signal peptide or leader can be essential if the CAR is to be glycosylated and anchored in the cell membrane. The signal sequence or leader can be a peptide sequence (about 5, about 10, about 15, about 20, about 25, or about 30 amino acids long) present at the N-terminus of newly synthesized proteins that directs their entry to the secretory pathway. In certain embodiments, the signal peptide is covalently joined to the 5' terminus of the extracellular antigen-binding domain. In certain embodiments, the signal peptide comprises a CD8 polypeptide comprising amino acids having the sequence set forth in SEQ ID NO: 44 as provided below.

TAMALPVTALLLPLALLLHAARP      [SEQ ID NO: 44]

The nucleotide sequence encoding the amino acid sequence of SEQ ID NO: 44 is set forth in SEQ ID NO: 45, which is provided below:

[SEQ ID NO: 45]
ACTGCCATGGCCCTGCCAGTAACGGCTCTGCTGCTGCCACTTGCTCTGCT

CCTCCATGCAGCCAGGCCT

Transmembrane Domain of a CAR

In certain non-limiting embodiments, the transmembrane domain of the CAR comprises a hydrophobic alpha helix that spans at least a portion of the membrane. Different transmembrane domains result in different receptor stability. After antigen recognition, receptors cluster and a signal is transmitted to the cell. In accordance with the presently disclosed subject matter, the transmembrane domain of the CAR can comprise a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide (not based on a protein associated with the immune response), or a combination thereof.

In certain embodiments, the transmembrane domain of a presently disclosed CAR comprises a CD28 polypeptide. The CD28 polypeptide can have an amino acid sequence that is at least about 85%, about 90%, about 95%, about 96%, about 97%, about 98%, about 99% or 100% homologous to the sequence having a NCBI Reference No: P10747 or NP_006130 (SEQ ID No:46), or fragments thereof, and/or may optionally comprise up to one or up to two or up to three conservative amino acid substitutions. In certain embodiments, the CD28 polypeptide can have an amino acid sequence that is a consecutive portion of SEQ ID NO: 46 which is at least 20, or at least 30, or at least 40, or at least 50, and up to 220 amino acids in length. Alternatively or additionally, in non-limiting various embodiments, the CD28 polypeptide has an amino acid sequence of amino acids 1 to 220, 1 to 50, 50 to 100, 100 to 150, 114 to 220, 150 to 200, or 200 to 220 of SEQ ID NO: 46. In certain embodiments, the CAR of the presently disclosed comprises a transmembrane domain comprising a CD28 polypeptide, and an intracellular domain comprising a co-stimulatory signaling region that comprises a CD28 polypeptide. In certain embodiments, the CD28 polypeptide comprised in the transmembrane domain and the intracellular domain has an amino acid sequence of amino acids 114 to 220 of SEQ ID NO: 46.

SEQ ID NO: 46 is provided below:

```
                                                              [SEQ ID NO: 46]
  1 MLRLLLALNL FPSIQVTGNK ILVKQSPMLV AYDNAVNLSC KYSYNLFSRE FRASLHKGLD

61 SAVEVCVVYG NYSQQLQVYS KTGFNCDGKL GNESVTFYLQ NLYVNQTDIY FCKIEVMYPP

121 PYLDNEKSNG TIIHVKGKHL CPSPLFPGPS KPFWVLVVVG GVLACYSLLV TVAFIIFWVR

181 SKRSRLLHSD YMNMTPRRPG PTRKHYQPYA PPRDFAAYRS
```

In accordance with the presently disclosed subject matter, a "CD28 nucleic acid molecule" refers to a polynucleotide encoding a CD28 polypeptide. In certain embodiments, the CD28 nucleic acid molecule encoding the CD28 polypeptide comprised in the transmembrane domain and the intracellular domain (e.g., the co-stimulatory signaling region) of the presently disclosed CAR (amino acids 114 to 220 of SEQ ID NO: 46) comprises nucleic acids having the sequence set forth in SEQ ID NO: 47 as provided below.

```
                                                [SEQ ID NO: 47]
attgaagttatgtatcctcctccttacctagacaatgagaagagcaatgg aaccattatccatgtgaaagggaaacacctttgtccaagtcccctatttc ccggaccttctaagccctttttgggtgctggtggtggttggtggagtcctg gcttgctatagcttgctagtaacagtggcctttattattttctgggtgag gagtaagaggagcaggctcctgcacagtgactacatgaacatgactcccc gccgccccgggcccacccgcaagcattaccagccctatgccccaccacg gacttcgcagcctatcgctcc
```

In certain embodiments, the transmembrane domain comprises a CD8 polypeptide. The CD8 polypeptide can have an amino acid sequence that is at least about 85%, about 90%, about 95%, about 96%, about 97%, about 98%, about 99% or about 100% homologous to SEQ ID NO: 58 (homology herein may be determined using standard software such as BLAST or FASTA) as provided below, or fragments thereof, and/or may optionally comprise up to one or up to two or up to three conservative amino acid substitutions. In certain embodiments, the CD8 polypeptide can have an amino acid sequence that is a consecutive portion of SEQ ID NO: 58 which is at least 20, or at least 30, or at least 40, or at least 50, and up to 235 amino acids in length. Alternatively or additionally, in non-limiting various embodiments, the CD8 polypeptide has an amino acid sequence of amino acids 1 to 235, 1 to 50, 50 to 100, 100 to 150, 150 to 200, or 200 to 235 of SEQ ID NO: 60.

```
                                                [SEQ ID NO: 60]
MALPVTALLLPLALLLHAARPSQFRVSPLDRTWNLGETVELKCQVLLSNP

TSGCSWLFQPRGAAASPTFLLYLSQNKPKAAEGLDTQRFSGKRLGDTFVL

TLSDFRRENEGYYFCSALSNSIMYFSHFVPVFLPAKPTTTPAPRPPTPAP

TIASQPLSLRPEACRPAAGGAVHTRGLDFACDIYIWAPLAGTCGVLLLSL

VITLYCNHRNRRRVCKCPRPVVKSGDKPSLSARYV
```

In accordance with the presently disclosed subject matter, a "CD8 nucleic acid molecule" refers to a polynucleotide encoding a CD8 polypeptide.

In certain non-limiting embodiments, a CAR can also comprise a spacer region that links the extracellular antigen-binding domain to the transmembrane domain. The spacer region can be flexible enough to allow the antigen-binding domain to orient in different directions to facilitate antigen recognition while preserving the activating activity of the CAR. In certain non-limiting embodiments, the spacer region can be the hinge region from IgG1, the $CH_2CH_3$ region of immunoglobulin and portions of CD3, a portion of a CD28 polypeptide (e.g., SEQ ID NO:46), a portion of a CD8 polypeptide (e.g., SEQ ID NO: 60), a variation of any of the foregoing which is at least about 80%, at least about 85%, at least about 90%, or at least about 95% homologous thereto, or a synthetic spacer sequence. In certain non-limiting embodiments, the spacer region may have a length between about 1-50 (e.g., 5-25, 10-30, or 30-50) amino acids.

Intracellular Domain of a CAR

In certain non-limiting embodiments, an intracellular domain of the CAR can comprise a CD3ζ polypeptide, which can activate or stimulate a cell (e.g., a cell of the lymphoid lineage, e.g., a T cell). CD3ζ comprises 3 ITAMs, and transmits an activation signal to the cell (e.g., a cell of the lymphoid lineage, e.g., a T cell) after antigen is bound. The CD3π polypeptide can have an amino acid sequence that is at least about 85%, about 90%, about 95%, about 96%, about 97%, about 98%, about 99% or about 100% homologous to the sequence having a NCBI Reference No: NP 932170 (SEQ ID No: 48), or fragments thereof, and/or may optionally comprise up to one or up to two or up to three conservative amino acid substitutions. In non-limiting certain embodiments, the CD3ζ polypeptide can have an amino acid sequence that is a consecutive portion of SEQ ID NO: 25 which is at least 20, or at least 30, or at least 40, or at least 50, and up to 164 amino acids in length. Alternatively or additionally, in non-limiting various embodiments, the CD3t polypeptide has an amino acid sequence of amino acids 1 to 164, 1 to 50, 50 to 100, 100 to 150, or 150 to 164 of SEQ ID NO: 48. In certain embodiments, the CD3ζ polypeptide has an amino acid sequence of amino acids 52 to 164 of SEQ ID NO: 48.

SEQ ID NO: 48 is provided below:

```
                                                              [SEQ ID NO: 48]
  1 MKWKALFTAA ILQAQLPITE AQSFGLLDPK LCYLLDGILF IYGVILTALF LRVKFSRSAD

61 APAYQQGQNQ LYNELNLGRR EEYDVLDKRR GRDPEMGGKP QRRKNPQEGL YNELQKDKMA

121 EAYSEIGMKG ERRRGKGHDG LYQGLSTATK DTYDALHMQA LPPR
```

In certain embodiments, the CD3ζ polypeptide has the amino acid sequence set forth in SEQ ID NO: 58, which is provided below:

[SEQ ID NO: 58]
RVKFSRSAEPPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

In accordance with the presently disclosed subject matter, a "CD3ζ nucleic acid molecule" refers to a polynucleotide encoding a CD3t polypeptide. In certain embodiments, the CD3ζ nucleic acid molecule encoding the CD3ζ polypeptide comprised in the intracellular domain of the presently disclosed CAR (SEQ ID NO: 58) comprises a nucleotide sequence as set forth in SEQ ID NO: 49 as provided below.

[SEQ ID NO: 49]
agagtgaagttcagcaggagcgcagagccccccgcgtaccagcagggcca gaaccagctctataacgagctcaatctaggacgaagagaggagtacgatg ttttggacaagagacgtggccgggaccctgagatggggggaaagccgaga aggaagaaccctcaggaaggcctgtacaatgaactgcagaaagataagat ggcggaggcctacagtgagattgggatgaaaggcgagcgccggaggggca aggggcacgatggcctttaccagggtctcagtacagccaccaaggacacc tacgacgccttcacatgcaggccctgccccctcgcg In certain non-limiting embodiments, an intracellular domain of the CAR further comprises at least one signaling region. The at least one signaling region can include a a CD28 polypeptide, a 4-1BB polypeptide, an OX40 polypeptide, an ICOS polypeptide, a DAP-10 polypeptide, a PD-1 polypeptide, a CTLA-4 polypeptide, a LAG-3 polypeptide, a 2B4 polypeptide, a BTLA polypeptide, a synthetic peptide (not based on a protein associated with the immune response), or a combination thereof.

In certain embodiments, the signaling region is a co-stimulatory signaling region. In certain embodiments, the co-stimulatory signaling region comprises at least one co-stimulatory molecule, which can provide optimal lymphocyte activation. As used herein, "co-stimulatory molecules" refer to cell surface molecules other than antigen receptors or their ligands that are required for an efficient response of lymphocytes to antigen. The at least one co-stimulatory signaling region can include a CD28 polypeptide, a 4-1BB polypeptide, an OX40 polypeptide, an ICOS polypeptide, a DAP-10 polypeptide, or a combination thereof. The co-stimulatory molecule can bind to a co-stimulatory ligand, which is a protein expressed on cell surface that upon binding to its receptor produces a co-stimulatory response, i.e., an intracellular response that effects the stimulation provided when an antigen binds to its CAR molecule. Co-stimulatory ligands, include, but are not limited to CD80, CD86, CD70, OX40L, 4-1BBL, CD48, TNFRSF14, and PD-L1. As one example, a 4-1BB ligand (i.e., 4-1BBL) may bind to 4-1BB (also known as "CD137") for providing an intracellular signal that in combination with a CAR signal induces an effector cell function of the CAR$^+$ T cell. CARs comprising an intracellular domain that comprises a co-stimulatory signaling region comprising 4-1BB, ICOS or DAP-10 are disclosed in U.S. Pat. No. 7,446,190 (e.g., the nucleotide sequence encoding 4-1BB is set forth in SEQ ID NO:15, the nucleotide sequence encoding ICOS is set forth in SEQ ID NO:16, and the nucleotide sequence encoding DAP-10 is set forth in SEQ ID NO:17 in U.S. Pat. No. 7,446,190), which is herein incorporated by reference in its entirety. In certain embodiments, the intracellular domain of the CAR comprises a co-stimulatory signaling region that comprises a CD28 polypeptide. In certain embodiments, the intracellular domain of the CAR comprises a co-stimulatory signaling region that comprises two co-stimulatory molecules: CD28 and 4-1BB or CD28 and OX40.

4-1BB can act as a tumor necrosis factor (TNF) ligand and have stimulatory activity. The 4-1BB polypeptide can have an amino acid sequence that is at least about 85%, about 90%, about 95%, about 96%, about 97%, about 98%, about 99% or 100% homologous to the sequence having a NCBI Reference No: P41273 or NP_001552 (SEQ ID NO: 50) or fragments thereof, and/or may optionally comprise up to one or up to two or up to three conservative amino acid substitutions.

SEQ ID NO: 50 is provided below:

[SEQ ID NO: 50]
```
  1 MGNSCYNIVA TLLLVLNFER TRSLQDPCSN CPAGTFCDNN RNQICSPCPP NSFSSAGGQR

61 TCDICRQCKG VFRTRKECSS TSNAECDCTP GFHCLGAGCS MCEQDCKQGQ ELTKKGCKDC

121 CFGTFNDQKR GICRPWTNCS LDGKSVLVNG TKERDVVCGP SPADLSPGAS SVTPPAPARE

181 PGHSPQIISF FLALTSTALL FLLFFLTLRF SVVKRGRKKL LYIFKQPFMR PVQTTQEEDG

241 CSCRFPEEEE GGCEL
```

In accordance with the presently disclosed subject matter, a "4-1BB nucleic acid molecule" refers to a polynucleotide encoding a 4-1BB polypeptide.

An OX40 polypeptide can have an amino acid sequence that is at least about 85%, about 90%, about 95%, about 96%, about 97%, about 98%, about 99% or 100% homologous to the sequence having a NCBI Reference No: P43489 or NP 003318 (SEQ ID NO: 51), or fragments thereof, and/or may optionally comprise up to one or up to two or up to three conservative amino acid substitutions.

SEQ ID NO: 51 is provided below:

[SEQ ID NO: 51]
```
 1 MCVGARRLGR GPCAALLLLG LGLSTVTGLH CVGDTYPSND RCCHECRPGN GMVSRCSRSQ

61 NTVCRPCGPG FYNDVVSSKP CKPCTWCNLR SGSERKQLCT ATQDTVCRCR AGTQPLDSYK
```

-continued

```
121 PGVDCAPCPP GHFSPGDNQA CKPWTNCTLA GKHTLQPASN SSDAICEDRD PPATQPQETQ

181 GPPARPITVQ PTEAWPRTSQ GPSTRPVEVP GGRAVAAILG LGLVLGLLGP LAILLALYLL

241 RRDQRLPPDA HKPPGGGSFR TPIQEEQADA HSTLAKI
```

In accordance with the presently disclosed subject matter, an "OX40 nucleic acid molecule" refers to a polynucleotide encoding an OX40 polypeptide.

An ICOS polypeptide can have an amino acid sequence that is at least about 85%, about 90%, about 95%, about 96%, about 97%, about 98%, about 99% or 100% homologous to the sequence having a NCBI Reference No: NP 036224 (SEQ ID NO: 52) or fragments thereof, and/or may optionally comprise up to one or up to two or up to three conservative amino acid substitutions.

SEQ ID NO: 52 is provided below:

```
                                                            [SEQ ID NO: 52]
  1 MKSGLWYFFL FCLRIKVLTG EINGSANYEM FIFHNGGVQI LCKYPDIVQQ FKMQLLKGGQ

61 ILCDLIKTKG SGNTVSIKSL KFCHSQLSNN SVSFFLYNLD HSHANYYFCN LSIFDPPPFK

121 VTLTGGYLHI YESQLCCQLK FWLPIGCAAF VVVCILGCIL ICWLTKKKYS SSVHDPNGEY

181 MFMRAVNTAK KSRLTDVTL
```

In accordance with the presently disclosed subject matter, an "ICOS nucleic acid molecule" refers to a polynucleotide encoding an ICOS polypeptide.

CTLA-4 is an inhibitory receptor expressed by activated T cells, which when engaged by its corresponding ligands (CD80 and CD86; B7-1 and B7-2, respectively), mediates activated T cell inhibition or anergy. In both preclinical and clinical studies, CTLA-4 blockade by systemic antibody infusion, enhanced the endogenous anti-tumor response albeit, in the clinical setting, with significant unforeseen toxicities.

CTLA-4 contains an extracellular V domain, a transmembrane domain, and a cytoplasmic tail. Alternate splice variants, encoding different isoforms, have been characterized. The membrane-bound isoform functions as a homodimer interconnected by a disulfide bond, while the soluble isoform functions as a monomer. The intracellular domain is similar to that of CD28, in that it has no intrinsic catalytic activity and contains one YVKM motif able to bind PI3K, PP2A and SHP-2 and one proline-rich motif able to bind SH3 containing proteins. One role of CTLA-4 in inhibiting T cell responses seem to be directly via SHP-2 and PP2A dephosphorylation of TCR-proximal signaling proteins such as CD3 and LAT. CTLA-4 can also affect signaling indirectly via competing with CD28 for CD80/86 binding. CTLA-4 has also been shown to bind and/or interact with PI3K, CD80, AP2M1, and PPP2R5A.

In accordance with the presently disclosed subject matter, a CTLA-4 polypeptide can have an amino acid sequence that is at least about 85%, about 90%, about 95%, about 96%, about 97%, about 98%, about 99% or about 100% homologous to UniProtKB/Swiss-Prot Ref. No.: P16410.3 (SEQ ID NO: 53) (homology herein may be determined using standard software such as BLAST or FASTA) or fragments thereof, and/or may optionally comprise up to one or up to two or up to three conservative amino acid substitutions.

SEQ ID NO: 53 is provided below:

```
                                                            [SEQ ID NO: 53]
  1 MACLGFQRHK AQLNLATRTW PCTLLFFLLF IPVFCKAMHV AQPAVVLASS RGIASFVCEY

61 ASPGKATEVR VTVLRQADSQ VTEVCAATYM MGNELTFLDD SICTGTSSGN QVNLTIQGLR

121 AMDTGLYICK VELMYPPPYY LGIGNGTQIY VIDPEPCPDS DFLLWILAAV SSGLFFYSFL

181 LTAVSLSKML KKRSPLTTGV YVKMPPTEPE CEKQFQPYFI PIN
```

In accordance with the presently disclosed subject matter, a "CTLA-4 nucleic acid molecule" refers to a polynucleotide encoding a CTLA-4 polypeptide.

PD-1 is a negative immune regulator of activated T cells upon engagement with its corresponding ligands PD-L1 and PD-L2 expressed on endogenous macrophages and dendritic cells. PD-1 is a type I membrane protein of 268 amino acids. PD-1 has two ligands, PD-L1 and PD-L2, which are members of the B7 family. The protein's structure comprises an extracellular IgV domain followed by a transmembrane region and an intracellular tail. The intracellular tail contains two phosphorylation sites located in an immunoreceptor tyrosine-based inhibitory motif and an immunoreceptor tyrosine-based switch motif, that PD-1 negatively regulates TCR signals. SHP-1 and SHP-2 phosphatases bind to the cytoplasmic tail of PD-1 upon ligand binding. Upregulation of PD-L1 is one mechanism tumor cells may evade the host immune system. In pre-clinical and clinical trials, PD-1 blockade by antagonistic antibodies induced anti-tumor responses mediated through the host endogenous immune system.

In accordance with the presently disclosed subject matter, a PD-1 polypeptide can have an amino acid sequence that is at least about 85%, about 90%, about 95%, about 96%, about 97%, about 98%, about 99% or about 100% homologous to NCBI Reference No: NP 005009.2 (SEQ ID NO: 54) or fragments thereof, and/or may optionally comprise up to one or up to two or up to three conservative amino acid substitutions.

SEQ ID NO: 54 is provided below:

[SEQ ID NO: 54]
```
  1 MQIPQAPWPV VWAVLQLGWR PGWFLDSPDR PWNPPTFSPA LLVVTEGDNA TFTCSFSNTS

61 ESFVLNWYRM SPSNQTDKLA AFPEDRSQPG QDCRFRVTQL PNGRDFHMSV VRARRNDSGT

121 YLCGAISLAP KAQIKESLRA ELRVTERRAE VPTAHPSPSP RPAGQFQTLV VGVVGGLLGS

181 LVLLVWVLAV ICSRAARGTI GARRTGQPLK EDPSAVPVFS VDYGELDFQW REKTPEPPVP

241 CVPEQTEYAT IVFPSGMGTS SPARRGSADG PRSAQPLRPE DGHCSWPL
```

In accordance with the presently disclosed subject matter, a "PD-1 nucleic acid molecule" refers to a polynucleotide encoding a PD-1 polypeptide.

Lymphocyte-activation protein 3 (LAG-3) is a negative immune regulator of immune cells. LAG-3 belongs to the immunoglobulin (Ig) superfamily and contains 4 extracellular Ig-like domains. The LAG3 gene contains 8 exons. The sequence data, exon/intron organization, and chromosomal localization all indicate a close relationship of LAG3 to CD4. LAG3 has also been designated CD223 (cluster of differentiation 223).

In accordance with the the presently disclosed subject matter, a LAG-3 polypeptide can have an amino acid sequence that is at least about 85%, about 90%, about 95%, about 96%, about 97%, about 98%, about 99% or about 100% homologous to UniProtKB/Swiss-Prot Ref. No.: P18627.5 (SEQ ID NO: 55) or fragments thereof, and/or may optionally comprise up to one or up to two or up to three conservative amino acid substitutions.

SEQ ID NO: 55 is provided below:

[SEQ ID NO: 55]
```
  1 MWEAQFLGLL FLQPLWVAPV KPLQPGAEVP VVWAQEGAPA QLPCSPTIPL QDLSLLRRAG

61 VTWQHQPDSG PPAAAPGHPL APGPHPAAPS SWGPRPRRYT VLSVGPGGLR SGRLPLQPRV

121 QLDERGRQRG DFSLWLRPAR RADAGEYRAA VHLRDRALSC RLRLRLGQAS MTASPPGSLR

181 ASDWVILNCS FSRPDRPASV HWFRNRGQGR VPVRESPHHH LAESFLFLPQ VSPMDSGPWG

241 CILTYRDGFN VSIMYNLTVL GLEPPTPLTV YAGAGSRVGL PCRLPAGVGT RSFLTAKWTP

301 PGGGPDLLVT GDNGDFTLRL EDVSQAQAGT YTCHIHLQEQ QLNATVTLAI ITVTPKSFGS

361 PGSLGKLLCE VTPVSGQERF VWSSLDTPSQ RSFSGPWLEA QEAQLLSQPW QCQLYQGERL

421 LGAAVYFTEL SSPGAQRSGR APGALPAGHL LLFLILGVLS LLLLVTGAFG FHLWRRQWRP

481 RRFSALEQGI HPPQAQSKIE ELEQEPEPEP EPEPEPEPEP EPEQL
```

In accordance with the presently disclosed subject matter, a "LAG-3 nucleic acid molecule" refers to a polynucleotide encoding a LAG-3 polypeptide.

Natural Killer Cell Receptor 2B4 (2B4) mediates non-MHC restricted cell killing on NK cells and subsets of T cells. To date, the function of 2B4 is still under investigation, with the 2B4-S isoform believed to be an activating receptor, and the 2B4-L isoform believed to be a negative immune regulator of immune cells. 2B4 becomes engaged upon binding its high-affinity ligand, CD48. 2B4 contains a tyrosine-based switch motif, a molecular switch that allows the protein to associate with various phosphatases. 2B4 has also been designated CD244 (cluster of differentiation 244).

In accordance with the presently disclosed subject matter, a 2B4 polypeptide can have an amino acid sequence that is at least about 85%, about 90%, about 95%, about 96%, about 97%, about 98%, about 99% or about 100% homologous to UniProtKB/Swiss-Prot Ref. No.: Q9BZW8.2 (SEQ ID NO: 56) or fragments thereof, and/or may optionally comprise up to one or up to two or up to three conservative amino acid substitutions.

SEQ ID NO: 56 is provided below:

[SEQ ID NO: 56]
```
  1 MLGQVVTLIL LLLLKVYQGK GCQGSADHVV SISGVPLQLQ PNSIQTKVDS IAWKKLLPSQ

61 NGFHHILKWE NGSLPSNTSN DRFSFIVKNL SLLIKAAQQQ DSGLYCLEVT SISGKVQTAT

121 FQVFVFESLL PDKVEKPRLQ GQGKILDRGR CQVALSCLVS RDGNVSYAWY RGSKLIQTAG

181 NLTYLDEEVD INGTHTYTCN VSNPVSWESH TLNLTQDCQN AHQEFRFWPF LVIIVILSAL
```

-continued
```
241 FLGTLACFCV WRRKRKEKQS ETSPKEFLTI YEDVKDLKTR RNHEQEQTFP GGGSTIYSMI

301 QSQSSAPTSQ EPAYTLYSLI QPSRKSGSRK RNHSPSFNST IYEVIGKSQP KAQNPARLSR

361 KELENFDVYS
```

In accordance with the presently disclosed subject matter, a "2B4 nucleic acid molecule" refers to a polynucleotide encoding a 2B4 polypeptide.

B- and T-lymphocyte attenuator (BTLA) expression is induced during activation of T cells, and BTLA remains expressed on Th1 cells but not Th2 cells. Like PD1 and CTLA4, BTLA interacts with a B7 homolog, B7H4. However, unlike PD-1 and CTLA-4, BTLA displays T-Cell inhibition via interaction with tumor necrosis family receptors (TNF-R), not just the B7 family of cell surface receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses. BTLA activation has been shown to inhibit the function of human CD8$^+$ cancer-specific T cells. BTLA has also been designated as CD272 (cluster of differentiation 272).

In accordance with the presently disclosed subject matter, a BTLA polypeptide can have an amino acid sequence that is at least about 85%, about 90%, about 95%, about 96%, about 97%, about 98%, about 99% or about 100% homologous to UniProtKB/Swiss-Prot Ref. No.: Q7Z6A9.3 (SEQ ID NO: 57) or fragments thereof, and/or may optionally comprise up to one or up to two or up to three conservative amino acid substitutions.

SEQ ID NO: 57 is provided below:

```
                                                                [SEQ ID NO: 57]
  1 MKTLPAMLGT GKLFWVFFLI PYLDIWNIHG KESCDVQLYI KRQSEHSILA GDPFELECPV

61 KYCANRPHVT WCKLNGTTCV KLEDRQTSWK EEKNISFFIL HFEPVLPNDN GSYRCSANFQ

121 SNLIESHSTT LYVTDVKSAS ERPSKDEMAS RPWLLYRLLP LGGLPLLITT CFCLFCCLRR

181 HQGKQNELSD TAGREINLVD AHLKSEQTEA STRQNSQVLL SETGIYDNDP DLCFRMQEGS

241 EVYSNPCLEE NKPGIVYASL NHSVIGPNSR LARNVKEAPT EYASICVRS
```

In accordance with the presently disclosed subject matter, a "BTLA nucleic acid molecule" refers to a polynucleotide encoding a BTLA polypeptide.

In certain embodiments, the CAR comprises an extracellular antigen-binding region that comprises a human scFv that specifically binds to a human CD56 polypeptide, a transmembrane domain comprising a CD28 polypeptide, and an intracellular domain comprising a CD3ζ polypeptide and a co-stimulatory signaling region that comprises a CD28 polypeptide, as shown in FIG. 1. As shown in FIG. 1, the CAR also comprises a signal peptide or a leader covalently joined to the 5' terminus of the extracellular antigen-binding domain. The signal peptide comprises amino acids having the sequence set forth in SEQ ID NO: 50. In certain embodiments, the human scFv is selected from the group consisting of scFv m903, m904, m905, m906, and m900, whose variable region sequences are provided in Tables 1-5. In certain embodiments, the human scFv is scFv m900 (which can also be referred to as m907), whose variable region sequences are provided in Table 1.

In some embodiments, the CAR of the presently disclosed subject matter can further comprise an inducible promoter, for expressing nucleic acid sequences in human cells. Promoters for use in expressing CAR genes can be a constitutive promoter, such as ubiquitin C (UbiC) promoter.

The presently disclosed subject matter also provides isolated nucleic acid molecule encoding the CD56-targeted CAR described herein or a functional portion thereof. In certain embodiments, the isolated nucleic acid molecule encodes a presently disclosed CD56-targeted CAR comprising a human scFv that specifically binds to a human CD56 polypeptide, a transmembrane domain comprising a CD28 polypeptide, and an intracellular domain comprising a CD3ζ polypeptide and a co-stimulatory signaling region comprising a CD28 polypeptide.

In certain embodiments, an isolated nucleic acid molecule encodes a CD56-targeted CAR (designated as CD56-targeted CAR m903) comprising a human scFv that comprises a heavy chain variable region comprising amino acids having the sequence set forth in SEQ ID NO: 19, a light chain variable region comprising amino acids having the sequence set forth in SEQ ID NO: 20, and a linker having an amino acid sequence of SEQ ID NO: 27 positioned between the heavy chain variable region and the light chain variable region, a transmembrane domain comprising a CD28 polypeptide, and an intracellular domain comprising a CD3 polypeptide comprising the amino acid sequence set forth in SEQ ID NO: 58, and a co-stimulatory signaling region comprising a CD28 polypeptide, wherein the CD28 region comprising the transmembrane domain and the co-stimulatory signaling region comprises amino acids 114 to 220 of SEQ ID NO: 46.

In certain embodiments, an isolated nucleic acid molecule encodes a CD56-targeted CAR (designated as CD56-targeted CAR m904) comprising a human scFv that comprises a heavy chain variable region comprising amino acids having the sequence set forth in SEQ ID NO: 21, a light chain variable region comprising amino acids having the sequence set forth in SEQ ID NO: 22, and a linker having an amino acid sequence of SEQ ID NO: 27 positioned between the heavy chain variable region and the light chain variable region, a transmembrane domain comprising a CD28 polypeptide, and an intracellular domain comprising a CD3ζ polypeptide comprising the amino acid sequence set forth in SEQ ID NO: 58, and a co-stimulatory signaling region comprising a CD28 polypeptide, wherein the CD28 region comprising the transmembrane domain and the co-stimulatory signaling region comprises amino acids 114 to 220 of SEQ ID NO: 46.

In certain embodiments, an isolated nucleic acid molecule encodes a CD56-targeted CAR (designated as CD56-targeted CAR m905) comprising a human scFv that a heavy chain variable region comprising amino acids having the sequence set forth in SEQ ID NO: 23 a light chain variable region comprising amino acids having the sequence set forth in SEQ ID NO: 24 and a linker having an amino acid sequence of SEQ ID NO: 27 positioned between the heavy chain variable region and the light chain variable region, a transmembrane domain comprising a CD28 polypeptide, and an intracellular domain comprising a CD3 polypeptide comprising the amino acid sequence set forth in SEQ ID NO: 58, and a co-stimulatory signaling region comprising a CD28 polypeptide, wherein the CD28 region comprising the transmembrane domain and the co-stimulatory signaling region comprises amino acids 114 to 220 of SEQ ID NO: 46.

In certain embodiments, an isolated nucleic acid molecule ncodes a CD56-targeted CAR (designated as CD56-targeted CAR m906) comprising a human scFv that comprises a heavy chain variable region comprising amino acids having the sequence set forth in SEQ ID NO: 25 a light chain variable region comprising amino acids having the sequence set forth in SEQ ID NO: 26 and a linker having an amino acid sequence of SEQ ID NO: 27 positioned between the heavy chain variable region and the light chain variable region, a transmembrane domain comprising a CD28 polypeptide, and an intracellular domain comprising a CD3 polypeptide comprising the amino acid sequence set forth in SEQ ID NO: 58, and a co-stimulatory signaling region comprising a CD28 polypeptide, wherein the CD28 region comprising the transmembrane domain and the co-stimulatory signaling region comprises amino acids 114 to 220 of SEQ ID NO: 46.

In certain embodiments, an isolated nucleic acid molecule encodes a CD56-targeted CAR (designated as CD56-targeted CAR m900 (which can also be referred to as m907)) comprising a human scFv that comprises a heavy chain variable region comprising amino acids having the sequence set forth in SEQ ID NO: 7 a light chain variable region comprising amino acids having the sequence set forth in SEQ ID NO: 8 and a linker having an amino acid sequence of SEQ ID NO: 27 positioned between the heavy chain variable region and the light chain variable region, a transmembrane domain comprising a CD28 polypeptide, and an intracellular domain comprising a CD3 polypeptide comprising the amino acid sequence set forth in SEQ ID NO: 58, and a co-stimulatory signaling region comprising a CD28 polypeptide, wherein the CD28 region comprising the transmembrane domain and the co-stimulatory signaling region comprises amino acids 114 to 220 of SEQ ID NO: 46.

In certain embodiments, the isolated nucleic acid molecule encodes a functional portion of a presently disclosed CD56-targeted CAR. As used herein, the term "functional portion" refers to any portion, part or fragment of a presently disclosed CD56-targeted CAR, which portion, part or fragment retains the biological activity of the CD56-targeted CAR (the parent CAR). For example, functional portions encompass the portions, parts or fragments of a presently disclosed CD56-targeted CAR that retains the ability to recognize a target cell, to treat a disease, e.g., multiple myeloma, to a similar, same, or even a higher extent as the parent CAR. In certain embodiments, an isolated nucleic acid molecule encoding a functional portion of a presently disclosed CD56-targeted CAR can encode a protein comprising, e.g., about 10%, about 20%, about 25%, about 30%, about 35%, about 40%, about 45%, about 50%, about 55%, about 60%, about 65%, about 70%, about 75%, about 80%, about 85%, about 90%, and about 95%, or more of the parent CAR.

Cooper and his colleagues developed a CD56-targeted CAR that includes a murine scFv obtained from a known monoclonal antibody N901 (Crossland et al., Molecular Therapy, Abstract #198 (June 2013); 21 (Supplemental 1s). Using a mouse antibody or a mouse scFv for treating humans can lead to anti-mouse antibody (HAMA) response, which may be life-threatening. Unlike the CD56-targeted CAR developed by Cooper and his colleagues, in certain embodiments, the presently disclosed CD56-targeted CAR comprises a human scFv, and thus, affords a much decreased risk of immunogenicity, compared with CARs comprising murine antibodies (see Maus et al., *Cancer Immunol Res* (2003); 1(1):26-31), which reports that the potential immunogenicity of CARs derived from murine antibodies may be a safety issue for mRNA CARs).

IV. Immunoresponsive Cells

The presently disclosed subject matter provides immunoresponsive cells expressing a CAR that comprises an extracellular antigen-binding domain, a transmembrane domain and an intracellular domain, where the extracellular antigen-binding domain specifically binds to CD56 (e.g., human CD56) as described above. The immunoresponsive cells can be transduced with a presently disclosed CAR such that the cells express the CAR. The presently disclosed subject matter also provides methods of using such cells for the treatment of a tumor, e.g., multiple myeloma (MM). The immunoresponsive cells of the presently disclosed subject matter can be cells of the lymphoid lineage. The lymphoid lineage, comprising B, T and natural killer (NK) cells, provides for the production of antibodies, regulation of the cellular immune system, detection of foreign agents in the blood, detection of cells foreign to the host, and the like. Non-limiting examples of immunoresponsive cells of the lymphoid lineage include T cells, Natural Killer (NK) cells, embryonic stem cells, and pluripotent stem cells (e.g., those from which lymphoid cells may be differentiated). T cells can be lymphocytes that mature in the thymus and are chiefly responsible for cell-mediated immunity. T cells are involved in the adaptive immune system. The T cells of the presently disclosed subject matter can be any type of T cells, including, but not limited to, T helper cells, cytotoxic T cells, memory T cells (including central memory T cells, stem-cell-like memory T cells (or stem-like memory T cells), and two types of effector memory T cells: e.g., $T_{EM}$ cells and $T_{EMRA}$ cells, Regulatory T cells (also known as suppressor T cells), Natural killer T cells, Mucosal associated invariant T cells, and γδ T cells. Cytotoxic T cells (CTL or killer T cells) are a subset of T lymphocytes capable of inducing the death of infected somatic or tumor cells. In certain embodiments, the CAR-expressing T cells express Foxp3 to achieve and maintain a T regulatory phenotype.

Natural killer (NK) cells can be lymphocytes that are part of cell-mediated immunity and act during the innate immune response. NK cells do not require prior activation in order to perform their cytotoxic effect on target cells.

The immunoresponsive cells of the presently disclosed subject matter can express an extracellular antigen-binding domain (e.g., a human scFV, a Fab that is optionally cross-linked, or a F(ab)$_2$) that specifically binds to CD56 (e.g., human CD56), for the treatment of cancer, e.g., multiple myeloma. Such immunoresponsive cells can be administered to a subject (e.g., a human subject) in need thereof for the treatment of cancer, e.g., multiple myeloma. In certain embodiments, the immunoresponsive cell is a T cell. The T cell can be a CD4$^+$ T cell or a CD8$^+$ T cell. In certain embodiments, the T cell is a CD4+ T cell. In certain embodiments, the T cell is a CD8+ T cell.

A presently disclosed immunoresponsive cell can further include at least one recombinant or exogenous co-stimulatory ligand. For example, a presently disclosed immunoresponsive cell can be further transduced with at least one co-stimulatory igand, such that the immunoresponsive cell co-expresses or is induced to co-express the CD56-targeted CAR and the at least one co-stimulatory ligand. The interaction between the CD56-targeted CAR and at least one co-stimulatory ligand provides a non-antigen-specific signal important for full activation of an immunoresponsive cell (e.g., T cell). Co-stimulatory ligands include, but are not limited to, members of the tumor necrosis factor (TNF) superfamily, and immunoglobulin (Ig) superfamily ligands. TNF is a cytokine involved in systemic inflammation and stimulates the acute phase reaction. Its primary role is in the regulation of immune cells. Members of TNF superfamily share a number of common features. The majority of TNF superfamily members are synthesized as type II transmembrane proteins (extracellular C-terminus) containing a short cytoplasmic segment and a relatively long extracellular region. TNF superfamily members include, without limitation, nerve growth factor (NGF), CD40L (CD40L)/CD154, CD137L/4-1BBL, TNF-α, CD134L/OX40L/CD252, CD27L/CD70, Fas ligand (FasL), CD30L/CD153, tumor necrosis factor beta (TNFβ)/lymphotoxin-alpha (LTα), lymphotoxin-beta (LTβ), CD257/B cell-activating factor (BAFF)/Blys/THANK/Tall-1, glucocorticoid-induced TNF Receptor ligand (GITRL), and TNF-related apoptosis-inducing ligand (TRAIL), LIGHT (TNFSF14). The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, but are not limited to, CD80 and CD86, both ligands for CD28, PD-L1/(B7-H1) that ligands for PD-1. In certain embodiments, the at least one co-stimulatory ligand is selected from the group consisting of 4-1BBL, CD80, CD86, CD70, OX40L, CD48, TNFRSF14, PD-L1, and combinations thereof. In certain embodiments, the immunoresponsive cell comprises one recombinant co-stimulatory ligand that is 4-1BBL. In certain embodiments, the immunoresponsive cell comprises two recombinant co-stimulatory ligands that are 4-1BBL and CD80. CARs comprising at least one co-stimulatory ligand are described in U.S. Pat. No. 8,389,282, which is incorporated by reference in its entirety.

Furthermore, a presently disclosed immunoresponsive cell can further comprise at least one exogenous cytokine. For example, a presently disclosed immunoresponsive cell can be further transduced with at least one cytokine, such that the immunoresponsive cell secretes the at least one cytokine as well as expresses the CD56-targeted CAR. In certain embodiments, the at least one cytokine is selected from the group consisting of IL-2, IL-3, IL-6, IL-7, IL-11, IL-12, IL-15, IL-17, and IL-21. In certain embodiments, the cytokine is IL-12.

The CD56-specific or CD56-targeted human lymphocytes that can be used in peripheral donor lymphocytes, e.g., those disclosed in Sadelain, M., et al. 2003 *Nat Rev Cancer* 3:35-45 (disclosing peripheral donor lymphocytes genetically modified to express CARs), in Morgan, R. A., et al. 2006 *Science* 314:126-129 (disclosing peripheral donor lymphocytes genetically modified to express a full-length tumor antigen-recognizing T cell receptor complex comprising the α and β heterodimer), in Panelli, M. C., et al. 2000 *J Immunol* 164:495-504; Panelli, M. C., et al. 2000 *J Immunol* 164:4382-4392 (disclosing lymphocyte cultures derived from tumor infiltrating lymphocytes (TILs) in tumor biopsies), and in Dupont, J., et al. 2005 Cancer Res 65:5417-5427; Papanicolaou, G. A., et al. 2003 Blood 102:2498-2505 (disclosing selectively in vitro-expanded antigen-specific peripheral blood leukocytes employing artificial antigen-presenting cells (AAPCs) or pulsed dendritic cells). The immunoresponsive cells (e.g., T cells) can be autologous, non-autologous (e.g., allogeneic), or derived in vitro from engineered progenitor or stem cells.

In certain embodiments, a presently disclosed immunoresponsive cell (e.g., T cell) expresses from about 1 to about 5, from about 1 to about 4, from about 2 to about 5, from about 2 to about 4, from about 3 to about 5, from about 3 to about 4, from about 4 to about 5, from about 1 to about 2, from about 2 to about 3, from about 3 to about 4, or from about 4 to about 5 vector copy numbers/cell of a presently disclosed CD56-targeted CAR.

For example, the higher the CAR expression level in an immunoresponsive cell, the greater cytotoxicity and cytokine production the immunoresponsive cell exhibits. An immunoresponsive cell (e.g., T cell) having a high CD56-CAR expression level can induce antigen-specific cytokine production or secretion and/or exhibit cytotoxicity to a tissue or a cell having a low expression level of CD56, e.g., about 2,000 or less, about 1,000 or less, about 900 or less, about 800 or less, about 700 or less, about 600 or less, about 500 or less, about 400 or less, about 300 or less, about 200 or less, about 100 or less of CD56 binding sites/cell. Additionally or alternatively, the cytotoxicity and cytokine production of a presently disclosed immunoresponsive cell (e.g., T cell) are proportional to the expression level of human CD56 in a target tissue or a target cell. For example, the higher the expression level of human CD56 in the target, the greater cytotoxicity and cytokine production the immunoresponsive cell exhibits.

CD56 is strongly expressed by malignant plasma cells in over 70% patients with myeloma; however, CD56 is also expressed at lower levels on normal tissue types including neuronal cells, NK cells and a subset of activated T cells. In certain embodiments, an immunoresponsive cell (e.g., a T cell) comprising a presently disclosed CD56-targeted CAR can exhibit cytotoxicity, e.g., the ability to induce cell lysis, and antitumor activity against cells expressing high levels of CD56 (referred to as "high CD56-expressing cells"), e.g., cancerous cells. In certain embodiments, an immunoresponsive cell (e.g., a T cell) comprising a presently disclosed CD56-targeted CAR can exhibit little to no cytotoxicity against cells not expressing CD56 (referred to as "CD56-negative cells") and/or cells expressing low levels of CD56 (referred to as "low CD56-expressing cells"), e.g., neuronal cells, NK cells and a subset of activated T cells. In certain embodiments, an immunoresponsive cell of the present disclosure exhibits a cytotoxic effect against high CD56-expressing cells that is at least about 2-times, about 3-times, about 4-times, about 5-times, about 6-times, about 7-times, about 8-times, about 9-times or about 10-times the cytotoxic effect exhibited against CD56-negative cells or low CD56-expressing cells by the immunoresponsive cell. In certain embodiments, "high CD56-expressing cells" are cells with a mean fluorescence intensity (MFI) of greater than about $1\times10^4$, greater than about $1\times10^5$, greater than about $1\times10^6$, about $1\times10^4$ to about $1\times10^6$, about $1\times10^4$ to about $1\times10^5$, or about $1\times10^5$ to about $1\times10^6$ as measured by flow cytometry. In certain embodiments, "low CD56-expressing cells" are cells with an MFI of less than about $1\times10^4$, less than about $9\times10^3$, less than about $8\times10^3$, less than about $7\times10^3$, less than about $6\times10^3$, less than about $5\times10^3$, less than about $4\times10^3$, less than about $1\times10^3$, less than about $1\times10^2$, less than about 10, about $1\times10^2$ to about $1\times10^3$, or about 10 to about $1\times10^2$ as measured by flow cytometry.

Additionally, the immunoresponsive cells can comprise and express (is transduced to express) an antigen recognizing receptor that binds to a second antigen that is different than CD56 (e.g., human CD56). The inclusion of an antigen recognizing receptor in addition to a presently disclosed CAR on the immunoresponsive cell can increase the avidity of the CAR or the immunoresponsive cell comprising thereof on a targeted cell, especially, the CAR is one that has a low binding affinity to CD56 (e.g., human CD56), e.g., a $K_d$ of about $2\times10^{-8}$ M or more, about $5\times10^{-8}$ M or more, about $8\times10^{-8}$ M or more, about $9\times10^{-8}$ M or more, about $1\times10^{-7}$ M or more, about $2\times10^{-7}$ M or more, or about $5\times10^{-7}$ M or more.

Figure 3:
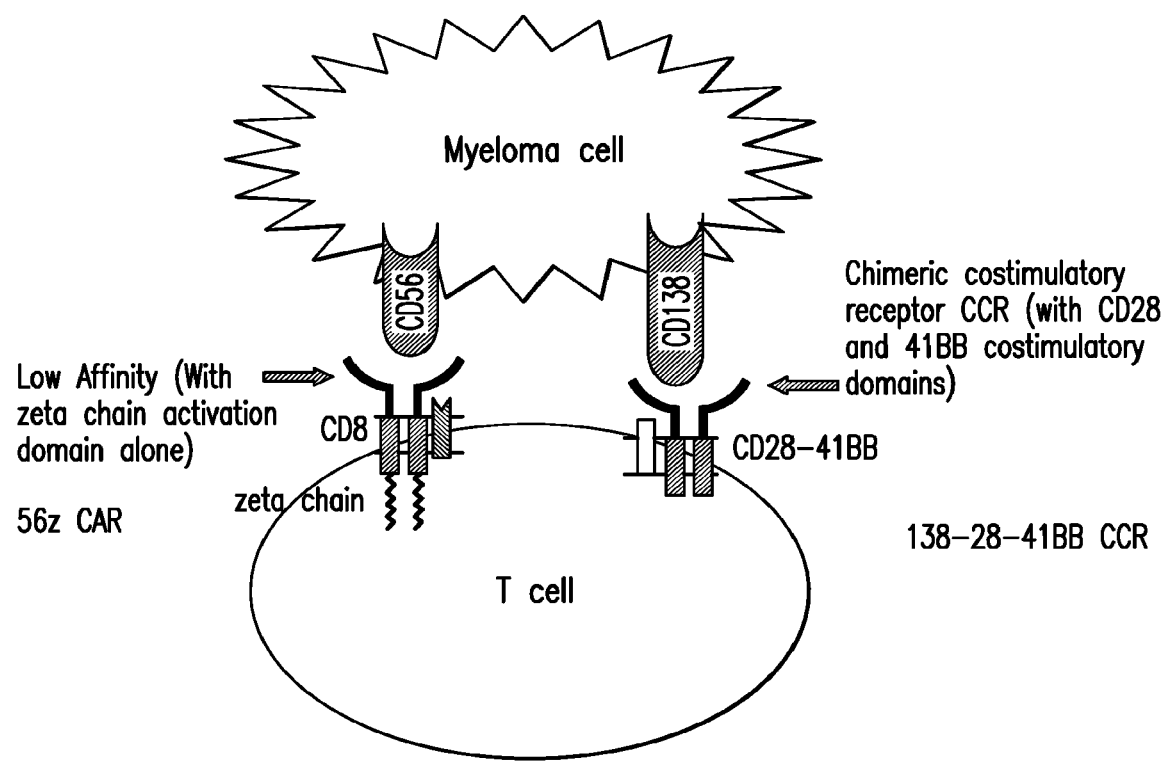
FIG. 3 depicts an immunoresponsive cell comprising a CD56-targeted CAR and a chimeric co-stimulatory receptor (CCR) targeting a second antigen in accordance with one non-limiting embodiment of the presently disclosed subject matter.

In certain embodiments, the antigen recognizing receptor is a chimeric co-stimulatory receptor (CCR). As used herein, the term "chimeric co-stimulatory receptor" or "CCR" refers to a chimeric receptor that binds to an antigen and provides co-stimulatory signals, but does not provide a T-cell activation signal. CCR is described in Krause, et al., J. Exp. Med. (1998); 188(4):619-626, and US20020018783, the contents of which are incorporated by reference in their entireties. CCRs mimic co-stimulatory signals, but unlike, CARs, do not provide a T-cell activation signal, e.g., CCRs lack a CD3ζ polypeptide. CCRs provide co-stimulation, e.g., a CD28-like signal, in the absence of the natural co-timulatory ligand on the antigen-presenting cell. A combinatorial antigen recognition, i.e., use of a CCR in combination with a CAR, can augment T-cell reactivity against the dual-antigen expressing T cells, thereby improving selective tumor targeting. Kloss et al., describe a strategy that integrates combinatorial antigen recognition, split signaling, and, critically, balanced strength of T-cell activation and costimulation to generate T cells that eliminate target cells that express a combination of antigens while sparing cells that express each antigen individually (Kloss et al., *Nature Biotechnololgy* (2013); 31(1):71-75, the content of which is incorporated by reference in its entirety). With this approach, T-cell activation requires CAR-mediated recognition of one antigen (e.g., CD56), whereas costimulation is independently mediated by a CCR specific for a second antigen. To achieve tumor selectivity, the combinatorial antigen recognition approach diminishes the efficiency of T-cell activation to a level where it is ineffective without rescue provided by simultaneous CCR recognition of the second antigen. In certain embodiments, the CCR comprises an extracellular antigen-binding domain that binds to an antigen different than CD56, a transmembrane domain, and a co-stimulatory signaling region that comprises at least one co-stimulatory molecule, including, but not limited to, CD28, 4-1BB, OX40, ICOS, PD-1, CTLA-4, LAG-3, 2B4, and BTLA. In certain embodiments, the co-stimulatory signaling region of the CCR comprises one co-stimulatory signaling molecule. In certain embodiments, the one co-stimulatory signaling molecule is CD28. In certain embodiments, the one co-stimulatory signaling molecule is 4-1BB. In certain embodiments, the co-stimulatory signaling region of the CCR comprises two co-stimulatory signaling molecules. In certain embodiments, the two co-stimulatory signaling molecules are CD28 and 4-1BB. A second antigen is selected so that expression of both CD56 and the second antigen is restricted to the targeted cells (e.g., cancerous tissue or cancerous cells). Similar to a CAR, the extracellular antigen-binding domain can be a scFv, a Fab, a F(ab)$_2$, or a fusion protein with a heterologous sequence to form the extracellular antigen-binding domain. In certain embodiments, the CCR comprises a scFv that binds to CD138, transmembrane domain comprising a CD28 polypeptide, and a co-stimulatory signaling region comprising two co-stimulatory signaling molecules that are CD28 and 4-1BB, as shown in FIG. 3. As shown in FIG. 3, a presently disclosed T cell comprises or is transduced to express a presently disclosed CAR targeting CD56 and a CCR targeting CD138.

Figure 4:
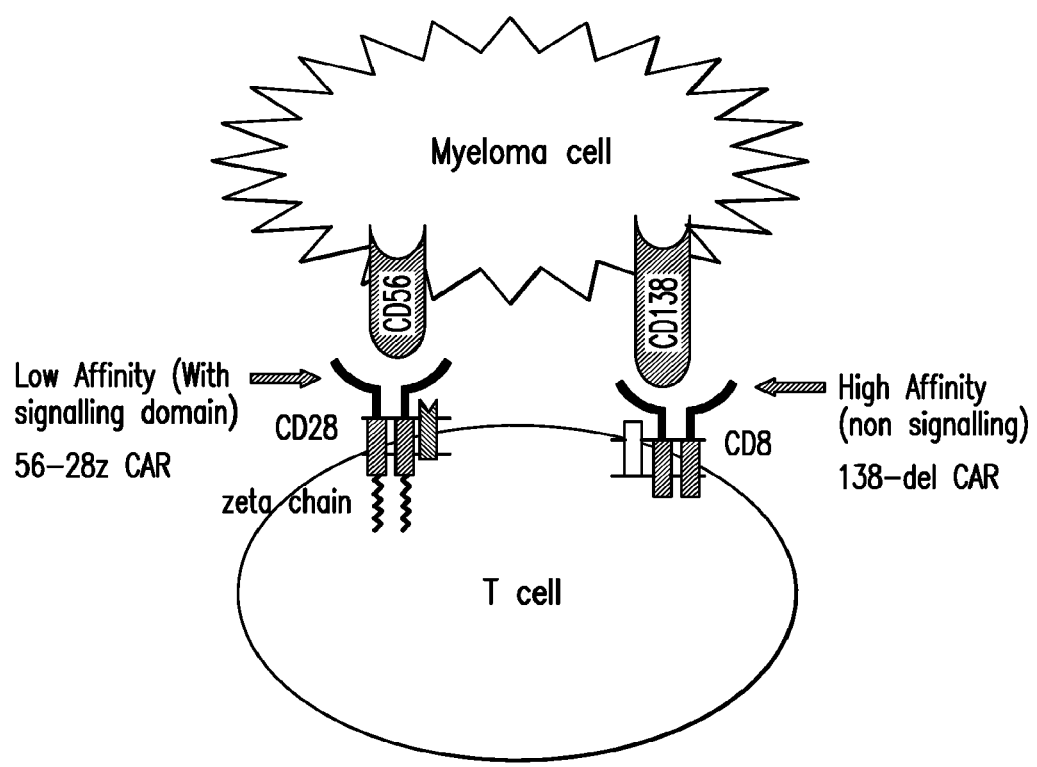
FIG. 4 depicts an immunoresponsive cell comprising a CD56-targeted CAR and a truncated CAR targeting a second antigen in accordance with one non-limiting embodiment of the presently disclosed subject matter.

In certain embodiments, the antigen recognizing receptor is a truncated CAR. A "truncated CAR" is different from a CAR by lacking an intracellular signaling domain. For example, a truncated CAR comprises an extracellular antigen-binding domain and a transmembrane domain, and lacks an intracellular signaling domain. In accordance with the presently disclosed subject matter, the truncated CAR has a high binding affinity to the second antigen expressed on the targeted cells, e.g., myeloma cells. The truncated CAR functions as an adhesion molecule that enhances the avidity of a presently disclosed CAR, especially, one that has a low binding affinity to CD56, thereby improving the efficacy of the presently disclosed CAR or immunoresponsive cell (e.g., T cell) comprising thereof. In certain embodiments, the truncated CAR comprises an extracellular antigen-binding domain that binds to CD138, a transmembrane domain comprising a CD8 polypeptide, as shown in FIG. 4. As shown in FIG. 4, a presently disclosed T cell comprises or is transduced to express a presently disclosed CAR targeting CD56 and a truncated CAR targeting CD138.

In certain embodiments, the targeted cells are myeloma cells. When the targeted cells are myeloma cells, the second antigen can be selected from the group consisting of CD138, CS-1, CD38, CD74, BCMA, Lewis-Y, NYESO-1, MAGE A3, and CT-7.

The unpurified source of CTLs may be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-CTLs initially. Monoclonal antibodies are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. Preferably, at least about 80%, usually at least 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography; cytotoxic agents joined to or used in conjunction with a mAb, including, but not limited to, complement and cytotoxins; and panning with antibody attached to a solid matrix, e.g. plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing dyes associated with dead cells such as propidium iodide (PI). Preferably, the cells are collected in a medium comprising 2% fetal calf serum (FCS) or 0.2% bovine serum albumin (BSA) or any other suitable, preferably sterile, isotonic medium.

V. Vectors

Genetic modification of immunoresponsive cells (e.g., T cells, NK cells) can be accomplished by transducing a substantially homogeneous cell composition with a recombinant DNA or RNA construct. The vector can be a retroviral vector (e.g., gamma retroviral), which is employed for the introduction of the DNA or RNA construct into the host cell genome. For example, a polynucleotide encoding the CD56-targeted CAR can be cloned into a retroviral vector and expression can be driven from its endogenous promoter, from the retroviral long terminal repeat, or from an alternative internal promoter.

Non-viral vectors or RNA may be used as well. Random chromosomal integration, or targeted integration (e.g., using a nuclease, transcription activator-like effector nucleases (TALENs), Zinc-finger nucleases (ZFNs), and/or clustered regularly interspaced short palindromic repeats (CRISPRs), or transgene expression (e.g., using a natural or chemically modified RNA) can be used.

For initial genetic modification of the cells to provide CD56-targeted CAR expressing cells, a retroviral vector is generally employed for transduction, however any other suitable viral vector or non-viral delivery system can be used. For subsequent genetic modification of the cells to provide cells comprising an antigen presenting complex comprising at least two co-stimulatory ligands, retroviral gene transfer (transduction) likewise proves effective. Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986) *Mol. Cell. Biol.* 6:2895-2902); and CRIP (Danos, et al. (1988) *Proc. Natl. Acad. Sci. USA* 85:6460-6464). Non-amphotropic particles are suitable too, e.g., particles pseudotyped with VSVG, RD114 or GALV envelope and any other known in the art.

Possible methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J. Clin. Invest.* 89:1817.

Transducing viral vectors can be used to express a co-stimulatory ligand and/or secrets a cytokine (e.g., 4-1BBL and/or IL-12) in an immunoresponsive cell. Preferably, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263 267, 1996; and Miyoshi et al., Proc. Natl. Acad. Sci. U.S.A. 94:10319, 1997). Other viral vectors that can be used include, for example, adenoviral, lentiviral, and adeno-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

In certain non-limiting embodiments, the vector expressing a presently disclosed CD56-targeted CAR is a retroviral vector, e.g., an oncoretroviral vector.

Non-viral approaches can also be employed for the expression of a protein in cell. For example, a nucleic acid molecule can be introduced into a cell by administering the nucleic acid in the presence of lipofection (Feigner et al., Proc. Nat'l. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g., Zinc finger nucleases, meganucleases, or TALE nucleases). Transient expression may be obtained by RNA electroporation.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g., the elongation factor 1α enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

VI. Polypeptides and Analogs and Polynucleotides

Also included in the presently disclosed subject matter are extracellular antigen-binding domains that specifically binds to a CD56 (e.g., human CD56) (e.g., an scFv (e.g., a human scFv), a Fab, or a $(Fab)_2$), CD3ζ, CD8, CD28, etc. polypeptides or fragments thereof, and polynucleotides encoding thereof that are modified in ways that enhance their anti-tumor activity when expressed in an immunoresponsive cell. The presently disclosed subject matter provides methods for optimizing an amino acid sequence or a nucleic acid sequence by producing an alteration in the sequence. Such alterations may comprise certain mutations, deletions, insertions, or post-translational modifications. The presently disclosed subject matter further comprises analogs of any naturally-occurring polypeptide of the presently disclosed subject matter. Analogs can differ from a naturally-occurring polypeptide of the presently disclosed subject matter by amino acid sequence differences, by post-translational modifications, or by both. Analogs of the presently disclosed subject matter can generally exhibit at least about 85%, about 90%, about 91%, about 92%, about 93%, about 94%, about 95%, about 96%, about 97%, about 98%, about 99% or more identity or homology with all or part of a naturally-occurring amino, acid sequence of the presently disclosed subject matter. The length of sequence comparison is at least about 5, about 10, about 15, about 20, about 25, about 50, about 75, about 100 or more amino acid residues. Again, in an exemplary approach to determining the degree of identity, a BLAST program may be used, with a probability score between $e^{-3}$ and $e^{-100}$ indicating a closely related sequence. Modifications comprise in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the presently disclosed subject matter by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amina acids, e.g., D-amino acids or non-naturally occurring or synthetic amino acids, e.g., beta (β) or gamma (γ) amino acids.

In addition to full-length polypeptides, the presently disclosed subject matter also provides fragments of any one of the polypeptides or peptide domains of the presently disclosed subject matter. A fragment can be at least about 5, about 10, about 13, or about 15 amino acids. In some embodiments, a fragment is at least about 20 contiguous amino acids, at least about 30 contiguous amino acids, or at least about 50 contiguous amino acids. In some embodiments, a fragment is at least about 60 to about 80, about 100, about 200, about 300 or more contiguous amino acids. Fragments of the presently disclosed subject matter can be generated by methods known to those of ordinary skill in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein of the invention. Such analogs are administered according to methods of the presently disclosed subject matter. Such analogs may exceed the physiological activity of the original polypeptide. Methods of analog design are well known in the art, and synthesis of analogs can be carried out according to such methods by modifying the chemical structures such that the resultant analogs increase the anti-neoplastic activity of the original polypeptide when expressed in an immunoresponsive cell. These chemical modifications include, but are not limited to, substituting alternative R groups and varying the degree of saturation at specific carbon atoms of a reference polypeptide. The protein analogs can be relatively resistant to in vivo degradation, resulting in a more prolonged therapeutic effect upon administration. Assays for measuring functional activity include, but are not limited to, those described in the Examples below.

In accordance with the presently disclosed subject matter, the polynucleotides encoding an extracellular antigen-binding domain that specifically binds to CD56 (e.g., human CD56) (e.g., an scFv (e.g., a human scFv), a Fab, or a $(Fab)_2$), CD3ζ, CD8, CD28) can be modified by codon optimization. Codon optimization can alter both naturally occurring and recombinant gene sequences to achieve the highest possible levels of productivity in any given expression system. Factors that are involved in different stages of protein expression include codon adaptability, mRNA structure, and various cis-elements in transcription and translation. Any suitable codon optimization methods or technologies that are known to ones skilled in the art can be used to modify the polynucleotides of the presently disclosed subject matter, including, but not limited to, OptimumGene™, Encor optimization, and Blue Heron.

VII. Antibodies

The present disclosure further provides antibodies or antigen-binding portions thereof that bind to a CD56 polypeptide.

In certain embodiments, an antibody, or antigen-binding portion thereof, comprises (a) a $V_H$ comprising an amino acid sequence selected from the group consisting of SEQ ID NO: 7, SEQ ID NO: 19, SEQ ID NO: 21, SEQ ID NO: 23 and SEQ ID NO: 25; and/or (b) a $V_L$ comprising an amino acid sequence selected from the group consisting of SEQ ID NO: 8, SEQ ID NO: 20, SEQ ID NO: 22, SEQ ID NO: 24 and SEQ ID NO: 26.

In certain embodiments, an antibody, or antigen-binding portion thereof, comprises: (a) a heavy chain variable region comprising an amino acid sequence set forth in SEQ ID NO: 7, and a light chain variable region that comprising an amino acid sequence set forth in SEQ ID NO: 8; (b) a heavy chain variable region comprising an amino acid sequence set forth in SEQ ID NO: 19, and a light chain variable region that comprising an amino acid sequence set forth in SEQ ID NO: 20; (c) a heavy chain variable region comprising an amino acid sequence set forth in SEQ ID NO: 21, and a light chain variable region that comprising an amino acid sequence set forth in SEQ ID NO: 22; (d) a heavy chain variable region comprising an amino acid sequence set forth in SEQ ID NO: 23, and a light chain variable region that comprising an amino acid sequence set forth in SEQ ID NO: 24; or (e) a heavy chain variable region comprising an amino acid sequence set forth in SEQ ID NO: 25, and a light chain variable region that comprising an amino acid sequence set forth in SEQ ID NO: 26.

In certain embodiments, a presently disclosed antibody, or antigen-binding portion thereof, comprises: (a) a heavy chain variable region CDR1 comprising an amino acid sequence selected from the group consisting of SEQ ID NO: 1 and SEQ ID NO: 9; (b) a heavy chain variable region CDR2 comprising an amino acid sequence selected from the group consisting of SEQ ID NO: 2 and SEQ ID NO: 10; (c) a heavy chain variable region CDR3 comprising an amino acid sequence selected from the group consisting of SEQ ID NO: 3, SEQ ID NO: 11 and SEQ ID NO: 59; (d) a light chain variable region CDR1 comprising an amino acid sequence selected from the group consisting of SEQ ID NO: 4, SEQ ID NO: 12 and SEQ ID NO: 13; (e) a light chain variable region CDR2 comprising an amino acid sequence selected from the group consisting of SEQ ID NO: 5 and SEQ ID NO: 14; and (f) a light chain variable region CDR3 comprising an amino acid sequence selected from the group consisting of SEQ ID NO: 6, SEQ ID NO: 15, SEQ ID NO: 16, SEQ ID NO: 17 and SEQ ID NO: 18.

In certain embodiments, a presently disclosed antibody, or antigen-binding portion thereof, comprises: a heavy chain variable region CDR1 comprising an amino acid sequence set forth in SEQ ID NO: 1; a heavy chain variable region CDR2 comprising an amino acid sequence set forth in SEQ ID NO: 2; a heavy chain variable region CDR3 comprising an amino acid sequence set forth in SEQ ID NO: 3 or SEQ ID NO: 59; a light chain variable region CDR1 comprising an amino acid sequence set forth in SEQ ID NO: 4; a light chain variable region CDR2 comprising an amino acid sequence set forth in SEQ ID NO: 5; and a light chain variable region CDR3 comprising an amino acid sequence set forth in SEQ ID NO: 6.

In certain embodiments, a presently disclosed antibody, or antigen-binding portion thereof, comprises: a heavy chain variable region CDR1 comprising an amino acid sequence set forth in SEQ ID NO: 9; a heavy chain variable region CDR2 comprising an amino acid sequence set forth in SEQ ID NO: 10; a heavy chain variable region CDR3 comprising an amino acid sequence set forth in SEQ ID NO: 11; a light chain variable region CDR1 comprising an amino acid sequence set forth in SEQ ID NO: 12; a light chain variable region CDR2 comprising an amino acid sequence set forth in SEQ ID NO: 14; and a light chain variable region CDR3 comprising an amino acid sequence set forth in SEQ ID NO: 15.

In certain embodiments, a presently disclosed antibody, or antigen-binding portion thereof, comprises: a heavy chain variable region CDR1 comprising an amino acid sequence set forth in SEQ ID NO: 9; a heavy chain variable region CDR2 comprising an amino acid sequence set forth in SEQ ID NO: 10; a heavy chain variable region CDR3 comprising an amino acid sequence set forth in SEQ ID NO: 11; a light chain variable region CDR1 comprising an amino acid sequence set forth in SEQ ID NO: 12; a light chain variable region CDR2 comprising an amino acid sequence set forth in SEQ ID NO: 14; and a light chain variable region CDR3 comprising an amino acid sequence set forth in SEQ ID NO: 16.

In certain embodiments, a presently disclosed antibody, or antigen-binding portion thereof, comprises: a heavy chain variable region CDR1 comprising an amino acid sequence set forth in SEQ ID NO: 9; a heavy chain variable region CDR2 comprising an amino acid sequence set forth in SEQ ID NO: 10; a heavy chain variable region CDR3 comprising an amino acid sequence set forth in SEQ ID NO: 11; a light chain variable region CDR1 comprising an amino acid sequence set forth in SEQ ID NO: 12; a light chain variable region CDR2 comprising an amino acid sequence set forth in SEQ ID NO: 14; and a light chain variable region CDR3 comprising an amino acid sequence set forth in SEQ ID NO: 17.

In certain embodiments, a presently disclosed antibody, or antigen-binding portion thereof, comprises: a heavy chain variable region CDR1 comprising an amino acid sequence set forth in SEQ ID NO: 9; a heavy chain variable region CDR2 comprising an amino acid sequence set forth in SEQ ID NO: 10; a heavy chain variable region CDR3 comprising an amino acid sequence set forth in SEQ ID NO: 11; a light chain variable region CDR1 comprising an amino acid sequence set forth in SEQ ID NO: 13; a light chain variable region CDR2 comprising an amino acid sequence set forth in SEQ ID NO: 14; and a light chain variable region CDR3 comprising an amino acid sequence set forth in SEQ ID NO: 18.

In certain embodiments, a presently disclosed antibody, or antigen-binding portion thereof, comprises: (i) a heavy chain variable region CDR3 comprising an amino acid sequence selected from the group consisting of SEQ ID NO: 3, SEQ ID NO: 11 and SEQ ID NO: 59 and/or (ii) a light chain variable region CDR3 comprising an amino acid sequence selected from the group consisting of SEQ ID NO: 6, SEQ ID NO: 15, SEQ ID NO: 16, SEQ ID NO: 17 and SEQ ID NO: 18.

The constant region/framework region of the presently disclosed antibodies can be altered, for example, by amino acid substitution, to modify the properties of the antibody (e.g., to increase or decrease one or more of: antigen binding affinity, Fc receptor binding, antibody carbohydrate, for example, glycosylation, fucosylation, etc., the number of cysteine residues, effector cell function, effector cell function, complement function or introduction of a conjugation site).

In certain embodiments, a presently disclosed antibody is a fully-human antibody. Fully-human antibodies are preferred for therapeutic use in humans because murine antibodies cause an immunogenicity reaction, known as the HAMA (human anti-mouse antibodies) response (Azinovic I, et al. Survival benefit associated with human anti-mouse antibody (HAMA) in patients with B-cell malignancies. Cancer Immunol. Immunother. 2006; 55(12):1451-8; Tjandra J J, et al. Development of human anti-murine antibody (HAMA) response in patients. Immunol Cell Biol 1990; 68(6):367-76), when administered to humans, causing serious side effects, including anaphylaxis and hypersensitivity reactions. This immunogenicity reaction is triggered by the human immune system recognizing the murine antibodies as foreign because of slightly different amino acid sequences from natural human antibodies. Humanization methods known in the art (Riechmann L, et al. Reshaping human antibodies for therapy. Nature 1988; 332 (6162): 332:323; Queen C, et al. A humanized antibody that binds to the interleukin 2 receptor. Proc Natl Acad Sci USA 1989; 86 (24): 10029-33) can be employed to reduce the immunogenicity of murine-derived antibodies (Gerd R, et al. Serological Analysis of Human Anti-Human Antibody Responses in Colon Cancer Patients Treated with Repeated Doses of Humanized Monoclonal Antibody A33. Cancer Res 2001; 61:6851-6859).

The use of phage display libraries has made it possible to select large numbers of antibody repertoires for unique and rare antibodies against very defined epitopes (for more details on phage display see McCafferty, et al., Phage antibodies: filamentous phage displaying antibody variable domains. Nature, 348:552-554). The rapid identification of human Fab or scFvs highly specific for tumor antigen-derived peptide-MHC complex molecules has thus become possible. Immuno-toxins, generated by fusing TCR-like Fab specific for melanoma Ag MART-1 26-35/A2 or gp100 280-288/A2 to a truncated form of Pseudomonas endotoxin, have been shown to inhibit human melanoma growth both in vitro and in vivo (Klechevsky E, et al. Antitumor activity of immunotoxins with T-cell receptor-like specificity against human melanoma xenografts. Cancer Res 2008; 68 (15): 6360-6367). In addition, by engineering full-length monoclonal antibodies (mAbs) using the Fab fragments, it is possible to directly generate a therapeutic human mAbs, bypassing months of time-consuming work, normally needed for developing therapeutic mAbs, e.g., for treating cancers.

Homologous Antibodies

In certain embodiments, an antibody of the presently disclosed subject matter comprises heavy and light chain variable regions comprising amino acid sequences that are homologous to the amino acid sequences of the antibodies or antigen-binding portions thereof described herein (see Tables 1-5), and wherein the antibodies, or antigen-binding portions thereof, retain the desired functional properties of the anti-CD56 antibodies, or antigen-binding portions thereof, of the presently disclosed subject matter.

For example, and not by way of limitation, a presently disclosed antibody, or antigen-binding portion thereof, comprises: (a) a heavy chain variable region comprising an amino acid sequence that is at least about 80% homologous to an amino acid sequence selected from the group consisting of SEQ ID NO: 7, SEQ ID NO: 19, SEQ ID NO: 21, SEQ ID NO: 23 and SEQ ID NO: 25; and/or (b) a light chain variable region comprising an amino acid sequence that is at least about 80% homologous to an amino acid sequence selected from the group consisting of SEQ ID NO: 8, SEQ ID NO: 20, SEQ ID NO: 22, SEQ ID NO: 24 and SEQ ID NO: 26; and wherein the antibody, or antigen-binding portion thereof, binds to a CD56 polypeptide.

In certain embodiments, the $V_H$ and/or $V_L$ amino acid sequences can be about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% homologous to the sequences set forth above. An antibody comprising $V_H$ and/or $V_L$ regions having high (i.e., 80% or greater) homology to the $V_H$ and $V_L$ regions of the sequences set forth above, can be obtained by mutagenesis (e.g., site-directed or PCR-mediated mutagenesis), followed by testing of the encoded altered antibody for retained function (i.e., the binding affinity) using the binding assays described herein.

In certain embodiments, a presently disclosed antibody, or antigen-binding portion thereof, comprises: (a) a heavy chain variable region CDR1 comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% homologous to an amino acid sequence selected from the group consisting of SEQ ID NO: 1 and SEQ ID NO: 9; (b) a heavy chain variable region CDR2 comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% homologous to an amino acid sequence selected from the group consisting of SEQ ID NO: 2 and SEQ ID NO: 10; (c) a heavy chain variable region CDR3 comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% homologous to an amino acid sequence selected from the group consisting of SEQ ID NO: 3, SEQ ID NO: 11 and SEQ ID NO: 59; (d) a light chain variable region CDR1 comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% homologous to an amino acid sequence selected from the group consisting of SEQ ID NO: 4, SEQ ID NO: 12 and SEQ ID NO: 13; (e) a light chain variable region CDR2 comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% homologous to an amino acid sequence selected from the group consisting of SEQ ID NO: 5 and SEQ ID NO: 14; and/or (f) a light chain variable region CDR3 comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% homologous to an amino acid sequence selected from the group consisting of SEQ ID NO: 6, SEQ ID NO: 15, SEQ ID NO: 16, SEQ ID NO: 17 and SEQ ID NO: 18.

In certain embodiments, a presently disclosed antibody, or antigen-binding portion thereof, comprises: (i) a heavy chain variable region CDR3 comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% homologous to an amino acid sequence selected from the group consisting of SEQ ID NO: 3, SEQ ID NO: 11 and SEQ ID NO: 59; and/or (ii) a light chain variable region CDR3 comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% homologous to an amino acid sequence selected from the group consisting of SEQ ID NO: 6, SEQ ID NO: 15, SEQ ID NO: 16, SEQ ID NO: 17 and SEQ ID NO: 18.

As used herein, the percent homology between two amino acid sequences can be equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below. In certain embodiments, the percent homology between two amino acid sequences can be determined as described above.

Antibodies with Modifications

In certain embodiments, a presently disclosed antibody (or antigen-binding portion thereof) comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the antibodies (or antigen-binding portions thereof) described herein (see Tables 1-5), or modifications thereof, and wherein the antibodies (or antigen-binding portions thereof) retain the desired functional properties of the anti-CD56 antibodies (or antigen-binding portions thereof) of the presently disclosed subject matter.

In certain embodiments, such modifications do not significantly affect or alter the binding characteristics of the antibody containing the amino acid sequence. Non-limiting examples of such modifications include amino acid substitutions, additions and deletions. Modifications can be introduced into the presently antibody or antigen-binding portion thereof by standard techniques known in the art, such as site-directed mutagenesis and PCR-mediated mutagenesis.

The modifications can be conservative modifications, non-conservative modifications, or mixtures of conservative and non-conservative modifications. As discussed above, conservative amino acid substitutions are ones in which the amino acid residue is replaced with an amino acid residue having a similar side chain. Families of amino acid residues having similar side chains have been defined in the art. Exemplary conservative amino acid substitutions are shown in Table 6. In certain embodiments, amino acid substitutions may be introduced into an antibody of interest and the products screened for a desired activity, e.g., retained/improved antigen binding, decreased immunogenicity, or improved ADCC or CDC.

TABLE 6

| Original Residue | Exemplary conservative amino acid Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe |
| Leu (L) | Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala |

Amino acids may be grouped according to common side-chain properties:
hydrophobic: Norleucine, Met, Ala, Val, Leu, Ile;
neutral hydrophilic: Cys, Ser, Thr, Asn, Gln;
acidic: Asp, Glu;
basic: His, Lys, Arg;
residues that influence chain orientation: Gly, Pro;
aromatic: Trp, Tyr, Phe.

In certain embodiments, one or more amino acid residues within a CDR region can be replaced with other amino acid residues from the same group and the altered antibody can be tested for retained function using the functional assays described herein.

Non-conservative substitutions entail exchanging a member of one of these classes for another class.

In certain embodiments, no more than one, no more than two, no more than three, no more than four, no more than five residues within a specified sequence or a CDR region are altered.

Cross-competing Antibodies

The presently disclosed subject matter provides antibodies, or antigen-binding portions thereof, that cross-compete for binding to a CD56 polypeptide with any of the anti-CD56 antibodies or antigen-binding portions thereof of the presently disclosed subject matter.

The cross-competing antibodies or antigen-binding portions thereof bind to the same epitope region, e.g., same epitope, adjacent epitope, or overlapping as any of the anti-CD56 antibodies, or antigen-binding portions thereof, described herein.

Such cross-competing antibodies can be identified based on their ability to cross-compete with any one of the presently disclosed anti-CD56 antibodies or antigen-binding portions thereof in standard CD56 binding assays. For example, Biacore analysis, ELISA assays or flow cytometry can be used to demonstrate cross-competition with the antibodies or antigen-binding portions thereof of the presently disclosed subject matter. The ability of a test antibody to inhibit the binding of, for example, any one of the presently disclosed anti-CD56 antibodies or antigen-binding portions thereof to a CD56 polypeptide demonstrates that the test antibody can compete with any one of the presently disclosed anti-CD56 antibodies or antigen-binding portions thereof for binding to such CD56 polypeptides.

Characterization of Antibody Binding to Antigen

Antibodies of the presently disclosed subject can be tested for binding to a CD56 polypeptide by, for example, standard ELISA. To determine the isotype of purified antibodies, isotype ELISAs can be performed using reagents specific for antibodies of a particular isotype. Anti-CD56 human IgGs can be further tested for reactivity with the CD56 polypeptide by Western blotting.

In certain embodiments, $K_d$ is measured by a radiolabeled antigen binding assay (RIA). In certain embodiments, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)).

In certain embodiments, $K_d$ is measured using a BIA-CORE® surface plasmon resonance assay. For example, an assay using a BIACORE®-2000 or a BIACORE®-3000 (BlAcore, Inc., Piscataway, N.J.).

In certain embodiments, an anti-CD56 antibody, or antigen-binding portion thereof, of the present disclosure can have a $K_d$ from about 0.001 nM to about 1 µM or from about $10^8$ M to about $10^{-13}$ M. For example, and not by way of limitation, the anti-CD56 antibody can have a $K_d \leq 1$ µM, $\leq 100$ nM, $\leq 10$ nM, $\leq 1$ nM, $\leq 0.1$ nM, $\leq 0.01$ nM or $\leq 0.001$ nM. In certain embodiments, the anti-CD56 antibody, or antigen-binding portion thereof, can have a $K_d$ of about $2 \times 10^{-7}$ M or less. In certain embodiments, the $K_d$ is about $2 \times 10^{-7}$ M or less, about $1 \times 10^{-7}$ M or less, about $9 \times 10^{-8}$ M or less, about $1 \times 10^{-8}$ M or less, about $9 \times 10^{-9}$ or less, about $5 \times 10^{-9}$ or less, about $4 \times 10^{-9}$ or less, about $3 \times 10^{-9}$ or less, about $2 \times 10^{-9}$ or less, or about $1 \times 10^{-9}$ M or less. In certain non-limiting embodiments, the $K_d$ is from about $3 \times 10^{-9}$ M or less. In certain non-limiting embodiments, the $K_d$ is from about $3 \times 10^{-9}$ to about $2 \times 10^{-7}$.

Immunoconjugates

The presently disclosed subject provides for an anti-CD56 antibody or an antigen-binding portion thereof conjugated to a therapeutic moiety, such as a cytotoxin, a drug (e.g., an immunosuppressant) or a radiotoxin. Such conjugates are referred to herein as "immunoconjugates." Immunoconjugates that include one or more cytotoxins are referred to as "immunotoxins." A cytotoxin or cytotoxic agent includes any agent that is detrimental to (e.g., kills) cells. Non-limiting examples include taxol (such as ricin, diphtheria, gelonin), cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, calecheamicin, aureastatin, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other non-limiting examples of therapeutic cytotoxins that can be conjugated to an anti-CD56 antibody or an antigen-binding portion thereof disclosed herein include duocarmycins, calicheamicins, maytansines and auristatins, and derivatives thereof. A non-limiting example of a calicheamicin antibody conjugate is commercially available (Mylotarg™; Wyeth-Ayerst).

Cytoxins can be conjugated to anti-CD56 antibody or an antigen-binding portion thereof disclosed herein using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Anti-CD56 antibodies or antigen-binding portions thereof of the presently disclosed subject matter also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, $^{90}$Y, $^{131}$I, $^{225}$Ac, $^{213}$Bi, $^{223}$Ra, $^{177}$Lu, and $^{227}$Th. Method for preparing radioimmunconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention.

The antibody conjugates of the presently disclosed subject matter can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor (TNF) or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

The presently disclosed subject matter further provides for bispecific molecules comprising an anti-CD56 antibody or an antigen-binding portion thereof disclosed herein. An antibody or an antigen-binding portion thereof of the presently disclosed subject matter, can be derivatized or linked to another functional molecule, e.g., another peptide or protein (e.g., another antibody or ligand for a receptor) to generate a bispecific molecule that binds to at least two different binding sites or target molecules. The antibody of the presently disclosed subject matter can in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule, a presently disclosed anti-CD56 antibody or an antigen-binding portion thereof can be functionally linked (e.g., by chemical coupling, genetic fusion, noncovalent association or otherwise) to one or more other binding molecules, such as another antibody, antibody fragment, peptide or binding mimetic, such that a bispecific molecule results.

The presently disclosed subject matter provides bispecific molecules comprising at least one first binding specificity for a first target epitope or antigen and a second binding specificity for a second target epitope or antigen. The second target epitope or antigen can be different from the first epitope or antigen. In certain embodiments, the bispecific molecule is multispecific, the molecule can further include a third binding specificity. Where a first portion of a bispecific antibody binds to an antigen on a tumor cell for example and a second portion of a bispecific antibody recognizes an antigen on the surface of a human immune effector cell, the antibody is capable of recruiting the activity of that effector cell by specifically binding to the effector antigen on the human immune effector cell. In certain embodiments, bispecific antibodies, therefore, are able to form a link between effector cells, for example, T cells and tumor cells, thereby enhancing effector function.

The bispecific molecules of the presently disclosed subject matter can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Non-limiting examples of cross-linking agents include protein A, carbodiimide, N-succinimidyl-S-acetyl-thioacetate (SATA), 5, 5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160:1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In certain embodiments, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand×Fab fusion protein.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Other formats of bispecific antibodies can be constructed, such tandem scFv molecules (taFv), diabodies (Db), or single chain diabodies (scDb), and fusion protein with human serum albumin (Ryutaro, et al., *J Biol Chem* 2011; 286: 1812-1818; Anja, et al., *Blood* 2000; 95(6): 2098-2103; Weiner, et al., *J. Immunology* 1994; 152(5): 2385-2392; Dafne, et al., *J Biol Chem* 2007; 282: 12650-12660), but are devoid of Fc effector functions with distinct pharmacokinetic profiles.

Engineered and Modified Antibodies

An antibody of the presently disclosed subject matter can be prepared using an antibody or an antigen-binding portion thereof having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain CDRs. For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585, 089; 5,693,762 and 6,180,370 to Queen et al.)

Framework sequences can be obtained from public DNA databases or published references that include germline antibody gene sequences. For example, germline DNA sequences for human heavy and light chain variable region genes can be found in the "VBase" human germline sequence database (available on the Internet at world wide web.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline VH Sequences Reveals about Fifty Groups of VH Segments with Different Hypervariable Loops" J. Mol. Biol. 227:776-798; and Cox, J. P. L. et al. (1994) "A Directory of Human Germ-line VH Segments Reveals a Strong Bias in their Usage" Eur. J. Immunol. 24:827-836; the contents of each of which are expressly incorporated herein by reference. As another example, the germline DNA sequences for human heavy and light chain variable region genes can be found in the GenBank database.

The $V_H$ CDR1, CDR2, and CDR3 sequences, and the $V_L$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays. Preferably conservative modifications (as discussed above) are introduced. The mutations may be amino acid substitutions, additions or deletions. For example, no more than one, two, three, four or five residues within a CDR region are altered.

Accordingly, the presently disclosed subject matter provides for isolated anti-CD56 monoclonal antibodies or antigen-binding portions thereof comprising a heavy chain variable region comprising: (a) the $V_H$ CDR1 sequence of the antibodies and antigen-binding portions thereof disclosed herein, or an amino acid sequence having at least one (e.g., no more than one, no more than two, no more than three, no more than four or no more than five) amino acid modification (e.g., substitution, deletion and/or addition) as compared to the $V_H$ CDR1 sequence of any one of the antibodies or antigen-binding portions thereof disclosed herein; (b) the $V_H$ CDR2 sequence of any one of the antibodies or antigen-binding portions thereof disclosed herein, or an amino acid sequence having at least one (e.g., no more than one, no more than two, no more than three, no more than four or no more than five) amino acid modification (e.g., substitution, deletion and/or addition) as compared to the $V_H$ CDR2 of any one of the antibodies or antigen-binding portions thereof disclosed herein; (c) the $V_H$ CDR3 sequence of any one of the antibodies or antigen-binding portions thereof disclosed herein, or an amino acid sequence having at least one (e.g., no more than one, no more than two, no more than three, no more than four or no more than five) amino acid modification (e.g., substitution, deletion and/or addition) as compared to the $V_H$ CDR3 of any one of the antibodies or antigen-binding portions thereof disclosed herein; (d) the $V_L$ CDR1 sequence of any one of the antibodies or antigen-binding portions thereof disclosed herein, or an amino acid sequence having at least one (e.g., no more than one, no more than two, no more than three, no more than four or no more than five) amino acid modification (e.g., substitution, deletion and/or addition) as compared to the $V_L$ CDR1 of any one of the antibodies or antigen-binding portions thereof disclosed herein; (e) the $V_L$ CDR2 sequence of any one of the antibodies or antigen-binding portions thereof disclosed herein, or an amino acid sequence having at least one (e.g., no more than one, no more than two, no more than three, no more than four or no more than five) amino acid modification (e.g., substitution, deletion and/or addition) as compared to the $V_L$ CDR2 of any one of the antibodies or antigen-binding portions thereof disclosed herein; and/or (f) the $V_L$ CDR3 sequence of any one of the antibodies or antigen-binding portions thereof disclosed herein, or an amino acid sequence having at least one (e.g., no more than one, no more than two, no more than three, no more than four or no more than five) amino acid modification (e.g., substitution, deletion and/or addition) as compared to the $V_L$ CDR3 of any one of the antibodies or antigen-binding portions thereof disclosed herein.

For example, and not by way of limitation, the presently disclosed subject matter provides for isolated anti-CD56 monoclonal antibodies or antigen-binding portions thereof comprising: (a) a $V_H$ CDR1 region comprising the amino acid sequence set forth in SEQ ID NO: 1 or SEQ ID NO: 9, or an amino acid sequence having at least one (e.g., no more than one, no more than two, no more than three, no more than four or no more than five) amino acid modification (e.g., substitution, deletion and/or addition) as compared to SEQ ID NO: 1 or SEQ ID NO: 9; (b) a $V_H$ CDR2 region comprising the amino acid sequence set forth in SEQ ID NO: 2 or SEQ ID NO: 10, or an amino acid sequence having at least one (e.g., no more than one, no more than two, no more than three, no more than four or no more than five) amino acid modification (e.g., substitution, deletion and/or addition) as compared to SEQ ID NO: 2 or SEQ ID NO: 10; (c) a $V_H$ CDR3 region comprising the amino acid sequence set forth in SEQ ID NO: 3, SEQ ID NO: 11 or SEQ ID NO: 59, or an amino acid sequence having at least one (e.g., no more than one, no more than two, no more than three, no more than four or no more than five) amino acid modification (e.g., substitution, deletion and/or addition) as compared to SEQ ID NO: 3, SEQ ID NO: 11 or SEQ ID NO: 59; (d) a $V_L$ CDR1 region comprising the amino acid sequence set forth in SEQ ID NO: 4, SEQ ID NO: 12 or SEQ ID NO: 13, or an amino acid sequence having at least one (e.g., no more than one, no more than two, no more than three, no more than four or no more than five) amino acid modification (e.g., substitution, deletion and/or addition) as compared to SEQ ID NO: 4, SEQ ID NO: 12 or SEQ ID NO: 13; (e) a $V_L$ CDR2 region comprising the amino acid sequence set forth in SEQ ID NO: 5 or SEQ ID NO: 14, or an amino acid sequence having at least one (e.g., no more than one, no more than two, no more than three, no more than four or no more than five) amino acid modification (e.g., substitution, deletion and/or addition) as compared to SEQ ID NO: 5 or SEQ ID NO: 14; and (f) a $V_L$ CDR3 region comprising the amino acid sequence set forth in SEQ ID NO: 6, SEQ ID NO: 15, SEQ ID NO: 16, SEQ ID NO: 17 or SEQ ID NO: 18, or an amino acid sequence having at least one (e.g., no more than one, no more than two, no more than three, no more than four or no more than five) amino acid modification (e.g., substitution, deletion and/or addition) as compared to SEQ ID NO: 6, SEQ ID NO: 15, SEQ ID NO: 16, SEQ ID NO: 17 or SEQ ID NO: 18.

In certain embodiments, a presently disclosed antibody, or antigen-binding portion thereof, comprises: (i) a heavy chain variable region CDR3 comprising the amino acid sequence set forth in SEQ ID NO: 3, SEQ ID NO: 11 or SEQ ID NO: 59, or an amino acid sequence having at least one (e.g., no more than one, no more than two, no more than three, no more than four or no more than five) amino acid modification (e.g., substitution, deletion and/or addition) as compared to SEQ ID NO: 3, SEQ ID NO: 11 or SEQ ID NO: 59; and/or (ii) a light chain variable region CDR3 the amino acid sequence set forth in SEQ ID NO: 6, SEQ ID NO: 15, SEQ ID NO: 16, SEQ ID NO: 17 or SEQ ID NO: 18, or an amino acid sequence having at least one (e.g., no more than one, no more than two, no more than three, no more than four or no more than five) amino acid modification (e.g., substitution, deletion and/or addition) as compared to SEQ ID NO: 6, SEQ ID NO: 15, SEQ ID NO: 16, SEQ ID NO: 17 or SEQ ID NO: 18.

Engineered antibodies of the presently disclosed subject matter include those in which modifications are made to framework residues within $V_H$ and/or $V_K$, e.g., to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, anti-CD56 antibodies or antigen-binding portions thereof of the presently disclosed subject matter may be engineered to include modifications within the Fc region, typically to alter one or more functional properties of the antibody, such as serum half-life, complement fixation, Fc receptor binding, and/or antigen-dependent cellular cytotoxicity. Furthermore, a presently disclosed anti-CD56 antibody may be chemically modified (e.g., one or more chemical moieties can be attached to the antibody) or be modified to alter its glycosylation, again to alter one or more functional properties of the antibody. The hinge region of CH1 may be modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody. The Fc hinge region of an antibody may be mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al. The antibody may be modified to increase its biological half life, e.g., the antibody may be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Furthermore, the Fc region may be altered by replacing at least one amino acid residue with a different amino acid residue to alter the effector function(s) of the antibody. The Fc region may be modified to increase the ability of the antibody to mediate antibody dependent cellular cytotoxicity (ADCC) and/or to increase the affinity of the antibody for an Fcγ receptor, e.g., as described in WO 00/42072 by Presta. In certain embodiments, a presently disclosed anti-CD56 antibody comprises an afucosylated Fc region. Removal of the fucose residue from the N-glycans of the Fc portion of immunoglobulin G (IgG) can result in a dramatic enhancement of ADCC through improved affinity for Fcγ receptor IIIa (FcγRIIIa).

Additionally or alternatively, the glycosylation of an antibody may be modified. For example, an aglycoslated antibody can be made (i.e., the antibody lacks glycosylation). Glycosylation can be altered to, for example, increase the affinity of the antibody for antigen, see e.g., U.S. Pat. Nos. 5,714,350 and 6,350,861. Such carbohydrate modifications can be accomplished by, for example, altering one or more sites of glycosylation within the antibody sequence. For example, one or more amino acid substitution can be made that result in elimination of one or more variable region framework glycosylation sites to thereby eliminate glycosylation at that site.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery.

Another modification of the antibodies may be pegylation. An antibody can be pegylated to, for example, increase the biological (e.g., serum) half life of the antibody. In certain embodiments, to pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation may be carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. The antibody to be pegylated may be an aglycosylated antibody. Methods for pegylating proteins are known in the art and can be applied to the antibodies disclosed herein, see e.g., EP 0154316 and EP 0401384.

VIII. Administration

Anti-CD56 antibodies and antigen-binding fragments thereof and CD56-targeted CARs and immunoresponsive cells expressing thereof of the presently disclosed subject matter can be provided systemically or directly to a subject for treating or preventing a neoplasia. In certain embodiments, anti-CD56 antibodies, or antigen-binding fragments thereof, and CD56-targeted CARs, and immunoresponsive cells expressing thereof are directly injected into an organ of interest (e.g., an organ affected by a neoplasia). Alternatively or additionally, the anti-CD56 antibodies and antigen-binding fragments thereof, CD56-targeted CARs and immunoresponsive cells expressing thereof are provided indirectly to the organ of interest, for example, by administration into the circulatory system (e.g., the tumor vasculature). Expansion and differentiation agents can be provided prior to, during or after administration of cells and compositions to increase production of T cells in vitro or in vivo.

Anti-CD56 antibodies and antigen-binding fragments thereof, CD56-targeted CARs and immunoresponsive cells expressing thereof of the presently disclosed subject matter can be administered in any physiologically acceptable vehicle, normally intravascularly, although they may also be introduced into bone or other convenient site where the cells may find an appropriate site for regeneration and differentiation (e.g., thymus). In certain embodiments, at least $1 \times 10^5$ cells can be administered, eventually reaching $1 \times 10^{10}$ or more. In certain embodiments, at least $1 \times 10^6$ cells can be administered. A cell population comprising immunoresponsive cells expressing a CD56-targeted CAR can comprise a purified population of cells. Those skilled in the art can readily determine the percentage of immunoresponsive cells in a cell population using various well-known methods, such as fluorescence activated cell sorting (FACS). The ranges of purity in cell populations comprising genetically modified immunoresponsive cells expressing a CD56-specific CAR can be from about 50% to about 55%, from about 55% to about 60%, from about 65% to about 70%, from about 70% to about 75%, from about 75% to about 80%, from about 80% to about 85%; from about 85% to about 90%, from about 90% to about 95%, or from about 95 to about 100%. Dosages can be readily adjusted by those skilled in the art (e.g., a decrease in purity may require an increase in dosage). The immunoresponsive cells can be introduced by injection, catheter, or the like. If desired, factors can also be included, including, but not limited to, interleukins, e.g. IL-2, IL-3, IL 6, IL-11, IL-7, IL-12, IL-15, IL-21, as well as the other interleukins, the colony stimulating factors, such as G-, M- and GM-CSF, interferons, e.g., γ-interferon.

In certain embodiments, compositions of the presently disclosed subject matter comprise pharmaceutical compositions comprising immunoresponsive cells expressing a CD56-targeted CAR and a pharmaceutically acceptable carrier. Administration can be autologous or non-autologous. For example, immunoresponsive cells expressing a CD56-targeted CAR and compositions comprising thereof can be obtained from one subject, and administered to the same subject or a different, compatible subject. Peripheral blood derived T cells of the presently disclosed subject matter or their progeny (e.g., in vivo, ex vivo or in vitro derived) can be administered via localized injection, including catheter administration, systemic injection, localized injection, intravenous injection, or parenteral administration. When administering a pharmaceutical composition of the presently disclosed subject matter (e.g., a pharmaceutical composition comprising immunoresponsive cells expressing a CD56-targeted CAR), it can be formulated in a unit dosage injectable form (solution, suspension, emulsion).

In certain embodiments, compositions of the presently disclosed subject matter can comprise one or more antigen-binding proteins such as an anti-CD56 antibody or an antigen-binding fragment thereof, disclosed herein, and a pharmaceutically acceptable carrier.

IX. Formulations

Immunoresponsive cells expressing a presently disclosed CD56-targeted CAR and compositions comprising thereof and/or anti-CD56 antibodies, or antigen-binding fragments thereof, of the presently disclosed subject matter can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the compositions of the presently disclosed subject matter, e.g., a composition comprising immunoresponsive cells expressing a presently disclosed CD56-targeted CAR, in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, alum inurn monostearate and gelatin. According to the presently disclosed subject matter, however, any vehicle, diluent, or additive used would have to be compatible with the immunoresponsive cells expressing a generally CD56-targeted CAR of the presently disclosed subject matter.

The compositions can be isotonic, i.e., they can have the same osmotic pressure as blood and lacrimal fluid. The desired isotonicity of the compositions of the presently disclosed subject matter may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose can be used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the immunoresponsive cells as describe in the presently disclosed subject matter. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of the immunoresponsive cells of the presently disclosed subject matter is the quantity of cells necessary to achieve an optimal effect. The quantity of cells to be administered will vary for the subject being treated. In certain embodiments, from about $10^4$ to about $10^{10}$, from about $10^5$ to about $10^9$, or from about $10^6$ to about $10^8$ immunoresponsive cells of the presently disclosed subject matter are administered to a subject. More effective cells may be administered in even smaller numbers. In some embodiments, at least about $1\times10^8$, about $2\times10^8$, about $3\times10^8$, about $4\times10^8$, and about $5\times10^8$ immunoresponsive cells of the presently disclosed subject matter are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods of the presently disclosed subject matter. Typically, any additives (in addition to the active cell(s) and/or agent(s)) are present in an amount of from about 0.001% to about 50% by weight) solution in phosphate buffered saline, and the active ingredient is present in the order of micrograms to milligrams, such as from about 0.0001 wt % to about 5 wt %, from about 0.0001 wt % to about 1 wt %, from about 0.0001 wt % to about 0.05 wt %, from about 0.001 wt % to about 20 wt %, from about 0.01 wt % to about 10 wt %, or from about 0.05 wt % to about 5 wt %. For any composition to be administered to an animal or human, and for any particular method of administration, toxicity should be determined, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

X. Methods of Treatment

Tumor Microenvironment.

Tumors have a microenvironment that is hostile to the host immune response involving a series of mechanisms by malignant cells to protect themselves from immune recognition and elimination. This "hostile tumor microenvironment" comprises a variety of immune suppressive factors including infiltrating regulatory $CD4^+$ T cells (Tregs), myeloid derived suppressor cells (MDSCs), tumor associated macrophages (TAMs), immune suppressive cytokines including IL-10 and TGF-β, and expression of ligands targeted to immune suppressive receptors expressed by activated T cells (CTLA-4 and PD-1). These mechanisms of immune suppression play a role in the maintenance of tolerance and suppressing inappropriate immune responses, however within the tumor microenvironment these mechanisms prevent an effective anti-tumor immune response. Collectively these immune suppressive factors can induce either marked anergy or apoptosis of adoptively transferred CAR modified T cells upon encounter with targeted tumor cells.

Challenges in Tumor Immunology.

Effective tumor immunity requires recognition of tumor antigens and unopposed tumor elimination by immune effector cells. Tumor antigens must contain peptide epitopes that are presented by the tumor and can be recognized by specific cytotoxic T lymphocytes (CTLs). The primed CTLs must expand to a sufficient number and migrate to tumor sites, wherein they mature into effectors to perform their functions, which are enhanced by helper T cells and dampened by Tregs and inhibitory macrophages.

Targeted T Cell Therapy with Engineered T Lymphocytes.

T cell engineering is a groundbreaking strategy to potentially resolve many previously observed shortcomings of earlier immunotherapeutic approaches. Within the past year, researchers have reported dramatic complete remissions in relapsed (Brentjens, R. J., et al. Safety and persistence of adoptively transferred autologous CD19-targeted T cells in patients with relapsed or chemotherapy refractory B-cell leukemias. *Blood* 118, 4817-4828 (2011); Brentjens, R. J., et al. CD19-targeted T cells rapidly induce molecular remissions in adults with chemotherapy-refractory acute lymphoblastic leukemia. Science translational medicine 5, 177ra138 (2013)), chemorefractory leukemia and metastatic melanoma (Hunder, N. N., et al. Treatment of metastatic melanoma with autologous CD4+ T cells against NY-ESO-1. *N. Engl. J. Med.* 358, 2698-2703 (2008); Rosenberg, S. A., Restifo, N. P., Yang, J. C., Morgan, R. A. & Dudley, M. E. Adoptive cell transfer: a clinical path to effective cancer immunotherapy. *Nat. Rev. Cancer* 8, 299-308 (2008); Dudley, M. E., et al. Adoptive cell therapy for patients with metastatic melanoma: evaluation of intensive myeloablative chemoradiation preparative regimens. *J Clin Oncol* 26, 5233-5239 (2008)), obtained with autologous peripheral blood T cells targeted to a defined antigen (CD19 and NY-ESO-1, respectively).

Rationale for a Genetic Approach:

Cell engineering can be used to redirect T cells toward tumor antigens and to enhance T cell function. One impetus for genetic T cell modification is the potential to enhance T cell survival and expansion and to offset T cell death, anergy, and immune suppression. The genetic targeting of T cells can also be refined to prevent undesired destruction of normal tissues.

Chimeric Antigen Receptors (CARs):

Tumor-specific T cells can be generated by the transfer of genes that encode CARs (Brentjens, R. J., et al. Genetically targeted T cells eradicate systemic acute lymphoblastic leukemia xenografts. *Clin. Cancer Res.* 13, 5426-5435 (2007); Gade, T. P., et al. Targeted elimination of prostate cancer by genetically directed human T lymphocytes. *Cancer Res.* 65, 9080-9088 (2005); Maher, J., Brentjens, R. J., Gunset, G., Riviere, I. & Sadelain, M. Human T-lymphocyte cytotoxicity and proliferation directed by a single chimeric TCRzeta/CD28 receptor. *Nat. Biotechnol.* 20, 70-75 (2002); Kershaw, M. H., et al. Gene-engineered T cells as a superior adjuvant therapy for metastatic cancer. *J Immunol* 173, 2143-2150 (2004); Sadelain, M., Brentjens, R. & Riviere, I. The promise and potential pitfalls of chimeric antigen receptors. *Curr Opin Immunol* (2009); Hollyman, D., et al. Manufacturing validation of biologically functional T cells targeted to CD19 antigen for autologous adoptive cell therapy. *J Immunother* 32, 169-180 (2009)). Second-generation CARs comprise a tumor antigen-binding domain fused to an intracellular signaling domain capable of activating T cells and a co-stimulatory domain designed to augment T cell potency and persistence (Sadelain, M., Brentjens, R. & Riviere, I. The basic principles of chimeric antigen receptor design. *Cancer discovery* 3, 388-398 (2013)). CAR design can therefore reconcile antigen recognition with signal transduction, two functions that are physiologically borne by two separate complexes, the TCR heterodimer and the CD3 complex. The CAR's extracellular antigen-binding domain is usually derived from a murine monoclonal antibody (mAb) or from receptors or their ligands. Antigen recognition is therefore not MHC-restricted (Riviere, I., Sadelain, M. & Brentjens, R. J. Novel strategies for cancer therapy: the potential of genetically modified T lymphocytes. *Curr Hematol Rep* 3, 290-297 (2004); Stephan, M. T., et al. T cell-encoded CD80 and 4-1BBL induce auto- and transco-stimulation, resulting in potent tumor rejection. *Nat. Med.* 13, 1440-1449 (2007)) and is therefore applicable to any patient expressing the target antigen, using the same CAR. Antigen binding by the CARs triggers phosphorylation of immunoreceptor tyrosine-based activation motifs (ITAMs) in the intracellular domain, initiating a signaling cascade required for cytolysis induction, cytokine secretion, and proliferation. Because MHC restriction of antigen recognition is bypassed, the function of CAR-targeted T cells is not affected by HLA downregulation or defects in the antigen-processing machinery.

T Cell Requirements for Expansion and Survival:

Proliferation of tumor-specific T cells is needed ex vivo and is arguably desirable in vivo. T cell proliferation must be accompanied by T cell survival to permit absolute T cell expansion and persistence. To proliferate in response to antigen, T cells must receive two signals. One is provided by TCR recognition of antigenic peptide/MHC complexes displayed on the surface of antigen-presenting cells (APCs) (Sadelain (2009). The other is provided by a T cell co-stimulatory receptor, such as the CD28 or 4-1BB receptors. Whereas the cytolytic activity of T cells does not require concomitant co-stimulation, there is a critical need for the provision of co-stimulatory signals to sustain the antitumor functions of adoptively transferred T cells, as previously demonstrated (Maher (2002); Sadelain (2013); Krause, A., et al. Antigen-dependent CD28 signaling selectively enhances survival and proliferation in genetically modified activated human primary T lymphocytes. *J Exp Med* 188, 619-626 (1998); Gong, M. C., et al. Cancer patient T cells genetically targeted to prostate-specific membrane antigen specifically lyse prostate cancer cells and release cytokines in response to prostate-specific membrane antigen. *Neoplasia.* 1, 123-127 (1999); Lyddane, C., et al. Cutting Edge: CD28 controls dominant regulatory T cell activity during active immunization. *J. Immunol.* 176, 3306-3310 (2006).

Immune Monitoring:

Lymphocytes are multifunctional "drugs" that exhibit dynamically evolving effects after infusion. Upon antigen encounter, tumor-specific T cells activate and/or release a variety of proteins that can trigger tumor killing, T cell proliferation, and recruitment or immunomodulation of other immune cells. Thus, measuring which proteins are secreted from which cells, in what quantity, and at what time point yields profound insights into why a particular patient is or is not responding and provides critical feedback for designing more-effective trials. These assay systems will permit direct and meaningful comparisons of clinical approaches and thus help design rational, next-generation therapeutic strategies.

For treatment, the amount administered is an amount effective in producing the desired effect. An effective amount can be provided in one or a series of administrations. An effective amount can be provided in a bolus or by continuous perfusion.

For adoptive immunotherapy using antigen-specific T cells, cell doses in the range of about $10^6$ to about $10^{10}$ (e.g., about $10^9$ or about $10^6$) are typically infused. Upon administration of the immunoresponsive cells into the subject and subsequent differentiation, the immunoresponsive cells are induced that are specifically directed against one specific antigen (e.g., CD56). "Induction" of T cells can include inactivation of antigen-specific T cells such as by deletion or anergy. Inactivation is particularly useful to establish or reestablish tolerance such as in autoimmune disorders. The immunoresponsive cells of the presently disclosed subject matter can be administered by any methods known in the art, including, but not limited to, pleural administration, intravenous administration, subcutaneous administration, intranodal administration, intratumoral administration, intrathecal administration, intrapleural administration, intraperitoneal administration, and direct administration to the thymus. In certain embodiments, the immunoresponsive cells and the compositions comprising thereof are intravenously administered to the subject in need.

The presently disclosed subject matter provides various methods of using the immunoresponsive cells (e.g., T cells) expressing a CD56-targeted CAR or anti-CD56 antibodies (or antigen-binding fragments thereof). For example, the presently disclosed subject matter provides methods of reducing tumor burden in a subject. In one non-limiting example, the method of reducing tumor burden comprises administering an effective amount of the presently disclosed immunoresponsive cell to the subject, thereby inducing tumor cell death in the subject. The presently disclosed immunoresponsive cell can reduce the number of tumor cells, reduce tumor size, and/or eradicate the tumor in the subject. In certain embodiments, the method of reducing tumor burden comprises administering an effective amount of one or more of the presently disclosed anti-CD56 antibodies (or antigen-binding fragments thereof) to the subject, thereby inducing tumor cell death in the subject. Non-limiting examples of suitable tumors include multiple myeloma, neuroblastoma, glioma, acute myeloid leukemia, colon cancer, pancreatic cancer, thyroid cancer, small cell lung cancer, and NK cell lymphoma. In certain embodiments, the tumor is multiple myeloma.

The presently disclosed subject matter also provides methods of increasing or lengthening survival of a subject having a neoplasia. In one non-limiting example, the method of increasing or lengthening survival of a subject having neoplasia comprises administering an effective amount of the presently disclosed immunoresponsive cell to the subject, thereby increasing or lengthening survival of the subject. In certain embodiments, the method of increasing or lengthening survival of a subject having neoplasia comprises administering an effective amount of one or more of the presently disclosed anti-CD56 antibodies (or antigen-binding fragments thereof) to the subject, thereby increasing or lengthening survival of the subject. The method can reduce or eradicate tumor burden in the subject. The presently disclosed subject matter further provides methods for treating or preventing a neoplasia in a subject, comprising administering the presently disclosed immunoresponsive cell or anti-CD56 antibody (or antigen-binding fragment thereof) to the subject.

Cancers whose growth may be inhibited using the immunoresponsive cells of the presently disclosed subject matter comprise cancers typically responsive to immunotherapy. Non-limiting examples of cancers for treatment include multiple myeloma, neuroblastoma, glioma, acute myeloid leukemia, colon cancer, pancreatic cancer, thyroid cancer, small cell lung cancer, and NK cell lymphoma. In certain embodiments, the cancer is multiple myeloma.

Additionally, the presently disclosed subject matter provides methods of increasing immune-activating cytokine production in response to a cancer cell in a subject. In one non-limiting example, the method comprises administering the presently disclosed immunoresponsive cell to the subject. The immune-activating cytokine can be granulocyte macrophage colony stimulating factor (GM-CSF), IFN-α, IFN-β, IFN-γ, TNF-α, IL-2, IL-3, IL-6, IL-11, IL-7, IL-12, IL-15, IL-21, interferon regulatory factor 7 (IRF7), and combinations thereof. In certain embodiments, the immunoresponsive cells including a CD56-specific CAR of the presently disclosed subject matter increase the production of GM-CSF, IFN-γ, and/or TNF-α.

Suitable human subjects for therapy typically comprise two treatment groups that can be distinguished by clinical criteria. Subjects with "advanced disease" or "high tumor burden" are those who bear a clinically measurable tumor (e.g., multiple myeloma). A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition embodied in the presently disclosed subject matter is administered to these subjects to elicit an anti-tumor response, with the objective of palliating their condition. Ideally, reduction in tumor mass occurs as a result, but any clinical improvement constitutes a benefit. Clinical improvement comprises decreased risk or rate of progression or reduction in pathological consequences of the tumor (e.g., multiple myeloma).

A second group of suitable subjects is known in the art as the "adjuvant group." These are individuals who have had a history of neoplasia (e.g., multiple myeloma), but have been responsive to another mode of therapy. The prior therapy can have included, but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for each different neoplasia. Features typical of high-risk subgroups are those in which the tumor (e.g., multiple myeloma) has invaded neighboring tissues, or who show involvement of lymph nodes. Another group has a genetic predisposition to neoplasia (e.g., multiple myeloma) but has not yet evidenced clinical signs of neoplasia (e.g., multiple myeloma). For instance, women testing positive for a genetic mutation associated with breast cancer, but still of childbearing age, can wish to receive one or more of the antigen-binding fragments described herein in treatment prophylactically to prevent the occurrence of neoplasia until it is suitable to perform preventive surgery.

The subjects can have an advanced form of disease (e.g., multiple myeloma), in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Further modification can be introduced to the CD56-targeted CAR-expressing immunoresponsive cells (e.g., T cells) to avert or minimize the risks of immunological complications (known as "malignant T-cell transformation"), e.g., graft versus-host disease (GvHD), or when healthy tissues express the same target antigens as the tumor cells, leading to outcomes similar to GvHD. A potential solution to this problem is engineering a suicide gene into the CD56-targeted CAR-expressing T cells. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. In certain embodiments, the suicide gene is an EGFRt polypeptide. The EGFRt polypeptide can enable T cell elimination by administering anti-EGFR monoclonal antibody (e.g., cetuximab). EGFRt can be covalently joined to the 3' terminus of the intracellular domain of the CD56-targeted CAR. The suicide gene can be included within the vector comprising nucleic acids encoding the presently disclosed CD56-targeted CARs. In this way, administration of a prodrug designed to activate the suicide gene (e.g., a prodrug (e.g., AP1903 that can activates iCasp-9) during malignant T-cell transformation (e.g., GVHD) triggers apoptosis in the suicide gene-activated CAR-expressing T cells. The incorporation of a suicide gene into the a presently disclosed CD56-targeted CAR gives an added level of safety with the ability to eliminate the majority of CAR T cells within a very short time period. A presently disclosed immunoresponsive cell (e.g., a T cell) incorporated with a suicide gene can be pre-emptively eliminated at a given timepoint post CAR T cell infusion, or eradicated at the earliest signs of toxicity.

XI. Kits

The presently disclosed subject matter provides kits for the treatment or prevention of a neoplasia (e.g., multiple myeloma). In certain embodiments, the kit comprises a therapeutic or prophylactic composition containing an effective amount of an immunoresponsive cell comprising a CD56-targeted CAR in unit dosage form. In particular embodiments, the cells further expresses at least one co-stimulatory ligand. In certain embodiments, the kit comprises a therapeutic or prophylactic composition containing an effective amount of an anti-CD56 antibody or antigen-binding fragment thereof in unit dosage form. In some embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, the immunoresponsive cell and/or an anti-CD56 antibody (or antigen-binding fragment thereof) can be provided together with instructions for administering the cell and/or anti-CD56 antibody to a subject having or at risk of developing a neoplasia (e.g., multiple myeloma). The instructions will generally include information about the use of the composition for the treatment or prevention of a neoplasia (e.g., multiple myeloma). In other embodiments, the instructions include at least one of the following: description of the therapeutic agent; dosage schedule and administration for treatment or prevention of a neoplasia (e.g., multiple myeloma) or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the compositions, and assay, screening, and therapeutic methods of the invention, and are not intended to limit the scope of what the inventors regard as their invention.

Example 1—Generation and CTL Activity of CD56-Specific CARs

CARs based on the following scFv's were generated: m903, m904, m905, m906, and m900 (also referred to herein as m907) according to the structure shown in FIG. 1. The binding affinities of m903, m904, m905, m906, and m900 to human CD56 were assessed by Biacore analysis, and the results are summarized in Table 7 below. It was found that m900 binds to a different epitope on human CD56 from m903, m904, m905, and m906, and m903, m904, m905, and m906 bind to the same epitope on human CD56. CAR m900 has the highest binding affinity to human CD56.

TABLE 7

| CD56 Fabs | CD56 Fabs | KD (M) |
| --- | --- | --- |
| m900* | Fab43 | $2.902 \times 10^{-9}$ |
| m906 | Fab46-19 | $4.490 \times 10^{-9}$ |
| m905 | Fab46-8 | $9.172 \times 10^{-9}$ |
|  | Fab46 | $8.382 \times 10^{-8}$ |
| m904 | Fab46-H3 | $9.088 \times 10^{-8}$ |
| m903 | Fab46-E5 | $2.365 \times 10^{-7}$ |

The CTL activity of these CARs as well as a CAR comprising a scFv of the murine monoclonal anti-CD56 antibody N901 ("56-28z") were assessed. As shown in FIGS. 2A and 2B, m900 exhibited the highest CTL activity against high CD56-expressing cells but little CTL activity against low CD56-expressing cells. Thus, CAR m900 can have strong and selective antitumor activity against cancerous cells, e.g., myeloma cells, which are almost always CD56 high-expressing cells whilst sparing normal NK and NK T cells, which are CD56-low expressing cells. One explanation for the result is the avidity effect brought into play by high target cell antigen density.

Figure 5A:
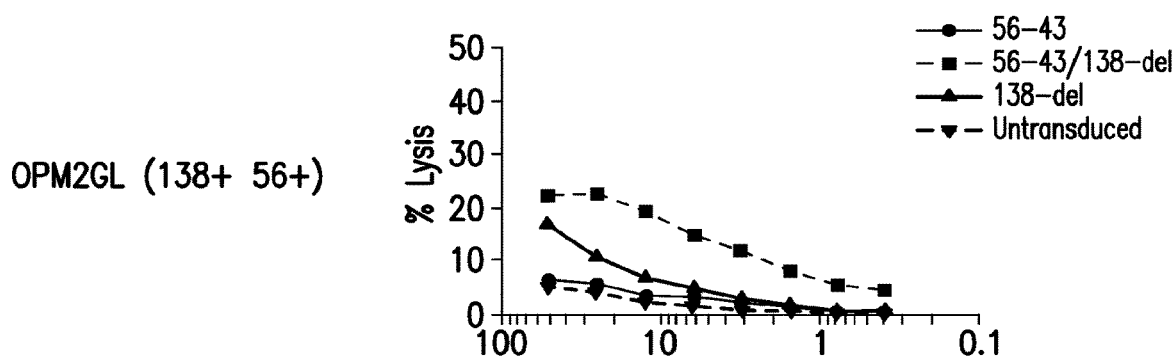
FIGS. 5A-5D depict the CTL activity of an immunoresponsive cell comprising a CD56-targeted CAR and a truncated CAR in accordance with one non-limiting embodiment of the presently disclosed subject matter.
Figure 5B:
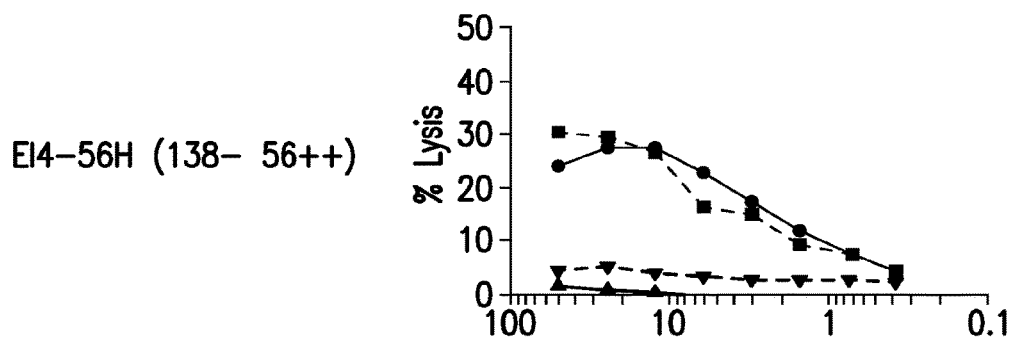
Figures 5C, 5D:
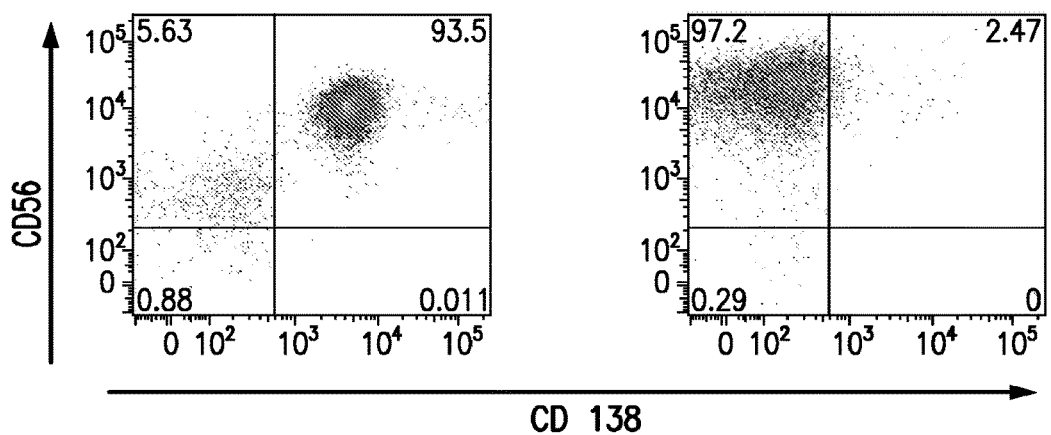

Example 2—CTL Activity of a T Cell Expressing a CD56-Specific CAR and a Truncated CAR A T cell expressing CAR m900 and a truncated CAR targeting CD138 was generated. The truncated CAR comprises a scFv that binds to CD138, and a transmembrane domain comprising a CD8 polypeptide (referred to as "138del"). The CTL activities of T cells expressing CAR m900 alone and T cells expressing a combination of CAR m900 and 138del (referred to as "CAR m900+138del") were assessed. As shown in FIGS. 5A and 5B, the CTL activity of m900 was comparable to the CTL activity of CAR m900+138del.

Example 3—CD56 Targeted Immunotherapy for Multiple Myeloma Using Chimeric Antigen Receptors 3.1 Methods
CARs and Vectors:
Syntheses of SFG-19z1-ΔLNGFR and SFG-19-28z have been previously described (Markley and Sadelain, IL-7 and IL-21 are superior to IL-2 and IL-15 in promoting human T cell-mediated rejection of systemic lymphoma in immunodeficient mice. *Blood.* 115(17):3508-3519 (2010)). The SFG-19z1-ΔLNGFR plasmid that includes a P2A bicistronic element was used as a template to obtain SFG-P28z-ΔLNGFR and SFG-19-28z-ΔLNGFR constructs. The sequence of the murine anti hCD56 antibody N901 (Roguska, et al. Humanization of murine monoclonal antibodies through variable domain resurfacing. *Proc Natl Acad Sci USA.* 91(3):969-973 (1994)) was codon optimized and substituted as an NcoI-N901scFv-NotI oligonucleotide to create the SFG-56-28z-ΔLNGFR construct. Similarly, the sequences of m903, m904, m905, m906 and m900 anti-CD56 scFvs (see Tables 1-5) generated by phage display technology were used to create SFG-m903-28z-ΔLNGFR, SFG-m904-28z-ΔLNGFR, SFG-m905-28z-ΔLNGFR, SFG-m906-28z-ΔLNGFR and SFG-m900-28z-ΔLNGFR constructs, respectively. VSV-G pseudotyped retroviral derived from transduced gpg29 fibroblasts (H29) were used to construct stable PG13 packaging cell lines as previously described (Ghani, et al. Efficient human hematopoietic cell transduction using RD114- and GALV-pseudotyped retroviral vectors produced in suspension and serum-free media. *Hum Gene Ther.* 20(9):966-974 (2009)).

Cell Lines:

The human myeloma cell line OPM2 was obtained from ATCC and stably transduced to express firefly luciferase-GFP (OPM2-GL) using established methods (Brentjens, et al. Genetically targeted T cells eradicate systemic acute lymphoblastic leukemia xenografts. *Clin Cancer Res.* 13(18 Pt 1):5426-5435 (2007)). OPM2 cells were also engineered to express human CD19 (OPM2-19). EL4 murine leukemia cells were retrovirally transduced with human CD56 (hCD56) using the SFG-hCD56$^{1401D}$ retroviral construct and sorted into high and low hCD56-expressing cells (E14-56H, EL4-56L) by fluorescence activated cell sorting. OPM2 and EL4 cell lines as well as their derivatives were cultured in RPMI 1640 (Life Technologies) supplemented with 10% heat-inactivated FCS, nonessential amino acids, HEPES buffer, pyruvate, and BME (Life Technologies). The 293T cell line, H29 and retroviral packaging cell lines were cultured in DMEM (Life Technologies) supplemented with 10% FCS, 2 mM L-glutamine, 100 units/mL penicillin and 100 μg/mL streptomycin (Life Technologies).

CD56 Fab Selection:

CD56-binding Fabs were selected with phage display technology in two steps, as previously described (Feng, et al. A novel human monoclonal antibody that binds with high affinity to mesothelin-expressing cells and kills them by antibody-dependent cell-mediated cytotoxicity. *Mol Cancer Ther.* 8(5):1113-1118 (2009)). Firstly, CD56 Fabs were identified by panning and screening of a large naïve human antibody library through multiple rounds of binding and amplification. In the second step, the selected clone with the best in vitro and in vivo binding property was affinity matured through a light chain shuffling process, where the VH of the clone was combined with the VL repertoire from the original library. The sub-library was further panned and screened with CD56 to obtain Fab clones with the same epitope but different affinities. Binding of the Fabs was confirmed with ELISA and affinities estimated with Surface Plasmon Resonance method on a Biacore Processing unit X100. Four clones specific for the same epitope, termed m903, m904, m905 and m906, and m900, recognizing a different epitope, were used in their single chain format (VH-(G45)3-VL) to construct CARs.

T Cell Function Assays:

Blood samples were obtained from healthy volunteers under an institutional review board-approved protocol, in accordance with the Declaration of Helsinki. PBMC were isolated by low-density centrifugation on Lymphoprep (Accurate Chemical and Scientific Corporation, Westbury, N.Y.), activated with PHA for 48 h and transduced on two consecutive days by centrifugation on retronectin-coated (Takara), oncoretroviral vector-bound plates. Seven days after PHA stimulation, transduced T cells were stained for transduction rate measurements and either injected into tumor bearing mice or cocultured with irradiated confluent OPM2 cells at $10^6$ cells/ml in 24-well tissue culture plates in RPMI medium supplemented with 10% FCS, 1-glutamine, streptomycin, and penicillin, in the presence of interleukin-2 at a concentration of 20 IU/ml. Identical stimulations in fresh medium were performed weekly and manual T cell counts done twice weekly. T-cell cultures were supplemented with fresh medium to maintain a concentration of $1.5$-$2 \times 10^6$ cell s/ml.

Cytokine Assays:

Supernatants were harvested 24 h after T-cell stimulation and secreted cytokines measured using a custom multiplex system HCYTMAG-60K (Millipore), according to the manufacturer's instructions. Luminescence was assessed using the Luminex IS100 device and analyzed for cytokine concentration using IS 2.2 software (Luminex Corp.).

Cytotoxicity Assays:

The cytotoxic activity of transduced T cells was determined by standard $^{51}$Chromium release assays (Gong, et al. Cancer patient T cells genetically targeted to prostate-specific membrane antigen specifically lyse prostate cancer cells and release cytokines in response to prostate-specific membrane antigen. Neoplasia. 1(2):123-127 (1999)). Briefly, transduced T cells were assessed by fluorescence-activated cell sorting analysis for CAR expression on day 4 after transduction. $^{51}$Cr-labelled OPM2-19 tumor cells were resuspended at a concentration of $1 \times 10^5$ tumor cells/mL and admixed with transduced T cells at varying CAR+ effector T cell to target cell ratios in 96-well tissue culture plates in a final volume of 200 µl. After 4 hours, 30 µl of supernatant was analyzed using Lumaplate-96 microplates (Packard Bioscience) by a Top Count NXT microplate scintillation counter (Packard Bioscience).

Myeloma Animal Model and Imaging:

A xenograft model of myeloma was developed by intravenously injecting $2 \times 10^6$ OPM2-GL cells into 6-8 week old NOD/SCID©c$^{null}$(NSG) mice. CAR transduced T cells were injected i.v. into tumor bearing mice 7 days after having demonstrated tumor engraftment by bioluminescence imaging (BLI) using the Xenogen IVIS Imaging System (Xenogen) with Living Image software (Xenogen) for acquisition of imaging data sets. Image acquisition was done on a 20-cm field of view at medium binning level for 0.2- to 2-min exposure time. Both dorsal and ventral views were obtained on all animals. Tumor burden, as determined by IVIS imaging, was quantified as described previously (Gong et al. Cancer patient T cells genetically targeted to prostate-specific membrane antigen specifically lyse prostate cancer cells and release cytokines in response to prostate-specific membrane antigen. Neoplasia. 1(2):123-127 (1999); Gade, et al. Targeted elimination of prostate cancer by genetically directed human T lymphocytes. Cancer Res. 65(19):9080-9088 (2005)). Mice were bled at regular intervals to quantify the number of circulating CAR+ T cells by FACS analysis, to measure plasma levels of human Th1 cytokines by Luminex assay and human IgGX, levels, a surrogate marker of disease burden, by ELISA (Human Lambda ELISA kit, Bethyl Laboratories Inc).

Bone Studies:

Bone histomorphometry and micro-computed tomography (microCT) imaging were performed by Pharmatest Services Ltd using published methodology (Bouxsein, et al. Guldberg R E, Jepsen K J, Muller R. Guidelines for assessment of bone microstructure in rodents using micro-computed tomography. J. Bone Miner. Res. 25(7):1468-1486 (2010)). Analysis of murine bones was carried out at 4 weeks following tumor injection. Hind limbs of mice were fixed in 4% paraformaldehyde then decalcified in 10% EDTA for two weeks before embedding in paraffin. Mid-sagittal sections were cut, stained with Masson-Goldner Trichrome (MGT) stain and images taken at a magnification of 20×. Trabecular and cortical bone areas and tumor area were measured from MGT sections using MetaMorph software. MicroCT imaging was performed with high-resolution SkyScan 1072 equipment (SkyScan, Kontich, Belgium) to analyze the amount and microarchitecture of trabecular and cortical bone in mouse femora and to prepare representative sample images.

Statistical Analyses:

Data were analyzed using Prism 5.0 (GraphPad Software, Inc.). Statistical comparisons between two groups were determined by the Student's t test. All p values are two-tailed. The Log-rank test was used to compare Kaplan-Meier survival curves.

3.2 Results

CD56-Specific CARs are Stably Expressed in Human T Cells and Direct CD56-Dependent T Cell Expansion and Cytokine Production In Vitro.

A CAR, termed 56-28z, was constructed in which a codon-optimized scFv derived from the N901 monoclonal antibody was fused to CD28/CD3z domains as previously described (Maher, et al. Human T-lymphocyte cytotoxicity and proliferation directed by a single chimeric TCRzeta/CD28 receptor. Nat Biotechnol. 20(1):70-75 (2002)). Primary T cells from healthy human donors were transduced with a bicistronic retroviral vector encoding 56-28z and an inactive LNGFR mutant (FIG. 1), typically showing 40-60% efficiency by FACS analysis. T cells transduced with similar CARs specific for CD19 or PSMA (19-28z and P28z, respectively) were used as controls. Western blot analysis of 56-28z-transduced T cells confirmed CAR structure at the predicted molecular weight (FIG. 6A). Surface expression of 56-28z was shown by flow cytometric analysis using a CAR-specific antibody and specific binding to biotinylated soluble human CD56 (FIG. 6B).

Figure 7:
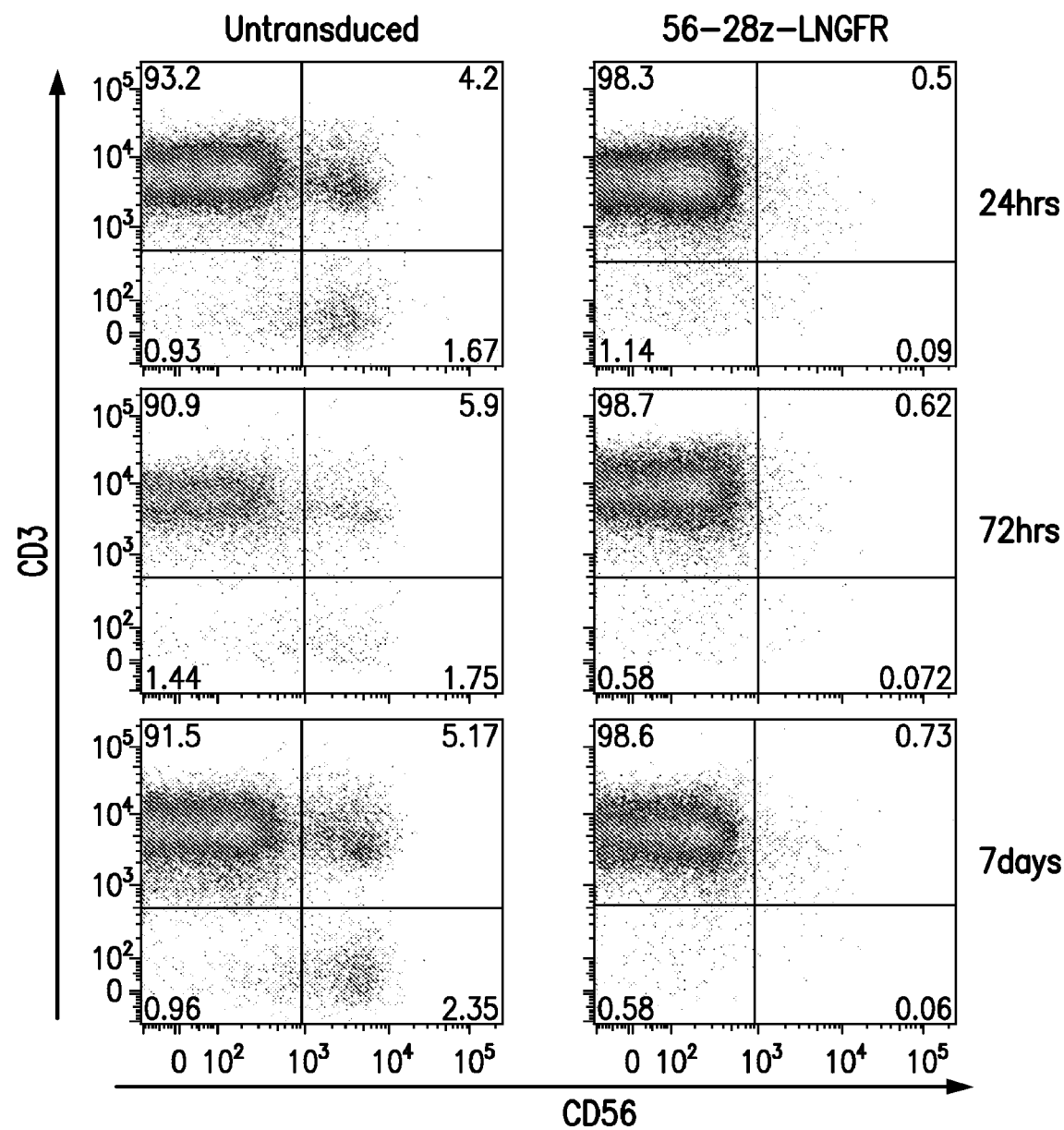
FIG. 7 depicts the FACS plots of untransduced T cells or 56-28z-LNGFR CARs following APC stimulation in vitro showing elimination of 56+ cells.

Following once weekly stimulation with CD56+ myeloma cells in the presence of interleukin-2, 56-28z-transduced T cells expanded by up to 100-fold within fourteen days, in contrast to control P28z T cells which failed to expand under identical conditions (FIG. 6C). Fratricide T cell killing due to CD56 expression in a fraction of human T cells and its up-regulation upon T cell activation was anticipated (FIG. 7). 56-28z CAR T cells indeed rapidly eliminated the preexisting CD56+ T cell fraction and thereafter expanded just as well as control 19-28z-transduced T cells following exposure to CD56 or CD19, respectively. The functionality of 56-28z T cells was further supported by their comparable secretion of Th1 effector cytokines IFN-χ, IL-2 and TNF-α in response to CD56 antigen stimulation (FIG. 6D).

56-28z-transduced T cells efficiently lysed CD56+ myeloma cell lines as well as primary myeloma cells in vitro.

Figure 8A:
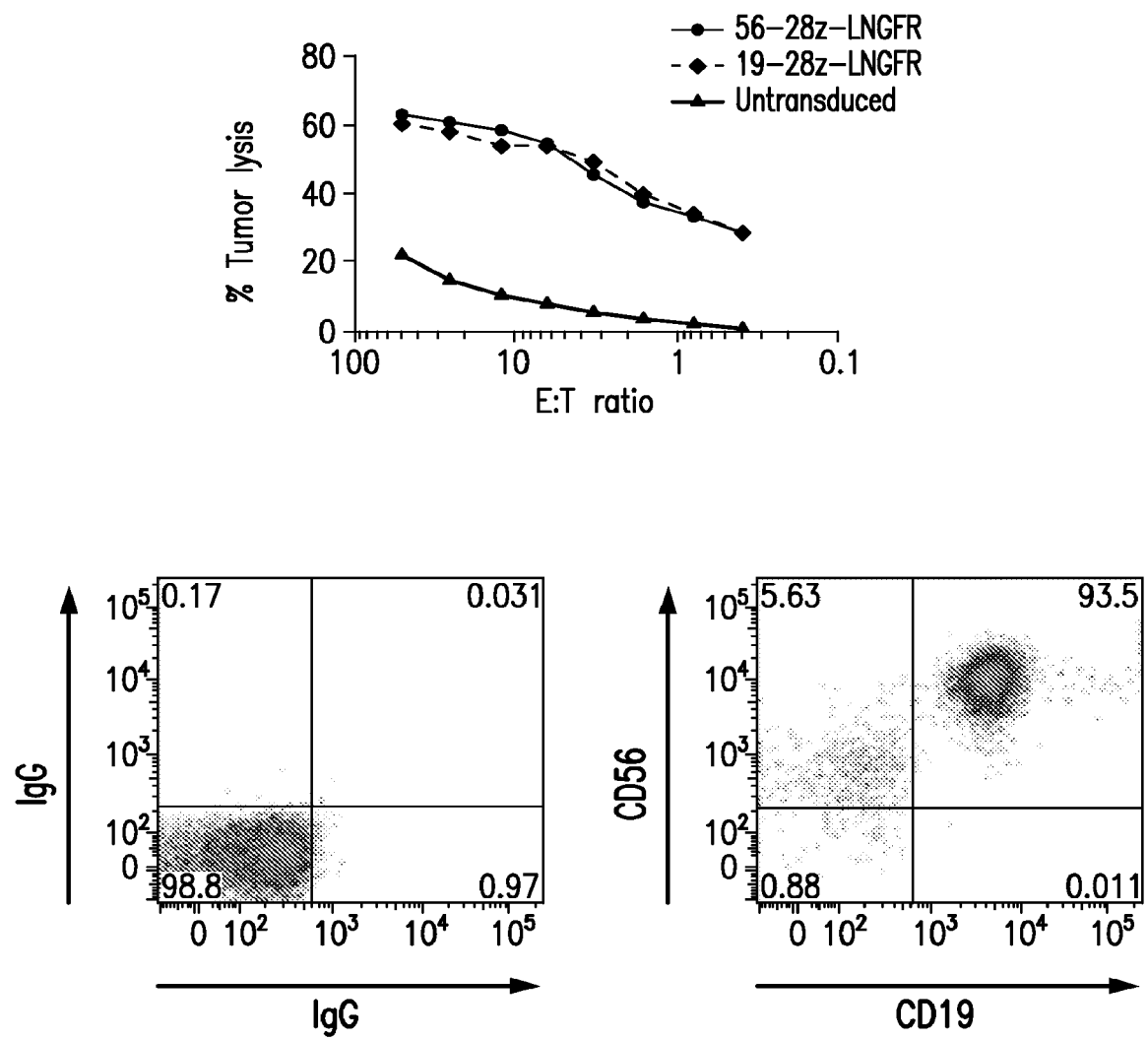
FIGS. 8A-8B depict cytotoxicity of 56-28z cAR transduced T cells. 56-28z CAR transduced T cells show cytotoxicity against $CD56^+$ myeloma cell lines as well as primary myeloma cells in vitro. (A) OPM2-19 tumor lysis by 56-28z CAR, 19-28z CAR or untransduced T cells from a normal donor was assessed by standard 4 hour $Cr^{51}$ release assays. The effector to target (E:T) ratios are normalized to the $CAR^+$ T cell fraction. FACS plots show surface expression of CD56 and CD19 on the OPM2-19 cell line. Results are representative of experiments done using T cells from 3 separate normal donors. (B) CTL assays showing tumor specific lysis of CD138 selected primary myeloma cells from two different patients with relapsed multiple myeloma (MM1 and MM2). 56-28z CAR transduced T cells (●) or untransduced (■) T cells from normal donors were used as effector cells. FACS plots on the right show the level of CD56 expression of these primary myeloma cells.

56-28z-transduced peripheral blood T cells rapidly acquired marked cytolytic activity against CD56+ myeloma cell lines in vitro, as shown by high tumor lysis in a 4-hour $^{51}$Cr release assay even at low effector:target (E:T) ratios (FIG. 8A). This degree of cytotoxicity was similar to that seen with the 19-28z CAR utilized in prior clinical trials (Brentjens, et al. CD19-targeted T cells rapidly induce molecular remissions in adults with chemotherapy-refractory acute lymphoblastic leukemia. Sci Transl Med. 5(177): 177ra138 (2013)).

Figure 8B:
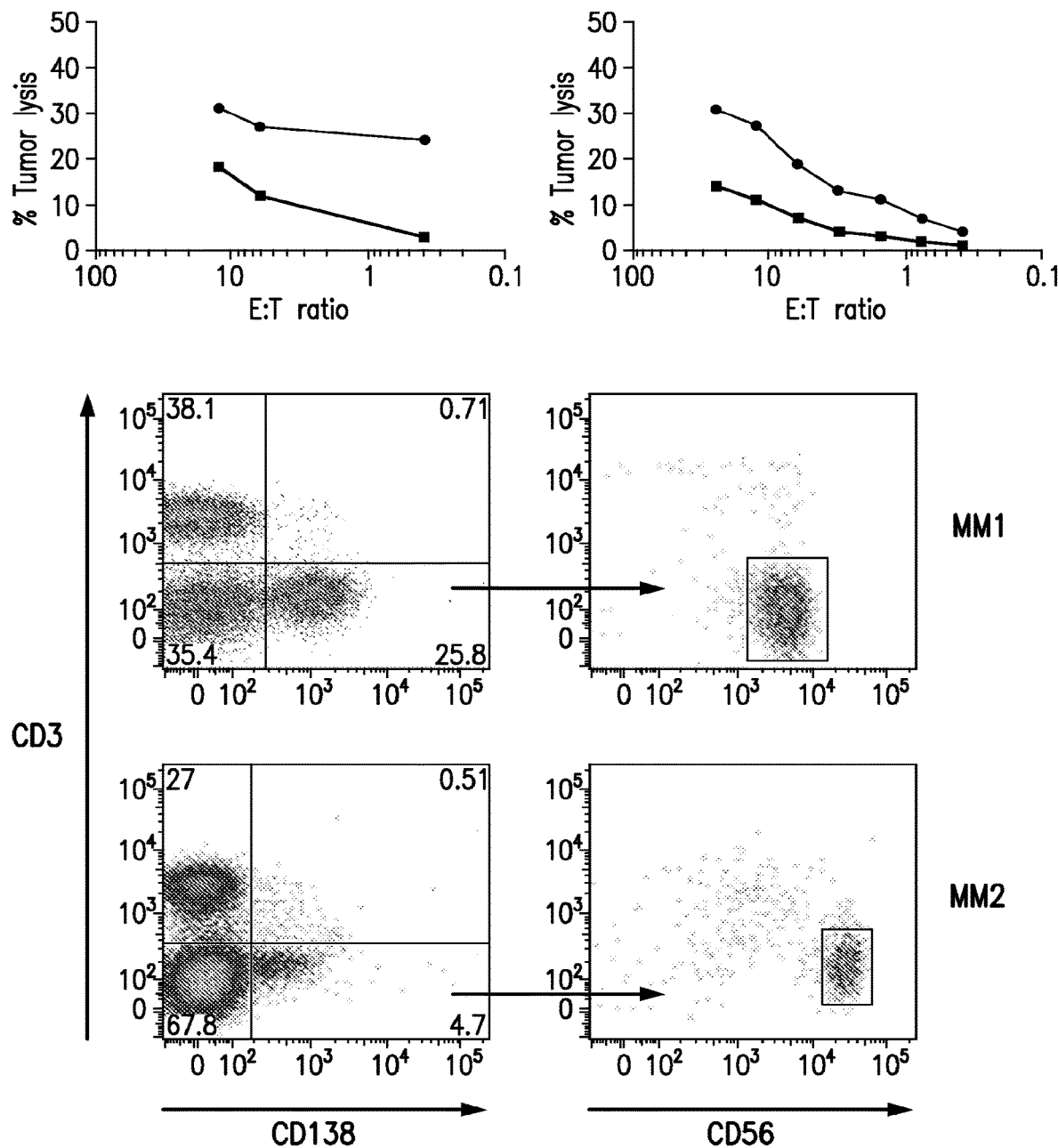

56-28z-transduced T cells were also found to effectively lyse primary myeloma cells from patients with relapsed, refractory disease. Primary myeloma cells were freshly isolated from bone marrow aspirates using CD138 magnetic beads and CD56 expression confirmed by FACS analysis. Cytotoxicity assays were performed using either 56-28z-transduced or untransduced T cells from normal donors. CAR-mediated tumor lysis was consistently observed, markedly exceeding the background level of tumor lysis (FIG. 8B).

56-28z CAR Therapy Eradicated Myeloma Tumor Cells in a Novel Xenograft Model of Multiple Myeloma and Prolonged Tumor Free Survival.

In order to investigate the efficacy of 56-28z CAR therapy against myeloma cells in vivo, a novel xenograft myeloma model was developed in which the OPM2 myeloma cell line, modified to express firefly luciferase, was infused intravenously into immunodeficient NOD/SCID©c$^{null}$(NSG) mice. Tumor cells grew rapidly in the bone marrow, causing hind limb paralysis within 35 days. This model replicates the phenotype of human myeloma with tumor largely confined to the bone marrow compartment, the secretion of monoclonal serum immunoglobulin (hIgGλ), and clear evidence of cortical and trabecular osteolytic myeloma bone disease (FIGS. 9 and 10).

Figure 9A:
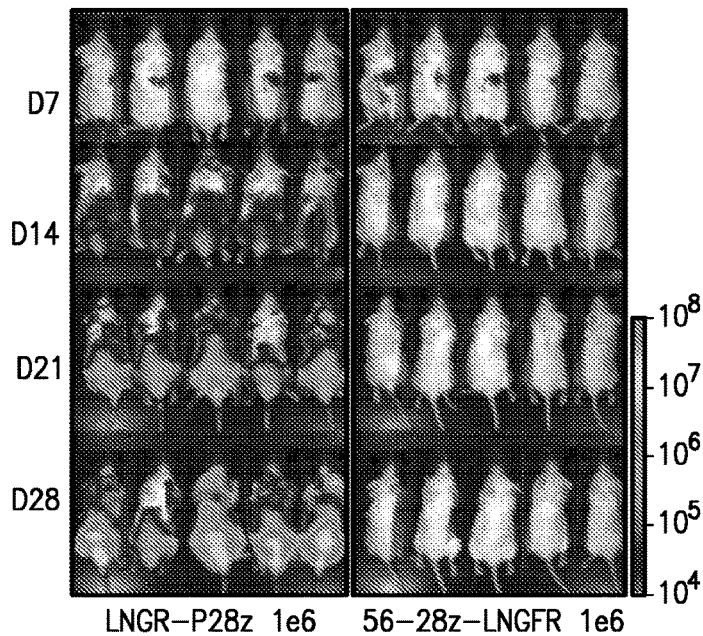
FIGS. 9A-9E depict therapeutic activity of 56-28z CAR. 56-28z CAR therapy in vivo eradicates myeloma tumor cells in a novel xenograft model of multiple myeloma and prolongs tumor free survival. (A) and (C) Bioluminescence imaging (BLI) with representative dorsal images showing the effect of treatment with 56-28z or P28z CARs, at a dose of $1 \times 10^6$ cells, on NSG mice engrafted with GFP-FFLuc OPM2 tumor cells. BLI signal intensity (Radiance) is shown as units of photons/second/square centimeter/steradian. (B) Schematic diagram depicting time points of OPM2 tumor injection and therapeutic intervention with CAR T cells. (D) IgGX, ELISA at 4 weeks post tumor infusion demonstrating negligible levels of human IgGζ in the plasma of 56-28z treated mice compared with the high levels seen in control mice. (E) Long term tumor free survival of 56-28z treated mice at 3 different T cell doses $5 \times 10^6$ ―⊖―, $1 \times 10^6$ ·■· and $0.5 \times 10^6$ ―▲·· compared with control P28z ―✦― treated mice illustrated by Kaplan-Meier curves.
Figure 9C:
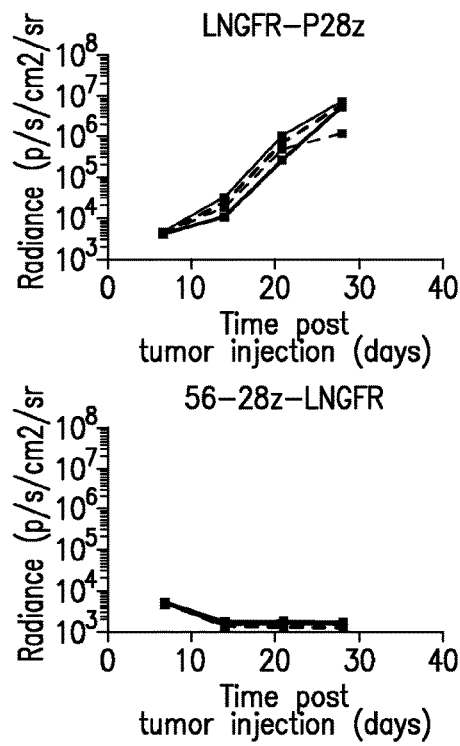
Figure 9B:
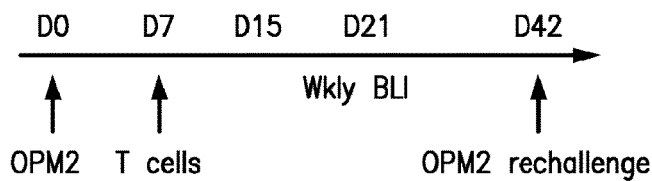

Seven days after OPM2 inoculation, cohorts of mice were treated with either 56-28z-transduced T cells at varying doses (0.5, 1 or 5×10$^6$ CAR+ T cells/mouse) or control P28z CAR T cells given by intravenous injection. BLI monitoring showed impressive rapid eradication of tumor in all the 56-28z CAR T cell treated mice, irrespective of T cell dose, with long-term tumor free survival of greater than 150 days. In contrast, control P28z CAR T cell-treated mice showed exponential tumor growth and uniform development of hind limb paralysis by 35 days. FIGS. 9A-C and E).

Figure 9D:
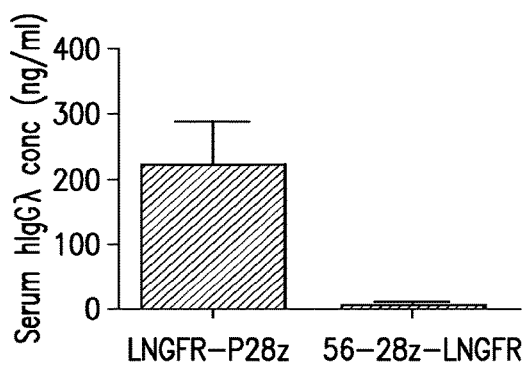
Figure 9E:
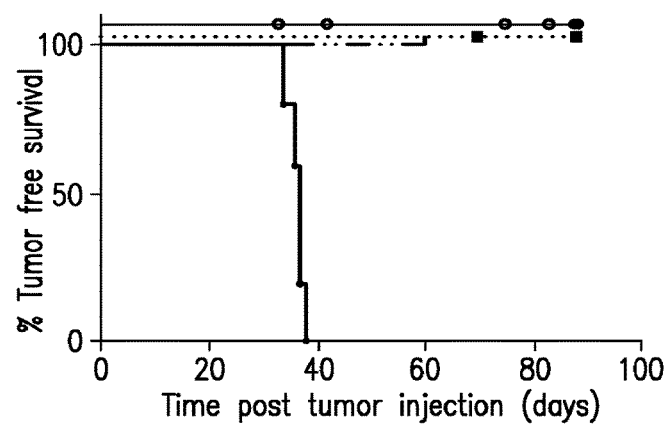

These results were corroborated by evidence of rising hIgGλ, serum levels in control tumor mice compared with undetectable hIgGλ, in the sera of 56-28z CAR T cell treated mice beyond 14 days following tumor injection (FIG. 9D). Post mortem histological analysis on day 35 confirmed that the bone marrow of control mice was obliterated by OPM2 tumor cells, whereas 56-28z CAR T cell treated mice showed no evidence of tumor.

56-28z CAR Therapy Prevented Development of Osteolytic Myeloma Bone Disease.

Figure 10A:
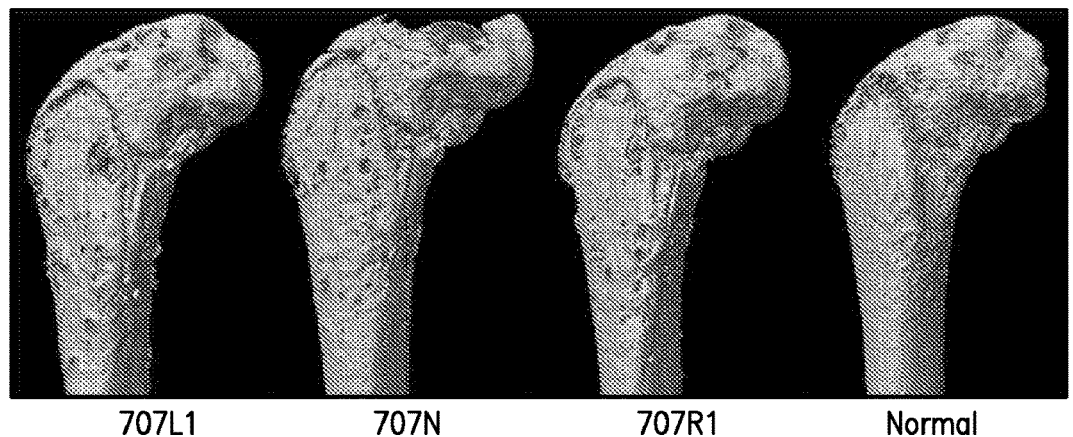
FIGS. 10A-10D depict effect of 56-28z CAR treatment. 56-28z CAR treatment prevents development of osteolytic myeloma bone disease in vivo. (A) Micro-computed tomography pictures of femurs of OPM2 myeloma mice at 4 weeks post tumor injection showing cortical osteolytic lesions (3 representative NSG mice shown along with age, sex matched nontumor control). (B) Representative femoral transverse section image of tumor bearing NSG mouse showing profound loss of bony trabeculae. (C) Histological analysis of tumor bearing NSG mice long bones confirming bone marrow tumor infiltration and cortical bone erosions (see arrows). Decalcified hind limb bones were stained with Masson-Goldner Trichome stain and histomorphometric analysis of trabecular and cortical bone area was performed. Images taken at 20× magnification. (D) Trabecular bone number quantitation from Micro-CT measurement showing a significant effect of 56-28z CAR treatment on myeloma bone disease at 4 weeks post tumor injection compared with tumor bearing mice *$p<0.0001$ by t test. Mean and SEM error bars shown, ♦$p<0.0001$. Cortical bone surface area quantitation however shows no significant difference between 56-28z CAR treated and tumor bearing mice ★★$p=0.252$. and ♦♦$p=0.0197$ showing evidence of cortical bone destruction in tumor mice compared to normal NSG controls.
Figure 10B:
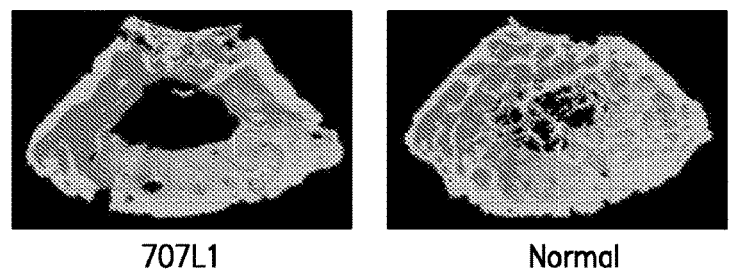
Figure 10C:
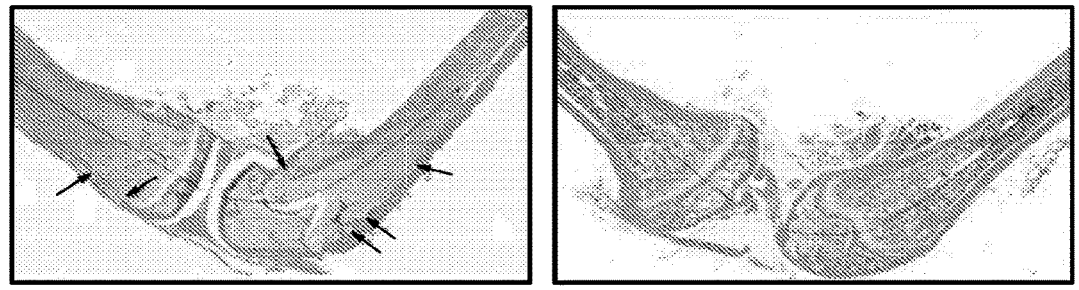
Figure 10D:
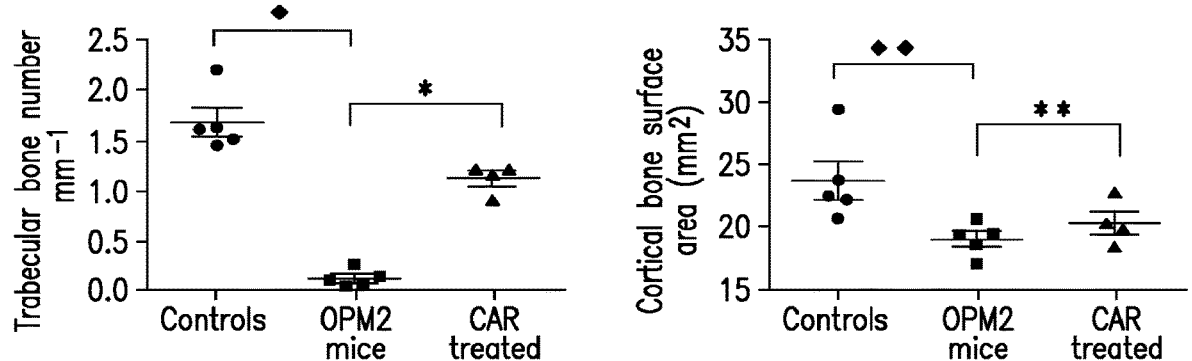

OPM2-infused NSG mice showed both cortical bone osteolytic lesions as well as trabecular bone destruction by micro-computed tomography and histomorphometric analysis (FIG. 10A-C). Treatment of OPM2-infused mice with 56-28z CAR T cells resulted in inhibition of trabecular bone destruction with a significant difference in trabecular bone number and area when bone analysis was performed at 3 weeks post CAR therapy. The development of cortical bone lesions was also reduced slightly but this did not reach statistical significance atleast at this relatively early time-point (FIG. 10D).

Antitumor Efficacy of 56-28z CAR Therapy In Vivo is Mediated by Antigen Dependent Activation, Proliferation and Long Term Persistence of Functional CAR T Cells.

Figure 11A:
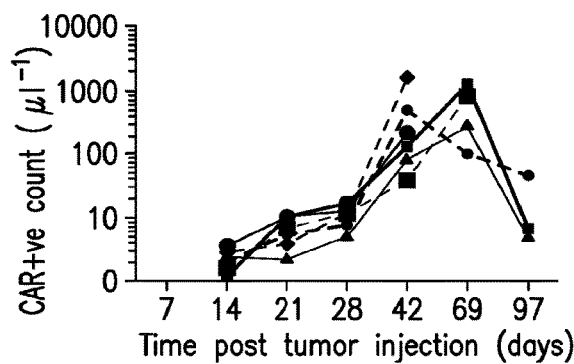
FIGS. 11A-11D depict antitumor efficacy of 56-28z CAR therapy in vivo. Antitumor efficacy of 56-28z CAR therapy in vivo is mediated by antigen dependent T cell proliferation, cytokine production and long term persistence of functional CAR T cells. (A) Graph showing proliferation of CAR T cells in the blood of 56-28z treated (at a dose of 1×10⁶/mouse) tumor bearing NSG mice, as measured by FACS and Countbright beads. (B) Human cytokine secretion in vivo by 56-28z CARs in response to tumor, measured in mouse plasma by luminex assay. Controls include P28z treated tumor mice as well as NSG mice injected with 56-28z CARs alone and no tumor. (C) BLI data showing rejection of tumor by NSG mice previously treated by 56-28z CARs when rechallenged with $1\times10^6$ OPM2 cells at 42 days following the initial tumor injection. In the shown experiment, 5 out of 6 mice rejected tumor rechallenge. Each line represents the results of an individual mouse apart from the initial control P28z treated cohort which is shown on the graph as the mean of 5 mice. Similarly untreated mice injected with OPM2 at the rechallenge timepoint are also shown as the mean value of 3 mice. (D) CTL assay done ex vivo with T cells harvested from 56-28z treated NSG mice showing the antigen specific cytotoxicity of these long term persisting T cells. Targets were E14 murine leukaemia cells with or without human CD56 expression.
Figure 11B:
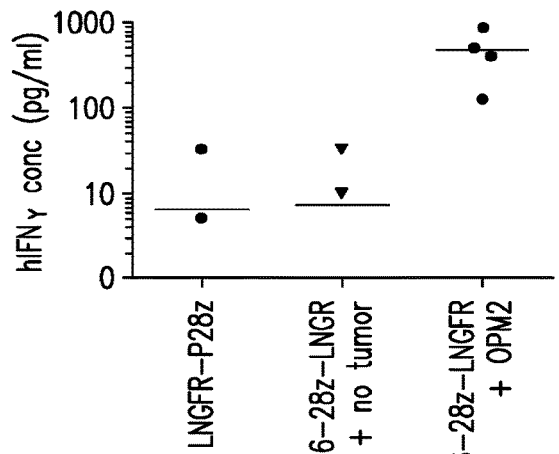

Administration of 1×10$^6$ 56-28z-transduced T cells to OPM2 tumor bearing mice, showed antigen dependent activation and proliferation with a 10-fold expansion within two weeks and eventual decline to stable low levels by 90 days (FIG. 11A). Plasma levels of hIFNx were significantly elevated in 56-28z-treated mice following exposure to tumor but not in tumor free mice, confirming that CAR activation in vivo was antigen dependent (FIG. 11B). Mice, where very high peripheral blood T cell numbers were achieved (>1000 cells/μl), exhibited signs of xenogeneic graft versus host disease (GVHD). No xenogeneic GVHD was observed in P28z-treated mice given the same T cell dose, consistent with a requirement for cognate antigen engagement to expand T cells to levels where GVHD may ensue.

Figure 11C:
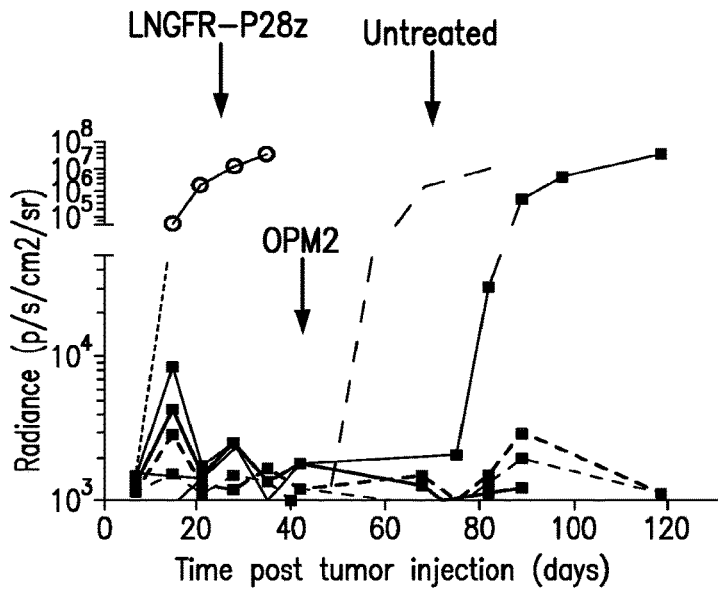

A further significant finding was that 56-28z-expressing T cells were able to persist long term in OPM2-inoculated mice and, importantly, retain their functional activity. OPM2-bearing mice previously treated with 56-28z-transduced T cells were rechallenged with tumor after forty-two days with an intravenous injection of 1×10$^6$ OPM2 cells. Five out of six mice were able to reject the tumor cells with clear evidence of circulating CAR T cells. In contrast, control untreated NSG mice injected with the same dose of tumor cells all developed rapid tumor progression (FIG. 11C).

Figure 11D:
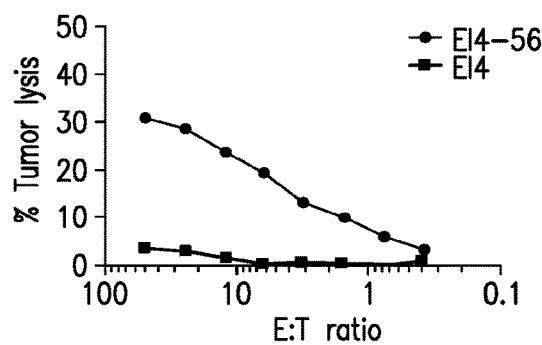

The antigen specificity of these long-term persistent 56-28z CAR T cells was also confirmed by ex vivo evaluation of harvested T cells. These T cells were harvested from the bone marrow and spleen of 56-28z treated mice by day 42 and CTL assays were performed against murine EL4 cells expressing human CD56 (EL4-56) or unmodified EL4 cells, without any prior culture of the retrieved T cells. Significant cytolytic activity was shown only against EL4-56 cells confirming the specificity and functional lytic potential of 56-28z CAR T cells persisting in vivo 6 weeks after their administration (FIG. 11D).

CD56 Positive Target Elimination can be Modulated Through CAR Affinity and Epitope Selection.

Figure 12:
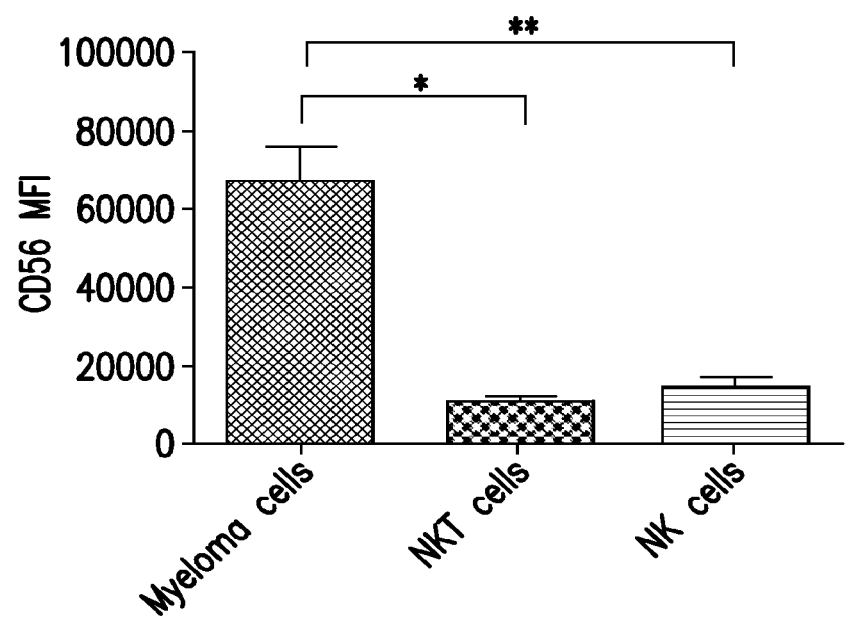
FIG. 12 depicts the FACS data showing difference in mean fluorescence intensity of CD56 between primary myeloma cells and NK as well as NKT cells. *p<0.001, **p<0.001.
Figure 13A:
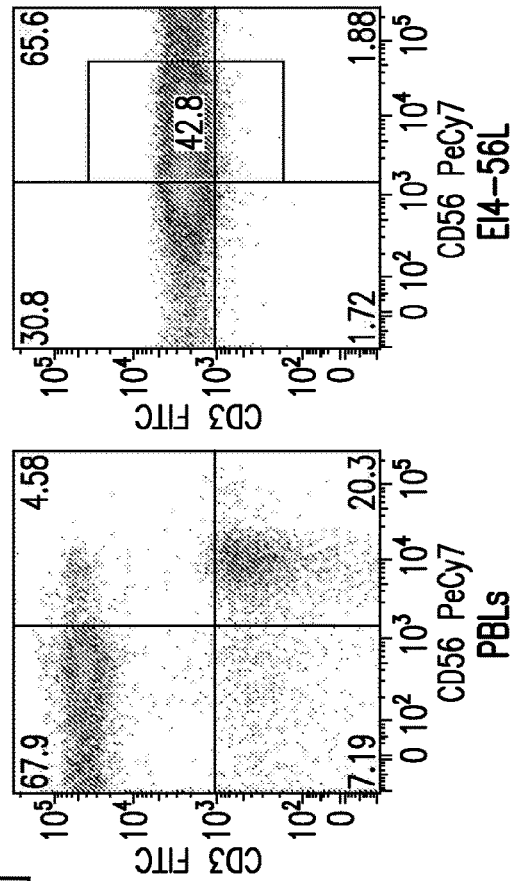
FIGS. 13A-13C depict CD56⁺ target elimination of CD56-targeted CAR. CD56+ target elimination can be modulated through CAR affinity and epitope selection. (A) Schematic diagram depicting generation of CD56 targeted Fabs of differing affinity by phage display technology. (B) Biacore analysis was used to estimate affinity of the Fabs. The four Fabs m903, m904, m905 and m906 generated by the light chain shuffling technique have identical specificity whereas m900 (which can also be referred to as m907) has a diiferent CD56 binding epitope. The murine antibody derived 56-28z CAR is known to have a high affinity but could not be compared directly with the human anti-CD56 Fabs. (C) FACS plot comparing CD56 expression of primary NK and NKT cells with EL4-56L cells.
Figure 13B:
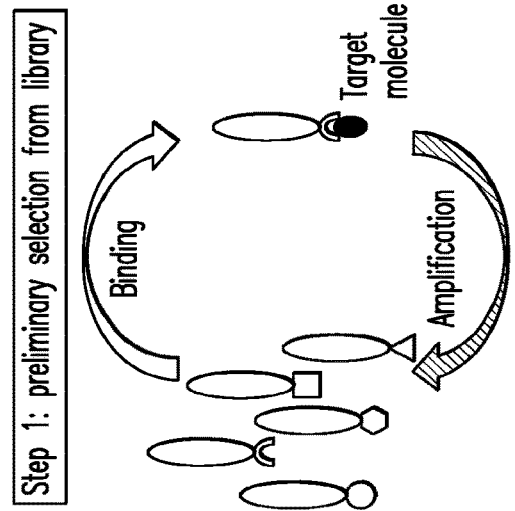

A major concern in targeting CD56 is the risk of on-target, off-tumor tissue destruction. As shown in FIG. 12, CD56+ myeloma typically expresses high levels of CD56, exceeding levels found on NK and T cells. Strategies were evaluated to minimize the on-target, off-tumor toxicity of CD56 targeted CARs. A panel of anti-CD56 CARs with varying affinities ranging from 2.3×10$^{-7}$ M (low affinity) to 2.90× 10$^{-9}$ M (high affinity) were developed using anti-CD56 Fabs generated by phage display technology (FIG. 13A-B). Four of these CARs (m903, m904, m905 and m906) had overlapping epitopes whereas m900 was directed against a different epitope. The cytolytic activity of these CARs was compared against EL4 cells expressing high or low levels of human CD56.

Without being bound to a particular theory, for a given CD56 binding epitope there appears to be a correlation between affinity and CAR activity with the high affinity m905 and m906 CARs demonstrating marked cytolytic activity, comparable to that imparted by the murine scFv-based 56-28z CAR. In contrast, the low affinity m903 and m904 CARs had minimal cytolytic activity against EL4-56$^{low\ or\ high}$ cells (FIG. 2). There was also a correlation between target cell antigen density and CAR activity with the overall level of target cell killing significantly reduced in EL4-56L cells compared with El4-56H cells, in a similar affinity dependent manner. The high affinity m900 CAR showed the highest level of target cell killing against E14-56H cells but was strikingly reduced when the target cell antigen density was low. The ability of such a high affinity anti-CD56 CAR to discriminate between high and low antigen expressing target cells could potentially be utilized in a clinical setting where myeloma cells express CD56 at significantly higher levels than in normal tissue such as NK or NKT cells (FIG. 12). The FACS data show that the level of CD56 expression on NKT and NK cells is comparable to that of EL4-56L cells (FIG. 13C) while primary myeloma cells express CD56 at levels similar to EL4-56H.

3.3 Discussion

Adoptive T cell therapy with genetically enhanced T cells is a promising therapy for patients with certain hematological malignancies, in particular ALL (Kalos, et al. T cells with chimeric antigen receptors have potent antitumor effects and can establish memory in patients with advanced leukemia. *Sci Transl Med.* 3 (95): 95ra73 (2011); Brentj ens, et al. CD19-targeted T cells rapidly induce molecular remissions in adults with chemotherapy-refractory acute lymphoblastic leukemia. *Sci Transl Med.* 5(177):177ra138 (2013); Grupp, et al. Chimeric antigen receptor-modified T cells for acute lymphoid leukemia. *N Engl J Med.* 368(16):1509-1518 (2013)). CAR technology has not yet been sufficiently evaluated in patients with multiple myeloma, although preliminary results have been reported from two clinical trials using CARs directed against kappa light chain immunoglobulin (kIg) (Ramos, et al. Clinical Responses In Patients Infused With T Lymphocytes Redirected To Target K-Light Immunoglobulin Chain. American Society of Hematology Annual meeting. New Orleans, Abstract 506 (2013)) and CD19 (Garfall, ASCO, Abstract (2015)). Other clinical trials have recently opened, targeting either CD138 or NKG2D-ligand (clinicaltrials.gov/NCT01886976, NCT02203825), but no clinical results have yet been published. CD19 is expressed in only a small subset of myeloma patients (Mateo, et al. Prognostic value of immunophenotyping in multiple myeloma: a study by the PETHEMA/GEM cooperative study groups on patients uniformly treated with high-dose therapy. *J Clin Oncol.* 26(16):2737-2744 (2008); Lin, et al. Flow cytometric immunophenotypic analysis of 306 cases of multiple myeloma. *Am J Clin Pathol.* 121(4): 482-488 (2004)) and therefore its usefulness as a target in myeloma is likely to be limited. A report suggesting that myeloma stem cells may be CD19-positive (Matsui, et al. Characterization of clonogenic multiple myeloma cells. *Blood.* 103(6):2332-2336 (2004)) has not been confirmed to date. CD138 is uniformly strongly expressed in myeloma cells at diagnosis but the level of expression is frequently reduced at relapse and following bortezomib treatment (Kawano, Int. J. Oncol. (2012); Tagoug (2013)). NKG2D-ligands are widely expressed in myeloma but with a heterogeneous pattern of expression (Carbone, Blood (2005)). Clinical trials utilizing T cells engineered with HLA-restricted T cell receptors (TCRs) directed against the cancer testis antigens NYESO-1 and MAGE A3 have also been initiated. NYESO-1 is expressed at RNA level in 60% of myeloma patients at diagnosis although this may not always be reflected in protein expression (van Rhee, et al. NY-ESO-1 is highly expressed in poor-prognosis multiple myeloma and induces spontaneous humoral and cellular immune responses. *Blood.* 105(10):3939-3944 (2005)). MAGE A3 expression is found in upto 50% of patients with myeloma and here too there is a heterogeneous pattern of expression, with one study showing staining in <25% of tumor cells (Dhodapkar, et al. (2003)). Preliminary results show minimal toxicity and encouraging responses when the NYESO-1 TCR was administered following a melphalan conditioned autologous stem cell transplant (Rapoport, et al. Engineered T-Cells Expressing An HLA-Restricted Affinity-Enhanced TCR In Advanced Multiple Myeloma Patients Post Auto-SCT Engraft and Are Associated With Encouraging Post Auto-SCT Responses. American Society of Hematology Annual meeting. New Orleans, Abstract 766 (2013)). Studies utilizing a MAGE A3 TCR have however shown severe cardiac toxicity due to unforeseen peptide cross-reactivity (Linette, et al. Cardiovascular toxicity and titin cross-reactivity of affinity-enhanced T cells in myeloma and melanoma. *Blood.* 122(6):863-871 (2013)).

A critical challenge for CAR therapy in myeloma is the need to identify suitable targets. An ideal target would be tumor-specific, present on all tumor cells, highly expressed, and found in most if not all patients. Few known targets meet these criteria. Even the paradigmatic CD19 does not fulfill all of these, as CD19 is expressed on normal B lineage cells. CD56 was investigated as a target for myeloma CAR therapy because it is frequently, intensely and homogenously expressed in myeloma (Tassone, et al. In vitro and in vivo activity of the maytansinoid immunoconjugate huN901-N2'-deacetyl-N2'-(3-mercapto-1-oxopropyl)-maytansine against CD56+ multiple myeloma cells. *Cancer Res.* 64(13):4629-4636 (2004); Bataille, et al. The phenotype of normal, reactive and malignant plasma cells. Identification of 'many and multiple myelomas' and of new targets for myeloma therapy. *Haematologica.* 91(9):1234-1240 (2006)). CD56 expression is also not known to be lost during the course of the disease or at any stage of relapse (Rawstron, et al. Distribution of myeloma plasma cells in peripheral blood and bone marrow correlates with CD56 expression. *Br J Haematol.* 104(1):138-143 (1999)).

As shown in this Example, CD56 targeted CARs can both eradicate tumor and prevent myeloma bone disease. In addition, 56-28z CAR T cells given intravenously to NOD/SCID©c$^{null}$ mice at a moderate cell dose for this kind of model ($5 \times 10^5$ CAR+ T cells per mouse) home to the bone marrow, the main site of disease in the OPM2 myeloma model, become activated, exhibit cytolytic activity against CD56+ myeloma cells and prevent development of myeloma bone disease. The OPM2 cell line used in this model carries the t(4;14) translocation, a key poor prognostic genetic risk factor in myeloma, making the results of the disclosed CAR therapy all the more significant. Furthermore, sustained persistence of 56-28z CAR T cells in mice with preservation of their functional activity and strong protection against a tumor re-challenge after 6 weeks was observed.

CD56, however, is expressed on normal tissues including activated T cells, NK cells and neuronal cells. Although present at a significantly lower density than on myeloma cells (15-fold lower by FACS analysis), this poses legitimate concerns for off-tumor effects. These include failure of CAR T cells to expand because of fratricide elimination, deletion of activated T cells and NK cells, exposure to infectious risks and CNS toxicity.

CD56 is upregulated on a subset of activated T cells; however, elimination of CD56+ T cells from the infused T cell pool did not impair the ability of 56-28z CAR+ T cells to expand in vivo, eliminate tumor cells or persist. Similarly, depletion of recipient CD56+ T cells is unlikely to impair host immunity as CD56 upregulation on T cells is not a prerequisite for T cell function (Wajchman, et al. Ex vivo expansion of CD8+CD56+ and CD8+CD56− natural killer T cells specific for MUC1 mucin. *Cancer Res.* 64(3):1171-1180 (2004)). NK cells, another potential target of CD56 CAR therapy, play a role in controlling viral infections and in tumor immunosurveillance (Vivier, et al. Innate or adaptive immunity? The example of natural killer cells. *Science.* 331(6013):44-49 (2011)) but severe transient NK cell deficiency has been shown to be well tolerated in SCID patients after allogeneic hematopoietic stem cell transplantation where serious viral infections rarely occur (Buckley R H. Molecular defects in human severe combined immunodeficiency and approaches to immune reconstitution. *Annu Rev Immunol.* 2004; 22:625-655; Fischer, et al. Severe combined immunodeficiency. A model disease for molecular immunology and therapy. *Immunol Rev.* 2005; 203:98-109). Phase I and II clinical trials in myeloma with a monoclonal anti-CD56 antibody (directed against an epitope overlapping the epitopes of the scFvs used in our CAR) revealed minimal hematological toxicity and did not appear to increase the frequency of infections (Berdej a J G. Lorvotuzumab mertansine: antibody-drug-conjugate for CD56+ multiple myeloma. Front Biosci (*Landmark Ed.*) 19:163-170 (2014)).

Neuronal toxicity represents another potential side effect of CD56 targeted therapy. CD56 expression on neurons and glial cells is maximal in utero where it contributes to neuronal growth and migration, and persists in adult brain structures such as the hippocampus (Gascon, et al. *Adv Exp Med Biol.* 663:127-136 (2010); Gascon, et al. Polysialic acid-neural cell adhesion molecule in brain plasticity: from synapses to integration of new neurons. *Brain Res Rev.* 56(1):101-118 (2007)). In clinical trials, use of the anti-CD56 antibody resulted in limited peripheral nervous system toxicity, largely in patients with pre-existing grade 1 peripheral neuropathy (Jesus, et al., Phase I Study of Lorvotuzumab Mertansine (LM, IMGN901) in Combination with Lenalidomide (Len) and Dexamethasone (Dex) in Patients with CD56-Positive Relapsed or Relapsed/Refractory Multiple Myeloma American Society of Hematology Annual meeting, Abstract 728 (2012)). It is possible that an intact blood brain barrier may restrict the number of CAR T cells entering the central nervous system (CNS), although both anti-CD19 CAR T cells and anti-MAGE A3 TCRs were shown to infiltrate the brain following adoptive T cell therapy in ALL (Maude, et al. Chimeric antigen receptor T cells for sustained remissions in leukemia. *N Engl J Med.* 371(16):1507-1517 (2014); Davila, 2014) and melanoma (Morgan, et al. Cancer regression and neurological toxicity following anti-MAGE-A3 TCR gene therapy. *J Immunother* 36(2):133-151 (2013)). In the latter case, TCR cross-reactivity with MAGE A12 expressed in the brain caused severe neurological toxicity. The presence of tumor in the CNS may have been a factor in these cases, although it may not be required. Metastasis to the CNS is unusual in multiple myeloma. Careful patient selection for CD56 CAR therapy with exclusion of those with pre-existing neuropathy and avoidance of concomitant administration of other neurotoxic drugs is advised, as is the use of a suicide gene in any eventual clinical trial.

Figure 13C:
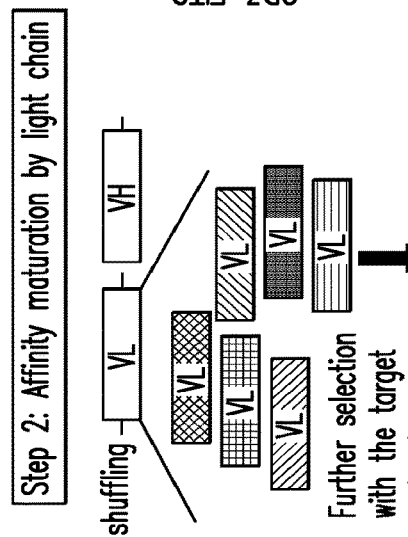

Further strategies to abate T cell activity against normal tissues would further reinforce confidence in targeting CD56. It is hypothesized that an optimal CAR affinity and/or epitope selection can result in preferred killing of cells with high antigen density and spare low expressing cells. To this end, several CARs targeting one of three different CD56 epitopes were generated and tested against target cells expressing different levels of CD56. Without being bound to a particular theory, it was found that using lower affinity scFvs (in the $10^{-8}$ M range) reduced activity against CD56 dim targets without reducing killing of highly positive targets (FIG. 13). The former are representative of lymphocytes and neuronal tissue and the latter of myeloma cells (FIG. 13C). The use of lower affinity CD56 CARs thus represents an attractive approach for a first-in-man clinical study. Without being bound to a particular theory, the disclosed data demonstrates that epitope selection can allow for discrimination between high and low expressing target cells (FIG. 13). Although the precise mechanism for this differential activity remains unexplained, it is plausible that a poorly accessible epitope may result in minimal activity at low antigen density and be rescued by increased T cell avidity at high antigen density. The downside to this strategy is the possibility of tumor escape with $CD56^{low}$ expressing myeloma cells evading CAR binding. The data within this Example however shows that in the majority of patients with CD56 positive myeloma, the cell to cell variation in intensity of CD56 expression within the same patient is minor, making tumor escape from a low affinity 56-28z CAR a lesser concern (FIG. 12).

Previous studies have shown encouraging preclinical results using CARs directed against BCMA, CS-1, CD138, CD38, Lewis Y, kIg and NKG2D receptor (Carpenter, et al. B-cell maturation antigen is a promising target for adoptive T-cell therapy of multiple myeloma. *Clin Cancer Res.* 19(8): 2048-2060 (2013); Chu, et al. Genetic modification of T cells redirected toward CS1 enhances eradication of myeloma cells. *Clin Cancer Res.* 20(15):3989-4000 (2014); Jiang et al. Transfection of chimeric anti-CD138 gene enhances natural killer cell activation and killing of multiple myeloma cells. *Mol Oncol.* 8(2):297-310 (2014); Mihara, et al. T-cell immunotherapy with a chimeric receptor against CD38 is effective in eliminating myeloma cells. *Leukemia.* 26(2):365-367 (2012); Peinert, et al. Gene-modified T cells as immunotherapy for multiple myeloma and acute myeloid leukemia expressing the Lewis Y antigen. *Gene Ther.* 17(5): 678-686 (2010); Vera, et al. T lymphocytes redirected against the kappa light chain of human immunoglobulin efficiently kill mature B lymphocyte-derived malignant cells. *Blood.* 108(12):3890-3897 (2006); Barber, et al. Chimeric NKG2D receptor-expressing T cells as an immunotherapy for multiple myeloma. *Exp Hematol.* 36(10):1318-1328 (2008)). Nonetheless, each one of these targets has potential limitations. BCMA is a tumor necrosis factor family protein that is heterogeneously expressed in primary myeloma and present in normal B lymphocytes and plasma cells (Moreaux, et al. BAFF and APRIL protect myeloma cells from apoptosis induced by interleukin 6 deprivation and dexamethasone. *Blood.* 103(8):3148-3157 (2004); Kwee, et al. Evaluation Of Bcma As a Therapeutic Target In Multiple Myeloma Using An Antibody-Drug Conjugate. American Society of Hematology Annual meeting. New Orleans, Abstract 4447 (2013)). No data are yet available on the use of a BCMA antibody in myeloma patients. BCMA CARs showed tumor specific killing of MM cell lines and primary cells in vitro as well as eliminating intradermally implanted MM cells in NSG mice, although the follow-up period was relatively short (30 days) (Carpenter, et al. B-cell maturation antigen is a promising target for adoptive T-cell therapy of multiple myeloma. *Clin Cancer Res.* 19(8):2048-2060 (2013)). CS-1 shows strong expression in myeloma and is also expressed by NK cells, normal plasma cells and some T cell subsets (Hsi, et al. CS1, a potential new therapeutic antibody target for the treatment of multiple myeloma. *Clin Cancer Res.* 14(9):2775-2784 (2008)). The monoclonal antibody Elotuzumab directed against CS-1 did not induce significant responses when used alone, but therapeutic benefit was reported when it was given in combination with lenalidomide (Zonder, et al. A phase 1, multicenter, open-label, dose escalation study of elotuzumab in patients with advanced multiple myeloma. *Blood.* 120(3):552-559 (2012); Benson, et al. CS1-directed monoclonal antibody therapy for multiple myeloma. *J Clin Oncol.* 30(16):2013-2015 (2012)). CS-1 CAR T cells prolonged survival in MM1S and IMG9 MM engrafted NSG mice, although long term follow-up was limited (Chu, et al. Genetic modification of T cells redirected toward CS1 enhances eradication of myeloma cells. *Clin Cancer Res.* 20(15):3989-4000 (2014)). CD138 CARs introduced in NK cells delayed progression of myeloma cell lines implanted subcutaneously in immunodeficient mice, but all mice eventually succumbed to the tumor (Jiang, et al. Transfection of chimeric anti-CD138 gene enhances natural killer cell activation and killing of multiple myeloma cells. *Mol Oncol.* 8(2):297-310 (2014)). CD138 is expressed homogeneously in myeloma but also widely on epithelial cells and normal plasma cells. Grade 1-2 diarrhea was frequently seen in a phase I trial using an anti-CD138 antibody (Leonard, et al. BT062, an Antibody-Drug Conjugate Directed Against CD138, Given Weekly for 3 Weeks in Each 4 Week Cycle: Safety and Further Evidence of Clinical Activity. American Society of Hematology Annual meeting, Abstract 4042 (2012)). CD38 is another strongly expressed antigen in myeloma but it is expressed on a number of haematopoietic cells including B cells, activated T cells, NK cells and the common myeloid progenitor. In its favor though are the impressive results seen with the monoclonal antibody Daratumumab both as monotherapy and in combination with lenalidomide (Torben, et al. Preliminary Safety and Efficacy Data Of Daratumumab In Combination With Lenalidomide and Dexamethasone In Relapsed Or Refractory Multiple Myeloma. American Society of Hematology Annual meeting, Abstract 1986 (2013)). CD38 CARs also show cytotoxicity against myeloma cell lines and primary myeloma cells in vitro (Mihara, et al. T-cell immunotherapy with a chimeric receptor against CD38 is effective in eliminating myeloma cells. *Leukemia.* 26(2):365-367 (2012)). Unlike what was observed with CD56 CARs, T cell fratricide killing due to CD38 up-regulation following T cell activation, required the addition of an anti-CD38 antibody to enable T cell culture (Mihara, et al. Activated T-cell-mediated immunotherapy with a chimeric receptor against CD38 in B-cell non-Hodgkin lymphoma. *J Immunother.* 32(7):737-743 (2009)). Lewis Y CARs have also shown anti-myeloma activity in subcutaneous myeloma tumor models but Lewis Y antigen is also found on early myeloid progenitor cells, normal plasma cells and epithelial cells (Cao, et al. The fucosylated histo-blood group antigens H type 2 (blood group O, CD173) and Lewis Y (CD174) are expressed on CD34+ hematopoietic progenitors but absent on mature lymphocytes. *Glycobiology.* 11(8): 677-683 (2001); Kitamura, et al. Specificity analysis of blood group Lewis-y (Le(y)) antibodies generatedagainst synthetic and natural Le(y) determinants. *Proc Natl Acad Sci USA.* 91(26):12957-12961 (1994)). The first reported clinical trial of a CAR in myeloma used the kappa light chain CAR but no objective responses were seen in the three patients treated so far (Ramos, et al. Clinical Responses In Patients Infused With T Lymphocytes Redirected To Target κ-Light Immunoglobulin Chain. American Society of Hematology Annual meeting. New Orleans, Abstract 506 (2013). A limiting factor may be the weak expression of IG in most myeloma cells. NKG2D ligands are strongly expressed on primary myeloma cells but they are also upregulated on other cells including NK cells, myeloid suppressive cells, regulatory T cells, endothelial cells in the tumor microenvironment and synoviocytes in inflamed joints (Sentman, et al. NKG2D CARs as cell therapy for cancer. *Cancer J.* 20(2):156-159 (2014)). NKG2D-based CARs showed specific cytotoxicity against MINI cell lines in vitro, using T cells from both normal donors and MM patients (Barber, et al. Chimeric NKG2D receptor-expressing T cells as an immunotherapy for multiple myeloma. *Exp Hematol.* 36(10):1318-1328 (2008)).

In comparison to these other candidate MM CAR targets, the advantage of CD56 is its high intensity and homogenous expression in a majority of patients. CD56 may also serve a target in other poor prognosis hematological malignancies such as NK cell lymphoma (Tse, et al. How I treat NK/T-cell lymphomas. *Blood.* 121(25):4997-5005 (2013)) and CD56+ AML (Raspadori, et al. CD56 antigenic expression in acute myeloid leukemia identifies patients with poor clinical prognosis. *Leukemia.* 15(8):1161-1164 (2001)). In the absence of an ideal myeloma target, combinatorial approaches based on multi-antigen targeting may represent an alternate strategy to reduce off-tumor reactivity. A combinatorial antigen targeting CAR that preferentially targets tumor cells expressing two separate antigens whilst sparing single antigen positive cells was previously disclosed (Kloss, et al. Combinatorial antigen recognition with balanced signaling promotes selective tumor eradication by engineered T cells. *Nat Biotechnol.* 2013; 31(1):71-75). This was achieved by having two CARs targeting different antigens linked independently to the activating and costimulatory signaling domains, thereby ensuring that full T cell activation would only occur when both antigens were engaged. Judicious selection of the two antigens, for instance CD56 and one of the above, may allow preferential targeting of myeloma cells while sparing the single positive normal cells.

From the foregoing description, it will be apparent that variations and modifications may be made to the invention described herein to adopt it to various usages and conditions. Such embodiments are also within the scope of the following claims.

All patents and publications and sequences referred to by accession or reference number mentioned in this specification are herein incorporated by reference to the same extent as if each independent patent and publication and sequence was specifically and individually indicated to be incorporated by reference.

What is claimed is:

1. A chimeric antigen receptor (CAR), comprising an extracellular antigen-binding domain that binds to human CD56, a transmembrane domain, and an intracellular domain, wherein the extracellular antigen-binding domain comprises a heavy chain variable region and a light chain variable region, wherein:
   (a) the heavy chain variable region comprises a CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 3; and the light chain variable region comprising a CDR1 comprising the amino acid sequence set forth in SEQ ID NO: 4, a CDR2 comprising the amino acid sequence set forth in SEQ ID NO: 5, and a CDR3 comprising the amino acid sequence set forth in SEQ ID NO: 6;
   (b) the heavy chain variable region comprises a CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 59; the light chain variable region comprises a CDR1 comprising the amino acid sequence set forth in SEQ ID NO: 4, a CDR2 comprising the amino acid sequence set forth in SEQ ID NO: 5, and a CDR3 comprising the amino acid sequence set forth in SEQ ID NO: 6;
   (c) the heavy chain variable region comprises a CDR1 comprising the amino acid sequence set forth in SEQ ID NO: 9, a CDR2 comprising the amino acid sequence set forth in SEQ ID NO: 10, and a CDR3 comprising the amino acid sequence set forth in SEQ ID NO: 11; and the light chain variable region comprises a CDR1 comprising the amino acid sequence set forth in SEQ ID NO: 12, a CDR2 comprising the amino acid sequence set forth in SEQ ID NO: 14, and a CDR3 comprising the amino acid sequence set forth in SEQ ID NO: 15;
   (d) the heavy chain variable region comprises a CDR1 comprising the amino acid sequence set forth in SEQ ID NO: 9, a CDR2 comprising the amino acid sequence set forth in SEQ ID NO: 10, and a CDR3 comprising the amino acid sequence set forth in SEQ ID NO: 11; and the light chain variable region comprises a CDR1 comprising the amino acid sequence set forth in SEQ ID NO: 12, a CDR2 comprising the amino acid sequence set forth in SEQ ID NO: 14, and a CDR3 comprising the amino acid sequence set forth in SEQ ID NO: 16;
   (e) the heavy chain variable region comprises a CDR1 comprising the amino acid sequence set forth in SEQ ID NO: 9, a CDR2 comprising the amino acid sequence set forth in SEQ ID NO: 10, and a CDR3 comprising the amino acid sequence set forth in SEQ ID NO: 11; and the light chain variable region comprises a CDR1 comprising the amino acid sequence set forth in SEQ ID NO: 12, a CDR2 comprising the amino acid sequence set forth in SEQ ID NO: 14, and a CDR3 comprising the amino acid sequence set forth in SEQ ID NO: 17; or
   (f) the heavy chain variable region comprises a CDR1 comprising the amino acid sequence set forth in SEQ ID NO: 9, a CDR2 comprising the amino acid sequence set forth in SEQ ID NO: 10, and a CDR3 comprising the amino acid sequence set forth in SEQ ID NO: 11; and the light chain variable region comprises a CDR1 comprising the amino acid sequence set forth in SEQ ID NO: 13, a CDR2 comprising the amino acid sequence set forth in SEQ ID NO: 14, and a CDR3 comprising the amino acid sequence set forth in SEQ ID NO: 18.

2. The CAR of claim 1, wherein the heavy chain variable region comprises a CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 3; and the light chain variable region comprises a CDR1 comprising the amino acid sequence set forth in SEQ ID NO: 4, a CDR2 comprising the amino acid sequence set forth in SEQ ID NO: 5, and a CDR3 comprising the amino acid sequence set forth in SEQ ID NO: 6.

3. The CAR of claim 1, wherein the heavy chain variable region comprises a CDR1 comprising the amino acid sequence set forth in SEQ ID NO: 1, a CDR2 comprising the amino acid sequence set forth in SEQ ID NO: 2, and a CDR3 comprising the amino acid sequence set forth in SEQ ID NO: 59; and the light chain variable region comprises a CDR1 comprising the amino acid sequence set forth in SEQ ID NO: 4, a CDR2 comprising the amino acid sequence set forth in SEQ ID NO: 5, and a CDR3 comprising the amino acid sequence set forth in SEQ ID NO: 6.

4. The CAR of claim 1, wherein:
   (i) the heavy chain variable region comprises the amino acid sequence set forth in SEQ ID NO:7; and the light chain variable region comprises the amino acid sequence set forth in SEQ ID NO:8;
   (ii) the heavy chain variable region comprises the amino acid sequence set forth in SEQ ID NO: 19; and the light chain variable region comprises the amino acid sequence set forth in SEQ ID NO: 20;
   (iii) the heavy chain variable region comprises the amino acid sequence set forth in SEQ ID NO: 21; and the light chain variable region comprises the amino acid sequence set forth in SEQ ID NO: 22;

(iv) the heavy chain variable region comprises the amino acid sequence set forth in SEQ ID NO: 23; and the light chain variable region comprises the amino acid sequence set forth in SEQ ID NO: 24; or (v) the heavy chain variable region comprises the amino acid sequence set forth in SEQ ID NO: 25; and the light chain variable region comprises the amino acid sequence set forth in SEQ ID NO: 26.

5. The CAR of claim 1, wherein the extracellular antigen-binding domain comprises a single-chain variable fragment (scFv), a Fab that is optionally crosslinked, or a F(ab)$_2$.

6. The CAR of claim 1, wherein the extracellular antigen-binding domain comprises a human scFv.

7. The CAR of claim 5, wherein one or more of the scFV, Fab and F(ab)$_2$ are comprised in a fusion protein with a heterologous sequence to form the extracellular antigen-binding domain.

8. The CAR of claim 1, wherein the extracellular antigen-binding domain comprises a linker between the heavy chain variable region and the light chain variable region.

9. The CAR of claim 1, the transmembrane domain comprises a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, or a combination thereof.

10. The CAR of claim 9, wherein the transmembrane domain comprises a CD28 polypeptide.

11. The CAR of claim 1, wherein the intracellular domain comprises a CD3ζ polypeptide.

12. The CAR of claim 1, wherein the intracellular domain further comprises at least one co-stimulatory signaling region.

13. The CAR of claim 12, wherein the at least one co-stimulatory signaling region comprises a CD28 polypeptide, a 4-1BB polypeptide, an OX40 polypeptide, an ICOS polypeptide, a DAP-10 polypeptide, or a combination thereof.

14. The CAR of claim 13, wherein the at least one co-stimulatory signaling region comprises a CD28 polypeptide.

15. The CAR of claim 1, wherein the transmembrane domain comprises a CD28 polypeptide, and the intracellular domain comprises a CD3ζ polypeptide and a co-stimulatory signaling domain comprising a CD28 polypeptide.

16. The CAR of claim 1, wherein the CAR is recombinantly expressed or expressed from a vector.

17. An immunoresponsive cell comprising the CAR of claim 1.

18. The immunoresponsive cell of claim 17, wherein the CAR is constitutively expressed on the surface of the immunoresponsive cell.

19. The immunoresponsive cell of claim 17, wherein the immunoresponsive cell is selected from the group consisting of a T cell, a Natural Killer (NK) cell, a human embryonic stem cell, a lymphoid progenitor cell, a T cell-precursor cell, and a pluripotent stem cell from which lymphoid cells may be differentiated.

20. The immunoresponsive cell of claim 19, wherein the immunoresponsive cell is a T cell.

21. The immunoresponsive cell of claim 20, wherein the T cell is selected from the group consisting of a cytotoxic T lymphocyte (CTL), a regulatory T cell, and central memory T cells.

22. The immunoresponsive cell of claim 1, further comprising an antigen recognizing receptor that binds to a second antigen that is different than human CD56.

23. The immunoresponsive cell of claim 22, wherein the second antigen is selected from the group consisting of CD138, CS-1, BCMA, CT-7, carbonic anhydrase IX (CAIX), carcinoembryonic antigen (CEA), CD5, CD7, CD10, CD19, CD20, CD22, CD30, CD33, CD34, CD38, CD41, CD44, CD49f, CD74, CD123, CD133, an antigen of a cytomegalovirus (CMV) infected cell, epithelial glycoprotein2 (EGP 2), epithelial glycoprotein-40 (EGP-40), epithelial cell adhesion molecule (EpCAM), receptor tyrosine-protein kinases Erb-B2, Erb-B3, Erb-B4, folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1CAM), melanoma antigen family A1 (MAGE-A1), MAGE-A3, Mucin 16 (Muc-16), Mucin 1 (Muc-1), mesothelin, NKG2D ligands, cancer-testis antigen NY-E50-1, oncofetal antigen (h5T4), prostate stem cell antigen (PSCA), prostate-specific membrane antigen (PSMA), tumor associated glycoprotein 72 (TAG-72), vascular endothelial growth factor R2 (VEGF R2), Wilms tumor protein (WT-1), and a combination thereof.

24. The immunoresponsive cell of claim 23, wherein the second antigen is CD138.

25. The immunoresponsive cell of claim 22, wherein the antigen recognizing receptor is a truncated CAR, or a chimeric co-stimulatory receptor (CCR).

26. A nucleic acid molecule encoding the chimeric antigen receptor (CAR) of claim 1.

27. A vector comprising the nucleic acid molecule of claim 26.

28. A host cell expressing the nucleic acid molecule of claim 26.

29. A method for producing an immunoresponsive cell that binds to human CD56, comprising introducing into the immunoresponsive cell a nucleic acid sequence that encodes the CAR of claim 1.

30. A pharmaceutical composition comprising an effective amount of the immunoresponsive cell of claim 17 and a pharmaceutically acceptable excipient.

31. A kit for treating a neoplasm, comprising the immunoresponsive cell of claim 17 and written instructions for using the immunoresponsive cell for treating a subject having a neoplasm.

32. The CAR of claim 1, wherein the extracellular antigen-binding domain specifically binds to human CD56 with a binding affinity ($K_d$) of about $3 \times 10^{-9}$M or less.

33. The CAR of claim 1, wherein the extracellular antigen-binding domain specifically binds to human CD56 with a binding affinity ($K_d$) of from about $3 \times 10^{-9}$M to about $2 \times 10^{-7}$ M.

34. The CAR of claim 1, wherein the heavy chain variable region comprises the amino acid sequence set forth in SEQ ID NO:7; and the light chain variable region comprises the amino acid sequence set forth in SEQ ID NO:8.

35. The CAR of claim 1, wherein a signal peptide that is covalently joined to the 5' terminus of the extracellular antigen-binding domain.

36. The immunoresponsive cell of claim 23, wherein the antigen of a cytomegalovirus (CMV) infected cell is a cell surface antigen.

* * * * *